United States Patent
Lo et al.

(10) Patent No.: US 11,605,445 B2
(45) Date of Patent: Mar. 14, 2023

(54) ANALYSIS OF FRAGMENTATION PATTERNS OF CELL-FREE DNA

(71) Applicant: The Chinese University of Hong Kong, Shatin (HK)

(72) Inventors: Yuk-Ming Dennis Lo, Homantin (CN); Rossa Wai Kwun Chiu, Shatin (CN); Kwan Chee Chan, Shatin (CN); Peiyong Jiang, Shatin (CN)

(73) Assignee: The Chinese University of Hong Kong, Shatin (HK)

( * ) Notice: Subject to any disclaimer, the term of this patent is extended or adjusted under 35 U.S.C. 154(b) by 703 days.

(21) Appl. No.: 16/566,686

(22) Filed: Sep. 10, 2019

(65) Prior Publication Data

US 2020/0005895 A1    Jan. 2, 2020

Related U.S. Application Data

(60) Division of application No. 15/218,497, filed on Jul. 25, 2016, now Pat. No. 10,453,556, which is a continuation-in-part of application No. PCT/CN2016/073753, filed on Feb. 14, 2016.

(60) Provisional application No. 62/294,948, filed on Feb. 12, 2016, provisional application No. 62/196,250, filed on Jul. 23, 2015.

(51) Int. Cl.

| | | |
|---|---|---|
| G16B 30/10 | (2019.01) | |
| G16B 30/00 | (2019.01) | |
| G16B 20/00 | (2019.01) | |
| G16B 25/00 | (2019.01) | |
| C12Q 1/6883 | (2018.01) | |
| C12Q 1/6869 | (2018.01) | |
| C12Q 1/6827 | (2018.01) | |
| G16B 20/20 | (2019.01) | |
| G16B 25/10 | (2019.01) | |
| G16B 20/10 | (2019.01) | |
| C12Q 1/6876 | (2018.01) | |
| C12Q 1/6886 | (2018.01) | |

(52) U.S. Cl.
CPC .......... *G16B 30/10* (2019.02); *C12Q 1/6827* (2013.01); *C12Q 1/6869* (2013.01); *C12Q 1/6876* (2013.01); *C12Q 1/6883* (2013.01); *C12Q 1/6886* (2013.01); *G16B 20/00* (2019.02); *G16B 20/10* (2019.02); *G16B 20/20* (2019.02); *G16B 25/00* (2019.02); *G16B 25/10* (2019.02); *G16B 30/00* (2019.02); *C12Q 2600/156* (2013.01)

(58) Field of Classification Search
CPC ........ G16B 30/10; G16B 20/20; G16B 25/10; G16B 30/00; G16B 20/00; G16B 20/10; G16B 25/00; C12Q 1/6876; C12Q 1/6883; C12Q 1/6886; C12Q 1/6827; C12Q 1/6869
See application file for complete search history.

(56) References Cited

U.S. PATENT DOCUMENTS

| | | |
|---|---|---|
| 10,240,209 B2 | 3/2019 | Lo et al. |
| 10,453,556 B2 | 10/2019 | Lo et al. |
| 2003/0219765 A1 | 11/2003 | Costa |
| 2005/0282196 A1 | 12/2005 | Costa |
| 2013/0017958 A1 | 1/2013 | Benz et al. |
| 2013/0040824 A1 | 2/2013 | Lo et al. |
| 2013/0237431 A1 | 9/2013 | Lo et al. |
| 2014/0080715 A1 | 3/2014 | Lo et al. |
| 2014/0100121 A1 | 4/2014 | Lo et al. |
| 2014/0274740 A1 | 9/2014 | Srinivasan et al. |
| 2015/0011403 A1 | 1/2015 | Lo et al. |
| 2015/0087529 A1 | 3/2015 | Lo et al. |
| 2015/0105267 A1* | 4/2015 | Shendure ............ C12Q 1/6869 506/2 |
| 2015/0368708 A1 | 12/2015 | Talasaz |
| 2016/0002717 A1 | 1/2016 | Lee et al. |
| 2016/0292356 A1 | 10/2016 | Kim et al. |
| 2016/0333416 A1 | 11/2016 | Babiarz et al. |
| 2017/0024513 A1 | 1/2017 | Lo et al. |
| 2017/0211142 A1 | 7/2017 | Smargon et al. |
| 2017/0211143 A1 | 7/2017 | Shendure et al. |
| 2017/0260590 A1 | 9/2017 | Eltoukhy et al. |
| 2017/0321284 A1 | 11/2017 | McCarroll et al. |

(Continued)

FOREIGN PATENT DOCUMENTS

| | | |
|---|---|---|
| CN | 103215350 | 7/2013 |
| CN | 104662168 | 5/2015 |

(Continued)

OTHER PUBLICATIONS

Australian Application No. 2016295616, First Examination Report dated Aug. 2, 2021, 3 pages.
Indian Application No. 201847005681, First Examination Report dated Jun. 1, 2021, 6 pages.
European Application No. 21196292.3, Extended European Search Report dated Feb. 15, 2022, 8 pages.
Supplementary Information, Nature, 2012, 25 pages.
TruSeq DNA PCR-Free Sample Preparation Kit, Illumina, Data Sheet: Sequencing, Available online at: http://www.illumina.com/contenUdam/illuminamarketing/documents/products/datasheets/datasheet_truseq_dna_pcr_free_sample_prep.pdf>, 2013, 4 pages.
U.S. Appl. No. 15/362,631, Non-Final Office Action dated Jan. 11, 2018, 7 pages.

(Continued)

*Primary Examiner* — Jerry Lin
(74) *Attorney, Agent, or Firm* — Kilpatrick Townsend & Stockton LLP

(57) ABSTRACT

Factors affecting the fragmentation pattern of cell-free DNA (e.g., plasma DNA) and the applications, including those in molecular diagnostics, of the analysis of cell-free DNA fragmentation patterns are described. Various applications can use a property of a fragmentation pattern to determine a proportional contribution of a particular tissue type, to determine a genotype of a particular tissue type (e.g., fetal tissue in a maternal sample or tumor tissue in a sample from a cancer patient), and/or to identify preferred ending positions for a particular tissue type, which may then be used to determine a proportional contribution of a particular tissue type.

23 Claims, 39 Drawing Sheets

(56) References Cited

U.S. PATENT DOCUMENTS

| | | | |
|---|---|---|---|
| 2017/0356053 | A1 | 12/2017 | Otto et al. |
| 2018/0119230 | A1 | 5/2018 | Velculescu et al. |
| 2019/0309374 | A1 | 10/2019 | Snyder et al. |

FOREIGN PATENT DOCUMENTS

| | | |
|---|---|---|
| CN | 104781422 | 7/2015 |
| JP | 2005514956 | 5/2005 |
| JP | 2013509884 | 3/2013 |
| JP | 2014534507 | 12/2014 |
| WO | 0061612 | 10/2000 |
| WO | 2004111272 | 12/2004 |
| WO | 2008024009 | 2/2008 |
| WO | 2008146309 | 12/2008 |
| WO | 2013060762 | 5/2013 |
| WO | 2013177581 A2 | 11/2013 |
| WO | 2013190441 | 12/2013 |
| WO | 2014039556 | 3/2014 |
| WO | 2014130890 | 8/2014 |
| WO | 2016008451 | 1/2016 |
| WO | 2016015058 | 1/2016 |
| WO | 2016127944 | 8/2016 |
| WO | 2018009723 | 1/2018 |
| WO | 2018112100 | 6/2018 |
| WO | 2021007462 | 1/2021 |

OTHER PUBLICATIONS

Aird et al., Analyzing and Minimizing PCR Amplification Bias in Illumina Sequencing Libraries, Genome Biology, vol. 12, No. R18, Available online at: http://genomebiology.com/2011/12/2/R18, Feb. 2011, pp. 1-14.

Beck et al., Next Generation Sequencing of Serum Circulating Nucleic Acids from Patients with Invasive Ductal Breast Cancer Reveals Differences to Healthy and Nonmalignant Controls, Molecular Cancer Research, vol. 8, No. 3, Mar. 9, 2010, pp. 335-342.

Beck et al., Profile of the Circulating DNA in Apparently Healthy Individuals, Clinical Chemistry, vol. 55, No. 4, Apr. 2009, pp. 730-738.

Chandrananda et al., High-Resolution Characterization of Sequence Signatures due to Non-Random Cleavage of Cell-Free DNA, BMC Medical Genomics, vol. 8, No. 29, Jun. 17, 2015, pp. 1-19.

Chang et al., Assessment of Plasma DNA Levels, Allelic Imbalance and CA 125 as Diagnostic Tests for Cancer, Journal of the National Cancer Institute, vol. 94, No. 22, Nov. 20, 2002, pp. 1697-1703.

Cibulskis et al., Sensitive Detection of Somatic Point Mutations in Impure and Heterogeneous Cancer Samples, Nature Biotechnology, vol. 31, No. 3, Mar. 2013, pp. 213-219.

Diaz Jr. et al., The Molecular Evolution of Acquired Resistance to Targeted EGFR Blockade in Colorectal Cancers, Nature, vol. 486, No. 7404, Jun. 28, 2012, 10 pages.

Diehl et al., Circulating Mutant DNA to Assess Tumor Dynamics, Nature Medicine, vol. 14, No. 9, Sep. 2008, pp. 985-990.

European Application No. 16748745.3, Extended European Search Report dated Sep. 18, 2018, 8 pages.

European Application No. 16827283.9, Extended European Search Report dated Dec. 5, 2018, 7 pages.

Goode et al., A Simple Consensus Approach Improves Somatic Mutation Prediction Accuracy, Genome Medicine, vol. 5, No. 90, 2013, pp. 1-14.

Hanlon et al., Evaluation of 13q14 Status in Multiple Myeloma by Digital Single Nucleotide Polymorphism Technology, Journal of Molecular Diagnostics, vol. 11, No. 5, Sep. 2009, pp. 450-457.

Heidary et al., The Dynamic Range of Circulating Tumor DNA in Metastatic Breast Cancer, Breast Cancer Research, vol. 16, No. 421, Aug. 9, 2014, pp. 1-10.

Hou et al., Single-Cell Exome Sequencing and Monoclonal Evolution of a JAK2- Negative Myeloproliferative Neoplasm, Cell, vol. 148, No. 5, Mar. 2, 2012, pp. 873-885.

Ivanov et al., Non-Random Fragmentation Patterns in Circulating Cell-Free DNA Reflect Epigenetic Regulation, BMC Genomics, vol. 16, Dec. 16, 2015, 12 pages.

Jacobs et al., Detectable Clonal Mosaicism and its Relationship to Aging and Cancer, Nature Genetics, vol. 44, No. 6, May 6, 2012, 20 pages.

Jiang et al., Preferred End Coordinates and Somatic Variants as Signatures of Circulating Tumor DNA Associated with Hepatocellular Carcinoma, Proceedings of the National Academy of Sciences of the United States of America, vol. 115, No. 46, Dec. 5, 2018, pp. E10925-E10933.

Japanese Application No. 2017-559756, Office Action dated Jan. 7, 2020, 12 pages (6 pages of Original Document and 6 pages of English Translation).

Jung et al., Cell-Free DNA in the Blood as a Solid Tumor Biomarker-A Critical Appraisal of the Literature, Clinica Chimica Acta, vol. 411, No. 21-22, Nov. 11, 2010, pp. 1611-1624.

Karlsson et al., Amplification-Free Sequencing of Cell-Free DNA For Prenatal Non-lnvasive Diagnosis of Chromosomal Aberrations, Genomics, vol. 105, No. 3, Mar. 2015, pp. 150-158.

Kinde et al., Detection and Quantification of Rare Mutations with Massively Parallel Sequencing, Proceedings of the National Academy of Sciences, vol. 108, No. 23, Jun. 7, 2011, pp. 9530-9535.

Kitzman et al., Noninvasive Whole-Genome Sequencing of a Human Fetus, Science Translational Medicine, vol. 4, No. 137, Jun. 2012, 11 pages.

Kozarewa et al., Amplification-Free Illumina Sequencing-Library Preparation Facilitates Improved Mapping and Assembly of (GC)-Biased Genomes, Nature Methods, vol. 6, No. 4, Apr. 2009, pp. 291-295.

Leary et al., Detection of Chromosomal Alterations in the Circulation of Cancer Patients with Whole-Genome Sequencing, Science Translational Medicine, vol. 4, No. 162, Nov. 28, 2012, pp. 1-21.

Leary et al., Development of Personalized Tumor Biomarkers Using Massively Parallel Sequencing, Science Translational Medicine, vol. 2, No. 20, Available Online at: www.ScienceTranslationaiMedicine.org, Feb. 24, 2010, 15 pages.

Leary et al., Supplementary Materials for Detection of Chromosomal Alterations in the Circulation of Cancer Patients with Whole-Genome Sequencing, Science Translational Medicine, vol. 4, No. 162, Nov. 28, 2012, 9 pages.

Liao et al., Targeted Massively Parallel Sequencing of Maternal Plasma DNA Permits Efficient and Unbiased Detection of Fetal Alleles, Clinical Chemistry, vol. 57, No. 1, Jan. 2011, pp. 92-101.

Longo, Tumor Heterogeneity and Personalized Medicine, The New England Journal of Medicine, vol. 366, No. 10, Available Online at: www.nejm.org, Mar. 8, 2012, pp. 956-957.

McDermott et al., Genomics and the Continuum of Cancer Care, The New England Journal of Medicine, vol. 364, No. 4, Jan. 27, 2011, pp. 340-350.

Murtaza et al., Non-lnvasive Analysis of Acquired Resistance to Cancer Therapy by Sequencing of Plasma DNA, Nature, vol. 497, No. 7447, May 2, 2013, pp. 108-112.

Navin et al., Future Medical Applications of Single-Cell Sequencing in Cancer, Genome Medicine, vol. 3, No. 31, May 31, 2011, 12 pages.

Navin et al., Tumor Evolution Inferred by Single-Cell Sequencing, Nature, vol. 472, No. 7341, Apr. 7, 2011,14 pages.

International Application No. PCT/CN2016/073753, International Preliminary Report on Patentability dated Aug. 24, 2017, 5 pages.

International Application No. PCT/CN2016/073753, International Search Report and Written Opinion dated May 10, 2016, 7 pages.

International Application No. PCT/CN2016/091531, International Preliminary Report on Patentability dated Feb. 1, 2018, 5 pages.

International Application No. PCT/CN2016/091531, International Search Report and Written Opinion dated Sep. 28, 2016, 11 pages.

International Application No. PCT/US2015/042310, International Search Report and Written Opinion dated Jan. 12, 2016, 17 pages.

Pennisi, Single-Cell Sequencing Tackles Basic and Biomedical Questions, Science, vol. 336, No. 6084, May 25, 2012, pp. 976-977.

Prokunina-Olsson et al., Cancer Sequencing Gets a Little More Personal, Available Online at: www.ScienceTranslationalMedicine.org, vol. 2, No. 20, Feb. 24, 2010, pp. 1-3.

(56) References Cited

OTHER PUBLICATIONS

Psifidi et al., Novel Quantitative Real-time LCR for the Sensitive Detection of SNP Frequencies in Pooled DNA Method Development, Evaluation and Application, PLoS ONE, vol. 6, No. 1, e14560, Jan. 19, 2011, pp. 1-11.

Qin et al., Studying Copy Number Variations Using a Nanofluidic Platform, Nucleic Acids Research, vol. 36, No. 18, Oct. 2008, pp. 1-8.

Razavi et al., Many Cell-free DNA (CfDNA) Mutations are Derived from Clonal Hematopoiesis: Implications for Interpretation of Liquid Biopsy Tests, GRAIL-MSK WBC Poster, ASCO, vol. 35, No. 15, Available online at: https://grail.com/publication/many-cell-free-dna-cfdna-mutations-are-derived-fromclonal-hematopoiesis-implications-for-interpretation-of-liquid-biopsy-tests/>, Jun. 3, 2017, 41 pages.

Razavi et al., Performance of a High-Intensity 508-Gene Circulating-Tumor DNA (ctDNA) Assay in Patients With Metastatic Breast, Lung, and Prostate Cancer, Grail- Msk concordance Poster, ASCOM, vol. 35, No. 18, Available online at: https://grail.com/wpcontenUuploads/2018/05/ASC0_2017 Razavi_Concordance_POS_Final.pdf>, Jun. 2017, 41 pages.

Salani et al., Measurement of Cyclin E Genomic Copy Number and Strand Length in Cell-Free DNA Distinguish Malignant Versus Benign Effusions, Cancer Research, vol. 13, No. 19, Oct. 1, 2007, pp. 5805-5809.

Schwarzenbach et al., Cell-Free Nucleic Acids as Biomarkers in Cancer Patients, Nature Reviews Cancer, Advance Online Publication, vol. 11, No. 6, Jun. 2011, pp. 426-437.

Singapore Application No. 11201706529T, Written Opinion dated Jun. 19, 2018, 7 pages.

Shaw et al., Genomic Analysis of Circulating Cell-Free DNA Infers Breast Cancer Dormancy, Genome Research, vol. 22, No. 2, Feb. 2012, pp. 220-231.

Snyder et al., Cell-Free DNA Comprises an in Vivo Nucleosome Footprint that Informs its Tissues-of-Origin, Cell, vol. 164, Jan. 14, 2016, pp. 57-68.

Snyder et al., Noninvasive Fetal Genome Sequencing: A Primer, NIH Public Access Author Manuscript in PMC, vol. 33, No. 6, Jun. 2013, pp. 547-554.

Snyder et al., Universal Noninvasive Detection of Solid Organ Transplant Rejection, Proceedings of the National Academy of Sciences, vol. 108, No. 15, Apr. 12, 2011, pp. 6229-6234.

Stratton, Exploring the Genomes of Cancer Cells: Progress and Promise, Science, vol. 331, No. 6024, Mar. 25, 2011, pp. 1553-1558.

Straver et al., Calculating the Fetal Fraction for Non Invasive Prenatal Testing Based on Genome-wide Nucleosome Profiles, Supplementary Data, 2016, pp. 1-15.

Straver et al., Calculating the Fetal Fraction for Noninvasive Prenatal Testing Based on Genome-Wide Nucleosome Profiles, Prenatal Diagnosis, vol. 36, 2016, pp. 614-621.

Van Dijk et al., Library Preparation Methods for Next-Generation Sequencing: Tone Down the Bias, Experimental Cell Research, vol. 322, No. 1, Mar. 10, 2014, pp. 12-20.

Wagner, Free DNA—New Potential Analyte in Clinical Laboratory Diagnostics?, Biochemia Medica, vol. 22, No. 1, Feb. 15, 2012, pp. 24-38.

Wang et al., Digital Karyotyping, Proceedings of the National Academy of Sciences U.S.A., vol. 99, No. 25, Dec. 10, 2002, pp. 16156-16161.

Weber et al., Detection of Human Tumor Cells by Amplicon Fusion Site Polymerase Chain Reaction (AFS-PCR), The Journal of Clinical Investigation, vol. 121, No. 2, Feb. 2011, pp. 545-553.

Welch et al., The Origin and Evolution of Mutations in Acute Myeloid Leukemia, Cell, vol. 150, No. 2, Jul. 20, 2012, pp. 264-278.

Xu et al., Single-Cell Exome Sequencing Reveals Single-Nucleotide Mutation Characteristics of a Kidney Tumor, Cell, vol. 148, No. 5, Mar. 2, 2012, pp. 886-895.

Yap et al., Intratumor Heterogeneity: Seeing the Wood for the Trees, Science Translational Medicine, vol. 4, No. 127, Available online at: www.sciencetranslationalmedicine.org, Mar. 28, 2012, pp. 1-4.

Yung et al., Single-Molecule Detection of Epidermal Growth Factor Receptor Mutations in Plasma by Microfluidics Digital PCR in Non-Small Cell Lung Cancer Patients, Clinical Cancer Research, vol. 15, No. 6, Mar. 15, 2009, pp. 2076-2084.

Japanese Application No. 2018-503181, Office Action dated Aug. 25, 2020, 12 pages. (6 pages of Original Document and 6 pages of English Translation).

Taiwan Application No. 105123553, Office Action dated Jul. 31, 2020, 7 pages. (4 pages of Original Document and 3 pages of English Translation).

Sun, et al., Size-Tagged Preferred Ends in Maternal Plasma DNA Shed Light on the Production Mechanism and Show Utility in Noninvasive Prenatal Testing, PNAS, vol. 115, No. 22, pp. E5106-E5114, May 29, 2018.

Non-Final Office Action dated Apr. 14, 2022 in U.S. Appl. No. 16/566,695, filed Sep. 10, 2019. 6 pages.

Examination Report dated Dec. 12, 2022 in IN Patent Application No. 202248053111. 6 pages.

\* cited by examiner

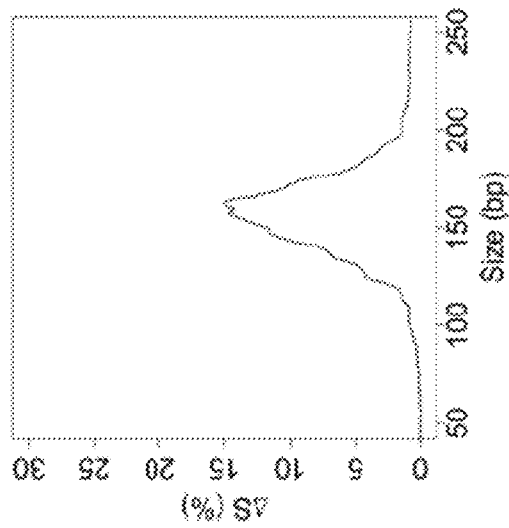
FIG. 24A
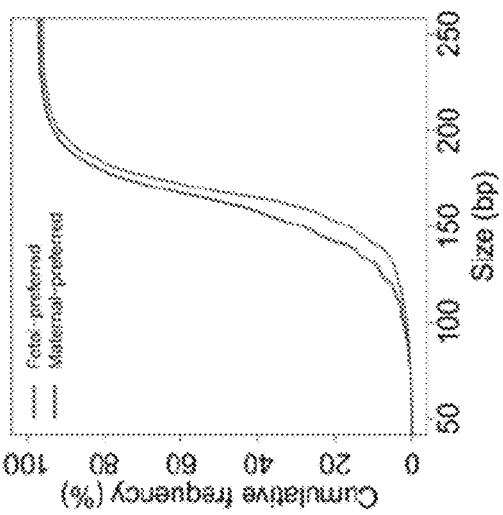
FIG. 24B
FIG. 24C
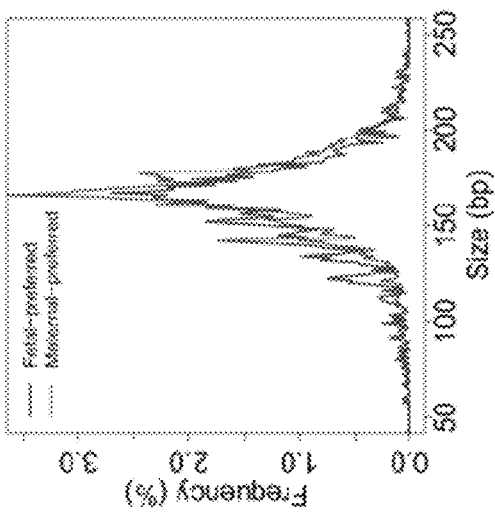
FIG. 24D
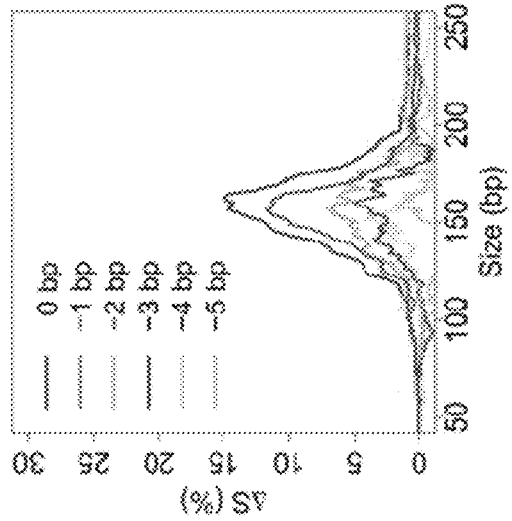
FIG. 24E
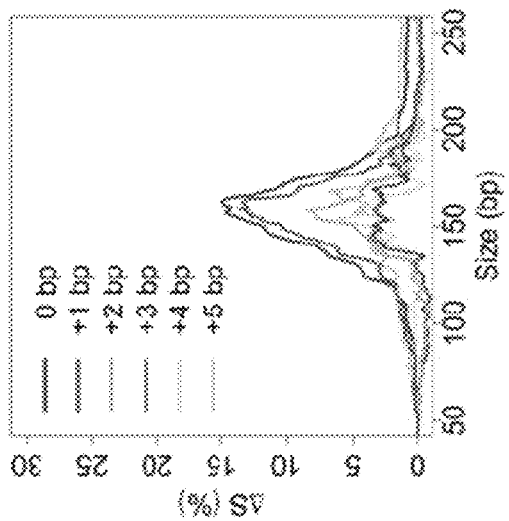

Preferred ending sites for plasma DNA fragments

ANALYSIS OF FRAGMENTATION PATTERNS OF CELL-FREE DNA

CROSS-REFERENCES TO RELATED APPLICATIONS

The present application is a divisional application of U.S. patent application Ser. No. 15/218,497 entitled "ANALYSIS OF FRAGMENTATION PATTERNS OF CELL-FREE DNA," filed on Jul. 25, 2016, which is a continuation-in-part of International Application No. PCT/CN2016/073753, filed on Feb. 14, 2016, and claims priority to and is a nonprovisional of U.S. Provisional Application No. 62/294,948, filed on Feb. 12, 2016, and 62/196,250, filed on Jul. 23, 2015, the entire contents of which are herein incorporated by reference for all purposes.

BACKGROUND

In previous studies, it was shown that plasma DNA mostly consists of short fragments of less than 200 bp (Lo et al. Sci Transl Med 2010; 2(61):61ra91). In the size distribution of plasma DNA, a peak could be observed at 166 bp. In addition, it was observed that the sequenced tag density would vary with a periodicity of around 180 bp close to transcriptional start sites (TSSs) when maternal plasma DNA was sequenced (Fan et al. PNAS 2008; 105:16266-71). These results are one set of evidence that the fragmentation of plasma DNA may not be a random process. However, the precise patterns of DNA fragmentation in plasma, as well as the factors governing the patterns, have not been clear. Further, practical applications of using the DNA fragmentation have not been fully realized.

BRIEF SUMMARY

Various embodiments are directed to applications (e.g., diagnostic applications) of the analysis of the fragmentation patterns of cell-free DNA, e.g., plasma DNA and serum DNA. Embodiments of one application can determine a classification of a proportional contribution of a particular tissue type in a mixture of cell-free DNA from different tissue types. For example, specific percentages, range of percentages, or whether the proportional contribution is above a specified percentage can be determined as a classification. In one example, preferred ending positions for the particular tissue type can be identified, and a relative abundance of cell-free DNA molecules ending on the preferred ending positions can be used to provide the classification of the proportional contribution. In another example, an amplitude in a fragmentation pattern (e.g., number of cell-free DNA molecules ending at a genomic position) in a region specific to the particular tissue type can be used.

Embodiments of another application can determine a genotype of a particular tissue type in a mixture of cell-free DNA from different tissue types. In one example, preferred ending positions for the particular tissue type can be identified, and the genotype can be determined using cell-free DNA molecules ending on the preferred ending positions.

Embodiments of another application can identify preferred ending positions by comparing a local maximum for left ends of cell-free DNA molecules to a local maximum for right ends of cell-free DNA molecules. Preferred ending positions can be identified when corresponding local maximum are sufficiently separated. Further, amounts of cell-free DNA molecules ending on a local maximum for left/right end can be compared to an amount of cell-free DNA molecules for a local maximum with low separation to determine a proportional contribution of a tissue type.

Other embodiments are directed to systems, portable consumer devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIGS. 24A-24E show data regarding plasma DNA size distributions in a pooled plasma DNA sample from 26 first trimester pregnant women for fragments ending on the fetal-preferred ending positions and fragments ending on the maternal-preferred ending positions.

TERMS

Figure 1:
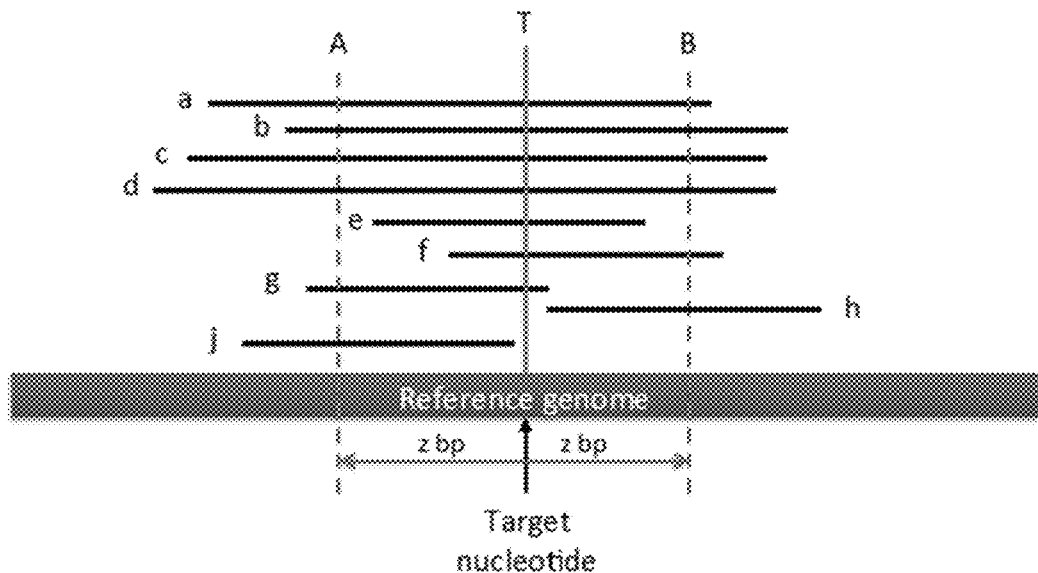
FIG. 1 shows an illustrative example for the definition of intact probability ($P_I$) according to embodiments of the present invention.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (mother vs. fetus) or to healthy cells vs. tumor cells.

A "biological sample" refers to any sample that is taken from a subject (e.g., a human, such as a pregnant woman, a person with cancer, or a person suspected of having cancer, an organ transplant recipient or a subject suspected of having a disease process involving an organ (e.g., the heart in myocardial infarction, or the brain in stroke, or the hematopoietic system in anemia) and contains one or more nucleic acid molecule(s) of interest. The biological sample can be a bodily fluid, such as blood, plasma, serum, urine, vaginal fluid, fluid from a hydrocele (e.g. of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g. thyroid, breast), etc. Stool samples can also be used. In various embodiments, the majority of DNA in a biological sample that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at for example, 30,000 g for another 10 minutes to remove residual cells.

"Cancer-associated changes" or "cancer-specific changes" include, but are not limited to, cancer-derived mutations (including single nucleotide mutations, deletions or insertions of nucleotides, deletions of genetic or chromosomal segments, translocations, inversions), amplification of genes, genetic segments or chromosomal segments, virus-associated sequences (e.g. viral episomes and viral insertions), aberrant methylation profiles or tumor-specific methylation signatures, aberrant cell-free DNA size profiles, aberrant histone modification marks and other epigenetic modifications, and locations of the ends of cell-free DNA fragments that are cancer-associated or cancer-specific.

An "informative cancer DNA fragment" corresponds to a DNA fragment bearing or carrying any one or more of the cancer-associated or cancer-specific change or mutation. An "informative fetal DNA fragment" corresponds to a fetal DNA fragment carrying a mutation not found in either of the genomes of the parents. An "informative DNA fragment" can refer to either of the above types of DNA fragments.

A "sequence read" refers to a string of nucleotides sequenced from any part or all of a nucleic acid molecule. For example, a sequence read may be a short string of nucleotides (e.g., 20-150) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

An "ending position" or "end position" (or just "end") can refer to the genomic coordinate or genomic identity or nucleotide identity of the outermost base, i.e. at the extremities, of a cell-free DNA molecule, e.g. plasma DNA molecule. The end position can correspond to either end of a DNA molecule. In this manner, if one refers to a start and end of a DNA molecule, both would correspond to an ending position. In practice, one end position is the genomic coordinate or the nucleotide identity of the outermost base on one extremity of a cell-free DNA molecule that is detected or determined by an analytical method, such as but not limited to massively parallel sequencing or next-generation sequencing, single molecule sequencing, double- or single-stranded DNA sequencing library preparation protocols, polymerase chain reaction (PCR), or microarray. Such in vitro techniques may alter the true in vivo physical end(s) of the cell-free DNA molecules. Thus, each detectable end may represent the biologically true end or the end is one or more nucleotides inwards or one or more nucleotides extended from the original end of the molecule e.g. 5' blunting and 3' filling of overhangs of non-blunt-ended double stranded DNA molecules by the Klenow fragment. The genomic identity or genomic coordinate of the end position could be derived from results of alignment of sequence reads to a human reference genome, e.g. hg19. It could be derived from a catalog of indices or codes that represent the original coordinates of the human genome. It could refer to a position or nucleotide identity on a cell-free DNA molecule that is read by but not limited to target-specific probes, mini-sequencing, DNA amplification.

A "preferred end" (or "recurrent ending position") refers to an end that is more highly represented or prevalent (e.g., as measured by a rate) in a biological sample having a physiological (e.g. pregnancy) or pathological (disease) state (e.g. cancer) than a biological sample not having such a state or than at different time points or stages of the same pathological or physiological state, e.g., before or after treatment. A preferred end therefore has an increased likelihood or probability for being detected in the relevant physiological or pathological state relative to other states. The increased probability can be compared between the pathological state and a non-pathological state, for example in patients with and without a cancer and quantified as likelihood ratio or relative probability. The likelihood ratio can be determined based on the probability of detecting at least a threshold number of preferred ends in the tested sample or based on the probability of detecting the preferred ends in patients with such a condition than patients without such a condition. Examples for the thresholds of likelihood ratios include but not limited to 1.1, 1.2, 1.3, 1.4, 1.5, 1.6, 1.8, 2.0, 2.5, 3.0, 3.5, 4.0, 4.5, 5, 6, 8, 10, 20, 40, 60, 80 and 100. Such likelihood ratios can be measured by comparing relative abundance values of samples with and without the relevant state. Because the probability of detecting a preferred end in a relevant physiological or disease state is higher, such preferred ending positions would be seen in more than one individual with that same physiological or disease state. With the increased probability, more than one cell-free DNA molecule can be detected as ending on a same preferred ending position, even when the number of cell-free DNA molecules analyzed is far less than the size of the genome. Thus, the preferred or recurrent ending positions are also referred to as the "frequent ending positions." In some embodiments, a quantitative threshold may be used to require that ends be detected at least multiple times (e.g., 3, 4, 5, 6, 7, 8, 9, 10, 15, 20, or 50) within the same sample or same sample aliquot to be considered as a preferred end. A relevant physiological state may include a state when a person is healthy, disease-free, or free from a disease of interest. Similarly, a "preferred ending window" corresponds to a contiguous set of preferred ending positions.

A "rate" of DNA molecules ending on a position relates to how frequently a DNA molecule ends on the position. The rate may be may be based on a number of DNA molecules that end on the position normalized against a number of DNA molecules analyzed. Accordingly, the rate corresponds to a frequency of how many DNA molecules end on a position, and does not relate to a periodicity of positions having a local maximum in the number of DNA molecules ending on the position.

A "calibration sample" can correspond to a biological sample whose tissue-specific DNA fraction is known or determined via a calibration method, e.g., using an allele specific to the tissue. As another example, a calibration sample can correspond to a sample from which preferred ending positions can be determined. A calibration sample can be used for both purposes.

A "calibration data point" includes a "calibration value" and a measured or known proportional distribution of the DNA of interest (i.e., DNA of particular tissue type). The calibration value can be a relative abundance as determined for a calibration sample, for which the proportional distribution of the tissue type is known. The calibration data points may be defined in a variety of ways, e.g., as discrete points or as a calibration function (also called a calibration curve or calibration surface). The calibration function could be derived from additional mathematical transformation of the calibration data points.

The term "sequencing depth" refers to the number of times a locus is covered by a sequence read aligned to the locus. The locus could be as small as a nucleotide, or as large as a chromosome arm, or as large as the entire genome. Sequencing depth can be expressed as 50x, 100x, etc., where "x" refers to the number of times a locus is covered with a sequence read. Sequencing depth can also be applied to multiple loci, or the whole genome, in which case x can refer to the mean number of times the loci or the haploid genome, or the whole genome, respectively, is sequenced. Ultra-deep sequencing can refer to at least 100× in sequencing depth.

A "separation value" corresponds to a difference or a ratio involving two values. The separation value could be a simple difference or ratio. As examples, a direct ratio of x/y is a separation value, as well as x/(x+y). The separation value can include other factors, e.g., multiplicative factors. As other examples, a difference or ratio of functions of the values can be used, e.g., a difference or ratio of the natural logarithms (ln) of the two values. A separation value can include a difference and a ratio.

A "relative abundance" is a type of separation value that relates an amount (one value) of cell-free DNA molecules ending within one window of genomic position to an amount (other value) of cell-free DNA molecules ending within another window of genomic positions. The two windows may overlap, but would be of different sizes. In other implementations, the two windows would not overlap. Further, the windows may be of a width of one nucleotide, and therefore be equivalent to one genomic position.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1). The terms "cutoff" and "threshold" refer to predetermined numbers used in an operation. For example, a cutoff size can refer to a size above which fragments are excluded. A threshold value may be a value above or below which a particular classification applies. Either of these terms can be used in either of these contexts.

The term "level of cancer" can refer to whether cancer exists (i.e., presence or absence), a stage of a cancer, a size of tumor, whether there is metastasis, the total tumor burden of the body, and/or other measure of a severity of a cancer (e.g. recurrence of cancer). The level of cancer could be a number or other indicia, such as symbols, alphabet letters, and colors. The level could be zero. The level of cancer also includes premalignant or precancerous conditions (states) associated with mutations or a number of mutations. The level of cancer can be used in various ways. For example, screening can check if cancer is present in someone who is not known previously to have cancer. Assessment can investigate someone who has been diagnosed with cancer to monitor the progress of cancer over time, study the effectiveness of therapies or to determine the prognosis. In one embodiment, the prognosis can be expressed as the chance of a patient dying of cancer, or the chance of the cancer progressing after a specific duration or time, or the chance of cancer metastasizing. Detection can mean 'screening' or can mean checking if someone, with suggestive features of cancer (e.g. symptoms or other positive tests), has cancer.

A "local maximum" can refer to a genomic position (e.g., a nucleotide) at which the largest value of the parameter of interest is obtained when compared with the neighboring positions or refer to the value of the parameter of interest at such a genomic position. As examples, the neighboring positions can range from 50 bp to 2000 bp. Examples for the parameter of interest include, but are not limited to, the number of fragments ending on a genomic position, the number of fragments overlapping with the position, or the proportion of fragments covering the genomic position that are larger than a threshold size. Many local maxima can occur when the parameter of interest has a periodic structure. A global maximum is a specific one of the local maxima. Similarly, a "local minimum" can refer to a genomic position at which the smallest value of the parameter of interest is obtained when compared with the neighboring positions or refer to the value of the parameter of interest at such a genomic position.

DETAILED DESCRIPTION

Factors affecting the fragmentation pattern of cell-free DNA (e.g., plasma DNA) and the applications, including those in molecular diagnostics, of the analysis of cell-free DNA fragmentation patterns are described. Various applications can use a property of a fragmentation pattern to determine a proportional contribution of a particular tissue type, to determine a genotype of a particular tissue type (e.g., fetal tissue in a maternal sample or tumor tissue in a sample from a cancer patient), and/or to identify preferred ending positions for a particular tissue type, which may then be used to determine a proportional contribution of a particular tissue type. In some embodiments, the preferred ending positions for a particular tissue can also be used to measure the absolute contribution of a particular tissue type in a sample, e.g. in number of genomes per unit volume (e.g. per milliliter).

Examples of a classification of a proportional contribution include specific percentages, range of percentage, or whether the proportional contribution is above a specified percentage can be determined as a classification. For determining the classification of a proportional contribution, some embodiments can identify preferred ending positions corresponding to a particular tissue type (e.g., fetal tissue or tumor tissue). Such preferred ending positions can be determined in various ways, e.g., by analyzing a rate at which cell-free DNA molecules end on genomic positions, comparisons such rates to other samples (e.g., not having a relevant condition), and comparisons of sets of genomic positions with high occurrence rates of ends of cell-free DNA molecules for different tissues and/or different samples differing in a condition. A relative abundance of cell-free DNA molecules ending at the preferred ending positions relative to cell-free DNA molecules ending at other genomic positions can be compared to one or more calibration values determined from one or more calibration biological samples whose proportional contribution of the particular tissue type are known. Data provided herein shows a positive relationship between various measures of relative abundance and a proportional contribution of various tissues in a sample.

For determining the classification of a proportional contribution, some embodiments can use an amplitude in a fragmentation pattern (e.g., number of cell-free DNA molecules ending at a genomic position). For example, one or more local minima and one or more local maxima can be identified by analyzing the numbers of cell-free DNA molecules that end at a plurality of genomic positions. A separation value (e.g., a ratio) of a first number of cell-free DNA molecules at one or more local maxima and a second number of cell-free DNA molecules at one or more local minima is shown to be positively related to a proportional contribution of the particular tissue type.

In some embodiments, a concentration of the tissue of interest could be measured in relation to the volume or weight of the cell-free DNA samples. For example, quantitative PCR could be used to measure the number of cell-free DNA molecules ending at one or more preferred ends in a unit volume or unit weight of the extracted cell-free DNA sample. Similar measurements can be made for calibration samples, and thus the proportional contribution can be determined as a proportional contribution, as the contribution is a concentration per unit volume or unit weight.

For determining a genotype of a particular tissue type (e.g., fetal tissue or tumor tissue) in a mixture of cell-free DNA from different tissue types, some embodiments can identify a preferred ending position for the particular tissue type. For each cell-free DNA molecule of a set of cell-free DNA molecules ending on the preferred ending position, a corresponding base occurring at the preferred ending position can be determined. The corresponding bases can be used to determine the genotype at the preferred ending position, e.g., based on percentages of different bases seen. In various implementations, a high percentage of just one base (e.g., above 90%) can indicate the genotype is homozygous for the base, while two bases having similar percentages (e.g., between 30-70%) can lead to a determination of the genotype being heterozygous.

To identify preferred ending positions, some embodiments can compare a local maximum for left ends of cell-free DNA molecules to a local maximum for right ends of cell-free DNA molecules. Preferred ending positions can be identified when corresponding local maximum are sufficiently separated. Further, amounts of cell-free DNA molecules ending on a local maximum for left/right end can be compared to an amount of cell-free DNA molecules for a local maximum with low separation to determine a proportional contribution of a tissue type.

In the description below, an overview of fragmentation and techniques is first described, followed by specifics of fragmentation patterns and examples of quantification thereof, and further description relating to determining a proportional contribution, identifying preferred ending positions, and determining a genotype.

I. Overview of Fragmentation and Techniques

In this disclosure, we show that there exists a non-random fragmentation process of cell-free DNA. The non-random fragmentation process takes place to some extent in various types of biological samples that contain cell-free DNA, e.g. plasma, serum, urine, saliva, cerebrospinal fluid, pleural fluid, amniotic fluid, peritoneal fluid, and ascitic fluid. Cell-free DNA occurs naturally in the form of short fragments. Cell-free DNA fragmentation refers to the process whereby high molecular weight DNA (such as DNA in the nucleus of a cell) are cleaved, broken, or digested to short fragments when cell-free DNA molecules are generated or released.

Not all cell-free DNA molecules are of the same length. Some molecules are shorter than others. It has been shown that cell-free DNA, such as plasma DNA, is generally shorter and less intact, namely of poor intact probability, or poorer integrity, within open chromatin domains, including around transcription start sites, and at locations between nucleosomal cores, such as at the linker positions (Straver et al Prenat Diagn 2016, 36:614-621). Each different tissue has its characteristic gene expression profile which in turn is regulated by means including chromatin structure and nucleosomal positioning. Thus, cell-free DNA patterns of intact probability or integrity at certain genomic locations, such as that of plasma DNA, are signatures or hallmarks of the tissue origin of those DNA molecules. Similarly, when a disease process, e.g. cancer, alters the gene expression profile and function of the genome of a cell, the cell-free DNA intact probability profile derived from the cells with disease would be reflective of those cells. The cell-free DNA profile, hence, would provide evidence for or are hallmarks of the presence of the disease.

Some embodiments further enhance the resolution for studying the profile of cell-free DNA fragmentation. Instead of just summating reads over a stretch of nucleotides to identify regions with higher or lower intact probability or integrity, we studied the actual ending positions or termini of individual cell-free DNA molecules, especially plasma DNA molecules. Remarkably, our data reveal that the specific locations of where cell-free DNA molecules are cut are non-random. High molecular weight genomic tissue DNA that are sheared or sonicated in vitro show DNA molecules with ending positions randomly scattered across the genome. However, there are certain ending positions of cell-free DNA molecules that are highly represented within a sample, such as plasma. The number of occurrence or representation of such ending positions is statistically significantly higher than expected by chance alone. These data bring our understanding of cell-free DNA fragmentation one step beyond that of regional variation of integrity (Snyder et al Cell 2016, 164: 57-68). Here we show that the process of cell-free DNA fragmentation is orchestrated even down to the specific nucleotide position of cutting or cleavage. We termed these non-random positions of cell-free DNA ending positions as the preferred ending positions or preferred ends.

In the present disclosure, we show that there are cell-free DNA ending positions that commonly occur across individuals of different physiological states or disease states. For example, there are common preferred ends shared by pregnant and non-pregnant individuals, shared by a pregnant and a cancer patient, shared with individuals with and without cancer. On the other hand, there are preferred ends that mostly occur only in pregnant women, only in cancer patients, or only in non-pregnant individuals without cancer. Interestingly, these pregnancy-specific or cancer-specific or disease-specific ends are also highly represented in other individuals with comparable physiological or disease state. For example, preferred ends identified in the plasma of one pregnant woman are detectable in plasma of other pregnant women. Furthermore, the quantity of a proportion of such preferred ends correlated with the fetal DNA fraction in plasma of other pregnant women. Such preferred ends are indeed associated with the pregnancy or the fetus because their quantities are reduced substantially in the post-delivery maternal plasma samples. Similarly, in cancer, preferred ends identified in the plasma of one cancer patient are detectable in plasma of another cancer patient. Furthermore, the quantity of a proportion of such preferred ends correlated with the tumor DNA fraction in plasma of other cancer patients. Such preferred ends are associated with cancer because their quantities are reduced following treatment of cancer, e.g. surgical resection.

There are a number of applications or utilities for the analysis of cell-free DNA preferred ends. They could provide information about the fetal DNA fraction in pregnancy and hence the health of the fetus. For example, a number of pregnancy-associated disorders, such as preeclampsia, preterm labor, intrauterine growth restriction (IUGR), fetal chromosomal aneuploidies and others, have been reported to be associated with perturbations in the fractional concentration of fetal DNA, namely fetal DNA fraction, or fetal fraction, compared with gestational age matched control pregnancies. The cell-free plasma DNA preferred ends associated with cancer reveals the tumor DNA fraction or fractional concentration in a plasma sample. Knowing the tumor DNA fraction provides information about the stage of cancer, prognosis and aid in monitoring for treatment efficacy or cancer recurrence. The profile of cell-free DNA preferred ends would also reveal the composition of tissues contributing DNA into the biological sample containing cell-free DNA, e.g. plasma. One may therefore be able to identify the tissue origin of cancer or other pathologies, e.g. cerebrovascular accidents (i.e. stroke), organ manifestations of systemic lupus erythematosus.

A catalog of preferred ends relevant to particular physiological states or pathological states can be identified by comparing the cell-free DNA profiles of preferred ends among individuals with different physiological or pathological states, e.g. non-pregnant compared with pregnant samples, cancer compared with non-cancer samples, or profile of pregnant woman without cancer compared with profile of non-pregnant cancer patients. Another approach is to compare the cell-free DNA profiles of preferred ends at different time of a physiological (e.g. pregnancy) or pathological (e.g. cancer) process. Examples of such time points include before and after pregnancy, before and after delivery of a fetus, samples collected across different gestational ages during pregnancy, before and after treatment of cancer (e.g. targeted therapy, immunotherapy, chemotherapy, surgery), different time points following the diagnosis of cancer, before and after progression of cancer, before and after development of metastasis, before and after increased severity of disease, or before and after development of complications.

In addition, the preferred ends could be identified using genetic markers that are relevant for a particular tissue. For example, cell-free DNA molecules containing a fetal-specific SNP allele would be useful for identifying fetal-specific preferred ends in a sample such as maternal plasma. Vice versa, plasma DNA molecules containing a maternal-specific SNP allele would be useful for identifying maternal-specific preferred ends in maternal plasma. Plasma DNA molecules containing a tumor-specific mutation could be used to identify preferred ends associated with cancer. Plasma DNA molecules containing either a donor or recipient-specific SNP allele in the context of organ transplantation are useful for identifying preferred ends of the transplanted or non-transplanted organ. For example, the SNP alleles specific to the donor would be useful for identifying preferred ends representative of the transplanted organ.

A preferred end can be considered relevant for a physiological or disease state when it has a high likelihood or probability for being detected in that physiological or pathological state. In other embodiments, a preferred end is of a certain probability more likely to be detected in the relevant physiological or pathological state than in other states. Because the probability of detecting a preferred end in a relevant physiological or disease state is higher, such preferred or recurrent ends (or ending positions) would be seen in more than one individual with that same physiological or disease state. The high probability would also render such preferred or recurrent ends to be detectable many times in the same cell-free DNA sample or aliquot of the same individual. In some embodiments, a quantitative threshold may be set to limit the inclusion of ends that are detected at least a specified number of times (e.g., 5, 10, 15, 20, etc.) within the same sample or same sample aliquot to be considered as a preferred end.

After a catalog of cell-free DNA preferred ends is established for any physiological or pathological state, targeted or non-targeted methods could be used to detect their presence in cell-free DNA samples, e.g. plasma, or other individuals to determine a classification of the other tested individuals having a similar health, physiologic or disease state. The cell-free DNA preferred ends could be detected by random non-targeted sequencing. The sequencing depth would need to be considered so that a reasonable probability of identifying all or a portion of the relevant preferred ends could be achieved. Alternatively, hybridization capture of loci with high density of preferred ends could be performed on the cell-free DNA samples to enrich the sample with cell-free DNA molecules with such preferred ends following but not limited to detection by sequencing, microarray, or the PCR. Yet, alternatively, amplification based approaches could be used to specifically amplify and enrich for the cell-free DNA molecules with the preferred ends, e.g. inverse PCR, rolling circle amplification. The amplification products could be identified by sequencing, microarray, fluorescent probes, gel electrophoresis and other standard approaches known to those skilled in the art.

In practice, one end position can be the genomic coordinate or the nucleotide identity of the outermost base on one extremity of a cell-free DNA molecule that is detected or determined by an analytical method, such as but not limited to massively parallel sequencing or next-generation sequencing, single molecule sequencing, double- or single-stranded DNA sequencing library preparation protocols, PCR, other enzymatic methods for DNA amplification (e.g. isothermal amplification) or microarray. Such in vitro techniques may alter the true in vivo physical end(s) of the cell-free DNA molecules. Thus, each detectable end may represent the biologically true end or the end is one or more nucleotides inwards or one or more nucleotides extended from the original end of the molecule. For example, the Klenow fragment is used to create blunt-ended double-stranded DNA molecules during DNA sequencing library construction by blunting of the 5' overhangs and filling in of the 3' overhangs. Though such procedures may reveal a cell-free DNA end position that is not identical to the biological end, clinical relevance could still be established. This is because the identification of the preferred being relevant or associated with a particular physiological or pathological state could be based on the same laboratory protocols or methodological principles that would result in consistent and reproducible alterations to the cell-free DNA ends in both the calibration sample(s) and the test sample(s). A number of DNA sequencing protocols use single-stranded DNA libraries (Snyder et al Cell 2016, 164: 57-68). The ends of the sequence reads of single-stranded libraries may be more inward or extended further than the ends of double-stranded DNA libraries.

The genome identity or genomic coordinate of the end position could be derived from results of alignment of sequence reads to a human reference genome, e.g. hg19. It could be derived from a catalog of indices or codes that represent the original coordinates of the human genome. While an end is the nucleotide at one or both extremities of a cell-free DNA molecule, the detection of the end could be done through the recognition of other nucleotide or other stretches of nucleotides on the plasma DNA molecule. For example, the positive amplification of a plasma DNA molecule with a preferred end detected via a fluorescent probe that binds to the middle bases of the amplicon. For instance, an end could be identified by the positive hybridization of a fluorescent probe that binds to some bases on a middle section of a plasma DNA molecule, where the fragment size known. In this way, one could determine the genomic identity or genomic coordinate of an end by working out how many bases are external to the fluorescent probe with known sequence and genomic identity. In other words, an end could be identified or detected through the detection of other bases on the same plasma DNA molecule. An end could be a position or nucleotide identity on a cell-free DNA molecule that is read by but not limited to target-specific probes, mini-sequencing, and DNA amplification.

II. Fragmentation Patterns of Plasma DNA

For the analysis of the fragmentation pattern of maternal plasma DNA, we sequenced the plasma DNA from a pregnant woman recruited from the Department of Obstetrics and Gynaecology at a gestational age of 12 weeks (Lo et al. Sci Transl Med 2010; 2(61):61ra91). Plasma DNA obtained from the mother was subjected to massively parallel sequencing using the Illumina Genome Analyzer platform. Other massively parallel or single molecule sequencers could be used. Paired-end sequencing of the plasma DNA molecules was performed. Each molecule was sequenced at each end for 50 bp, thus totaling 100 bp per molecule. The two ends of each sequence were aligned to the reference human genome (Hg18 NCBI.36) using the SOAP2 program (Li R et al. Bioinformatics 2009, 25:1966-7). DNA was also extracted from the buffy coat samples of the father and mother, and the CVS sample. These DNA samples were genotyped using the Affymetrix Genome-Wide Human SNP Array 6.0 system.

A. Example Quantifying of Fragmentation

To reflect the fragmentation patterns, intact probability ($P_I$) can be determined for each nucleotide for the genome based on the sequencing results of the maternal plasma DNA.

$$P_I = \frac{N_z}{N_T}$$

where $N_z$ is the number of full length sequenced reads covering at least z nucleotides (nt) on both sides (5' and 3') of the target nucleotide; and $N_T$ is the total number of sequenced reads covering the target nucleotide.

The value of $P_I$ can reflect the probability of having an intact DNA molecule centered at a particular position with a length of twice the value of z plus 1 (2z+1). The higher the value of intact probability ($P_I$), the less likely is the plasma DNA being fragmented at the particular nucleotide position. To further illustrate this, the definition of intact probability is illustrated in FIG. 1.

FIG. 1 shows an illustrative example for the definition of intact probability ($P_I$). T is the position of the target nucleotide at which $P_I$ is calculated for. A and B are two positions at z nucleotides (nt) upstream (5') and z nt downstream (3') of T, respectively. The black lines labeled from a to j represent sequenced plasma DNA fragments from the maternal plasma. Fragments a to d cover all the three positions A, B and T. Therefore, the number of fragments covering at least z nt on both sides (5' and 3') of the target nucleotide ($N_z$) is 4. In addition, fragments e, f and g also cover the position T, but they do not cover both positions A and B. Therefore, there are a total of 7 fragments covering position T ($N_T$=7). Fragments h and j cover either A or B but not T. These fragments are not counted in $N_z$ or $N_T$. Therefore, the $P_I$ in this particular example is 4/7 (57%).

In one embodiment, $P_I$ can be calculated using 25 as the value of z. Thus, the intact plasma DNA fragments would be defined as fragments covering at least 25 nt upstream of the target position to 25 nt downstream of the target position. In other embodiments, other values of z can be used, for example, but not limited to, 10, 15, 20, 30, 35, 40, 45, 50, 55, 60, 65, 70, 75 and 80.

$P_I$ is an example of a relative abundance of cell-free DNA molecules ending within a window of genomic positions. Other metrics can be used, e.g., the reciprocal of $P_I$, which would have an opposite relationship with the probability of having an intact DNA molecule. A higher value of the reciprocal of $P_I$ would indicate a higher probability of being an ending position or an ending window. Other examples are a p-value for a measured number of ending DNA fragments vs. an expected number of ending DNA fragments, a proportion of DNA fragments ending out of all aligned DNA fragments, or a proportion of preferred end termination ratio (PETR), all of which are described in more detail below. All such metrics of a relative abundance measure a rate at which cell-free DNA fragments end within a window, e.g., with a width of 2z+1, where z can be zero, thereby causing the window to be equivalent to a genomic position.

B. Periodicity of Fragmentation Pattern

Certain regions of the genome are prone to a higher rate (frequency) of breakage of a chromosomal region in a particular tissue, and thus have a higher rate of cell-free DNA fragments ending within a window in the region. A plot of the relative abundance shows a fragmentation pattern, which can have a periodic structure. The periodic structure shows positions of maximum ending positions (high cleavage) and positions of minimum ending positions (low cleavage). When using $P_I$, a maximum value corresponds to a window of low cleavage, as $P_I$ measures an intact probability as opposed to a cleavage probability (ending position probability), which have an inverse relationship to each other.

Figures 2A, 2B:
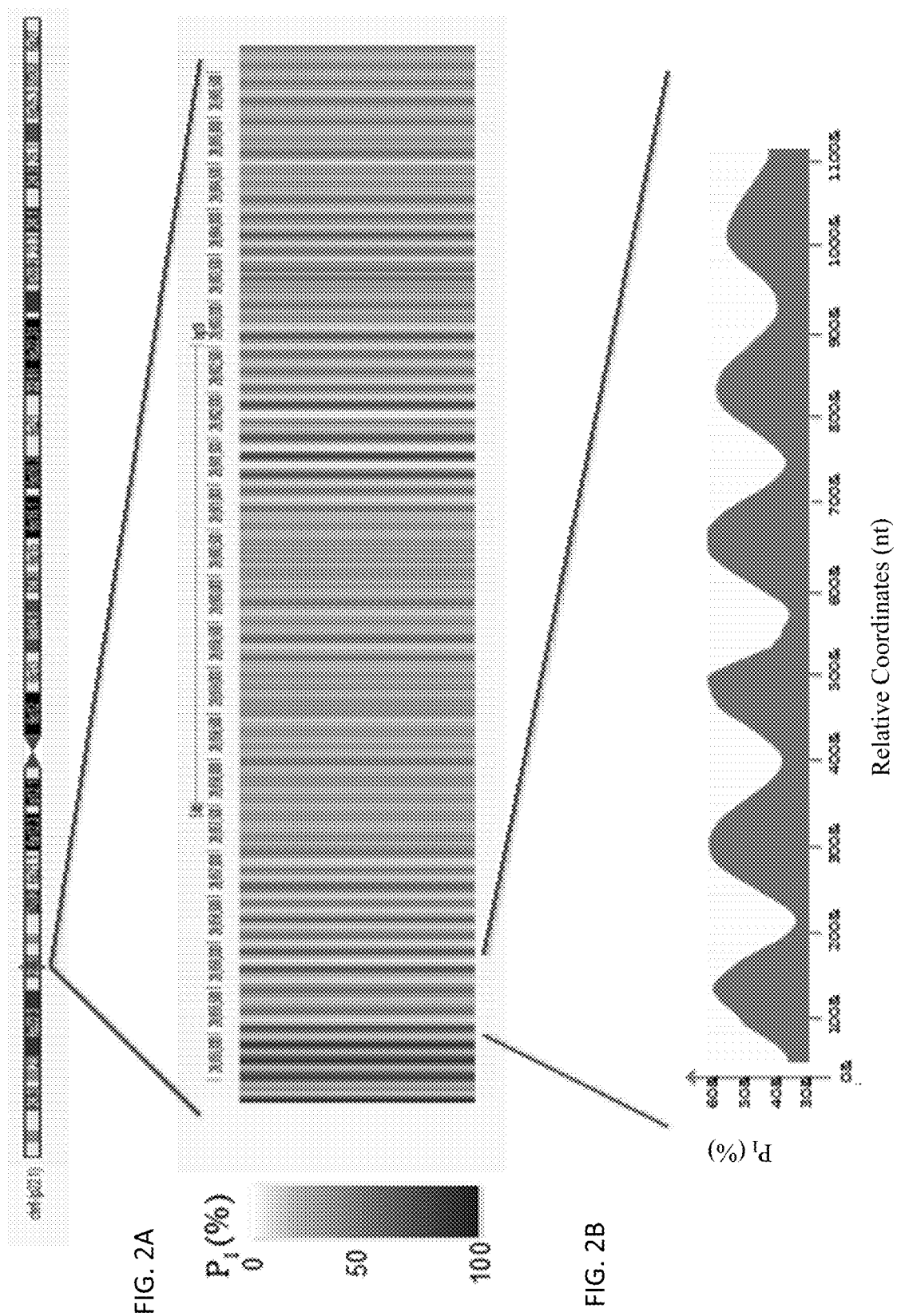
FIGS. 2A and 2B shows variation in $P_I$ across a segment on chromosome 6 using 25 as the value of z, according to embodiments of the present invention.

FIGS. 2A and 2B show variation in $P_I$ across a segment on chromosome 6 using 25 as the value of z, according to embodiments of the present invention. In FIG. 2A, the variation in $P_I$ is presented in different intensities of grey as shown in the key on the left side. In FIG. 2B, the variation in $P_I$ is visualized in a shorter segment. The x-axis is the genomic coordinate in nucleotides (nt) and the y-axis is the $P_I$. The variation in $P_I$ has an apparent periodicity of around 180 bp.

C. Synchronous Variation in $P_I$ for Maternal and Fetal DNA in Maternal Plasma

While $P_I$ varies across the genome with a periodicity of approximately 180 bp, we further investigated if the variation in $P_I$ would be synchronous for fetally and maternally derived plasma DNA molecules. Synchronous variation means that the peaks (maxima) and troughs (minima) of $P_I$ occur at the same relative nucleotide positions throughout the genome or at a sufficiently high proportion of the genome. The threshold for defining the sufficiently high proportion can be adjusted for specific applications, for example, but not limited to, >20%, >25%, >30%, >35%, >40%, >45%, >50%, >55%, >60%, >65%, >70%, >75%, >80%, >85%, >90% and >95%. The two figures below (FIG. 3 and FIG. 4) show two possible relationships between the variations in $P_I$ for the maternally and fetally-derived DNA in maternal plasma.

Figure 3:
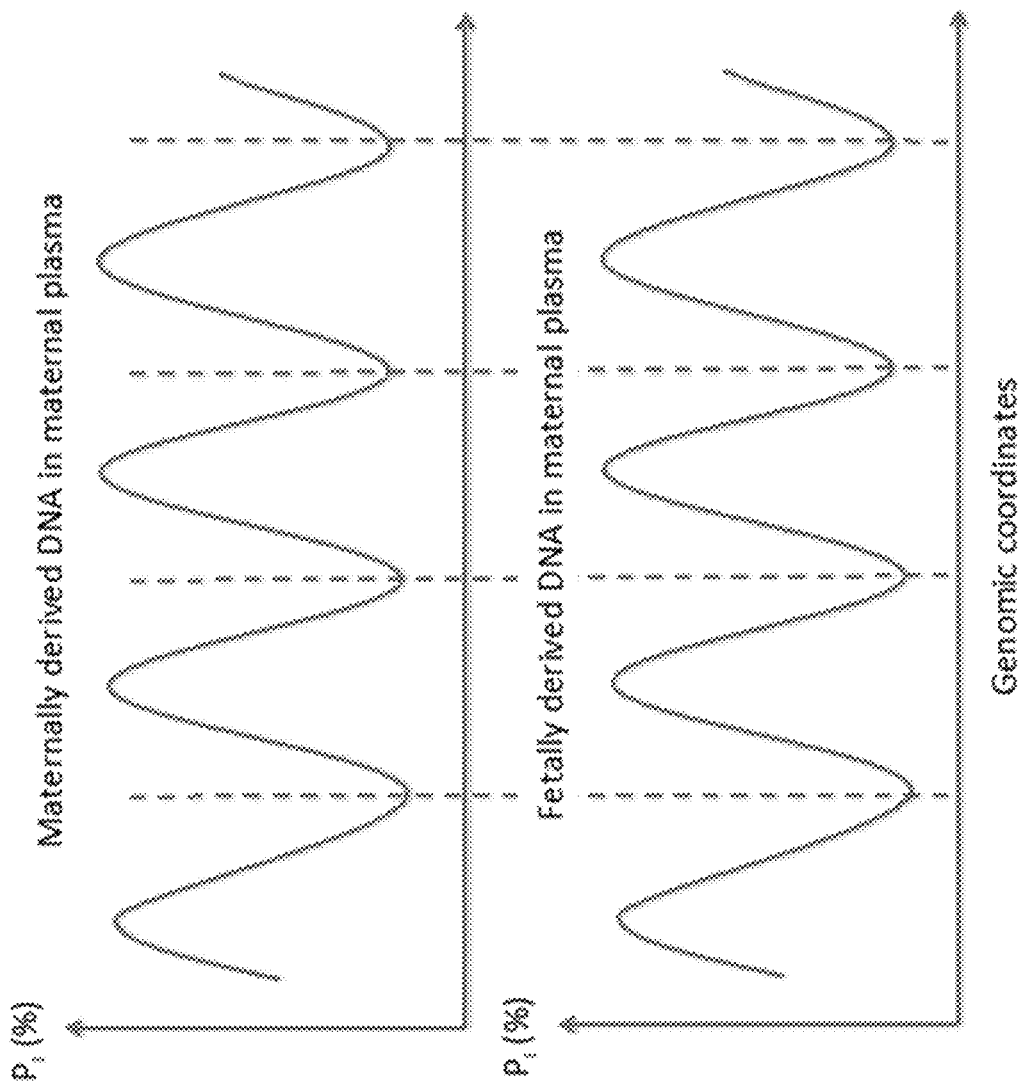
FIG. 3 shows the illustration of the synchronous variation of $P_I$ for maternally and fetally-derived DNA in maternal plasma.

FIG. 3 shows the illustration of the synchronous variation of $P_I$ for maternally and fetally-derived DNA in maternal plasma. The peaks and troughs of $P_I$ occur at the same relative positions for the maternal and fetal DNA across the genome or in most part of the genome. If there was synchronous variation in a region, then fetally-derived DNA and maternally-derived DNA would have the same fragmentation pattern, thereby hindering use of a periodicity of a fragmentation pattern in the region as a signature of one of the tissue types.

Figure 4:
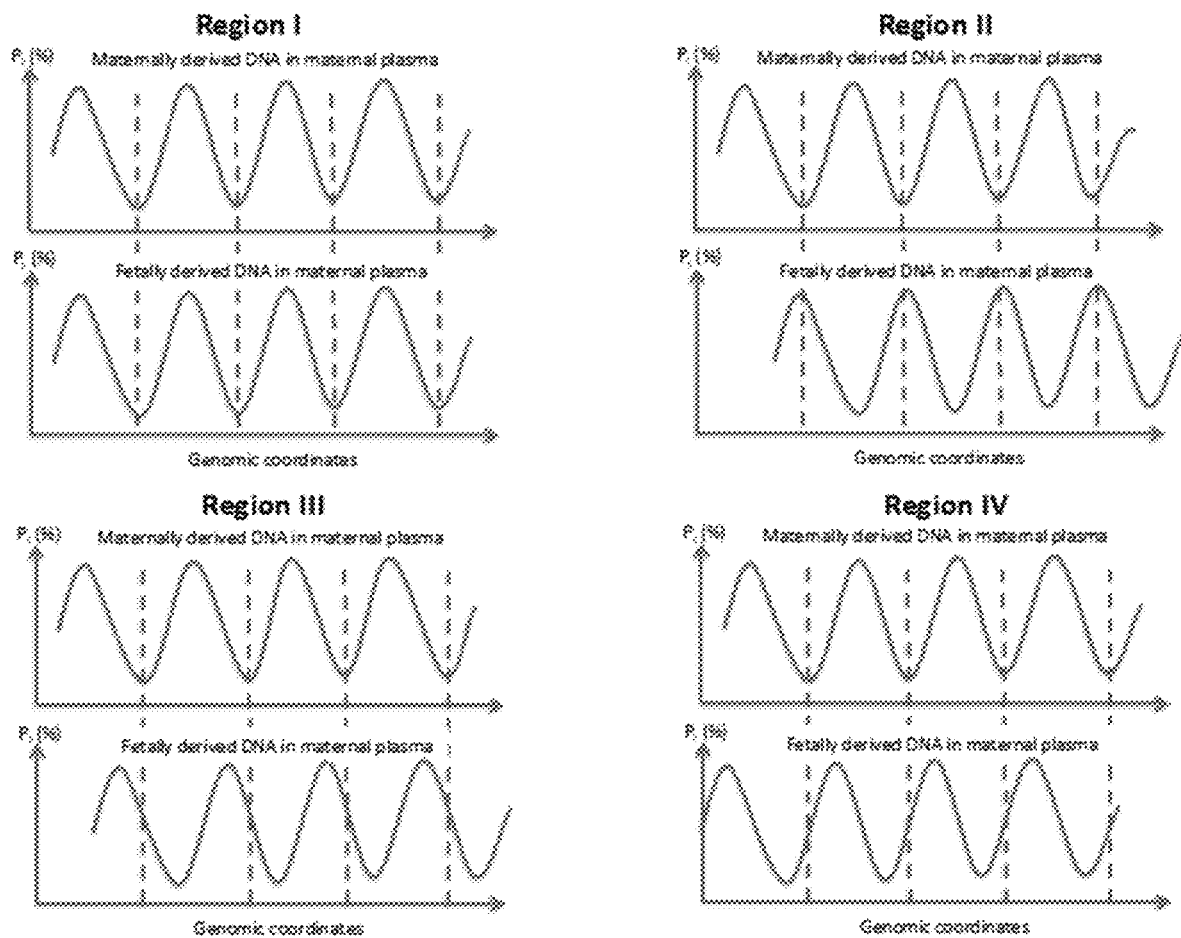
FIG. 4 shows an illustration of asynchronous variation of $P_I$ for maternally and fetally derived DNA in maternal plasma.

FIG. 4 shows an illustration of asynchronous variation of $P_I$ for maternally and fetally derived DNA in maternal plasma. The peaks and troughs for $P_I$ for maternal and fetal DNA do not have a constant relative relationship across the genome. At Region I, the peaks of $P_I$ for the maternal DNA coincide with the peak for the fetal DNA. At Region II, the peaks of $P_I$ for the maternal DNA coincide with the trough for the fetal DNA. At Regions III and IV, the peaks of $P_I$ for the maternal DNA are in-between the peaks and troughs of the fetal DNA. If the variation was not synchronous, such a difference in the fetal and maternal fragmentation patterns could be used as a signature to identify DNA that is likely from the fetus or the mother. Further, such a difference can be used to determine a proportional contribution of fetal or maternal tissue, as is described in more detail below. For example, DNA fragments ending at one of the peaks in region II is more likely fetal DNA, and the relative abundance of DNA fragments ending at such a peak compared to other genomic positions would increase with increasing fetal DNA fraction.

Figure 5:
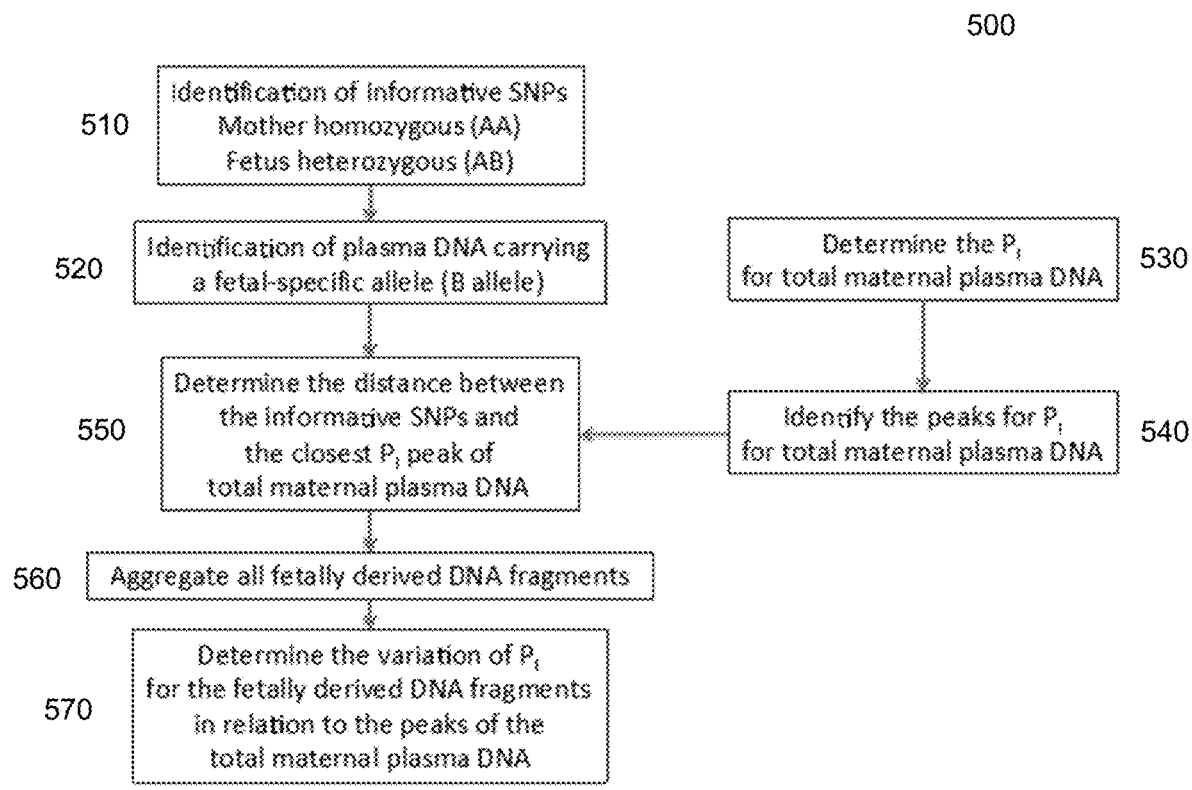
FIG. 5 is a flowchart showing an analysis on whether maternal and fetal DNA molecules are synchronous in the variation in $P_I$.

FIG. 5 is a flowchart showing an analysis 500 on whether maternal and fetal DNA molecules are synchronous in the variation in $P_I$. Analysis 500 investigates if the variation in PI is synchronous between maternally and fetally-derived DNA in maternal plasma. Analysis 500 can use a computer system. Although analysis 500 was performed using sequencing, as described above, other techniques may be used, e.g., as described herein.

At block 510, analysis 500 identifies SNPs where the pregnant woman is homozygous (AA) and the fetus is heterozygous (AB). These SNPs are termed informative SNPs. The B allele is the fetal-specific allele. Such informative SNPs can be identified by analyzing a maternal sample that is only or predominantly of maternal origin. For example, the buffy coat of a blood sample can be used, as the white blood cells would be predominantly from the mother. Genomic positions where only one nucleotide appears (or a high percentage of one nucleotide, e.g., above 80%, which may depend on the fetal DNA fraction) can be identified as being homozygous in the mother. The plasma can be analyzed to identify positions homozygous in the mother where a sufficient percentage of DNA fragments are identified that have another allele identified.

At block 520, plasma DNA molecules having the fetal-specific allele B were identified. These DNA molecules can be identified as corresponding to fetal tissue as a result of allele B being identified.

At block 530, the value of $P_I$ was determined for the cell-free DNA in the maternal plasma. These values for $P_I$ include fetal and maternal DNA. The value for $P_I$ for a given genomic position was obtained by analyzing the sequence reads aligned to that genomic position of a reference genome.

At block 540, the peaks for $P_I$ were determined by analyzing the output of block 530. The peaks can be identified in various ways, and each peak may be restricted to just one genomic position or allowed to correspond to more than one genomic position. We observed that $P_I$ varies across the whole genome for the mostly maternally-derived DNA in maternal plasma in a sinusoid-like pattern with a periodicity of approximately 180 bp.

At block 550, a distance between the informative SNPs and the closest $P_I$ (block 540) for the total maternal plasma were determined. We identified the position of the SNP relative to the nearest peak of $P_I$ variation for the total plasma DNA which was predominantly derived from the pregnant woman herself.

At block 560, all of the fetally-derived DNA fragments were aggregated. All the detected plasma DNA fragments carrying a fetal-specific allele were aggregated for the calculation of the $P_I$ for fetally-derived DNA. $P_I$ was then calculated for the aggregated fetally-derived DNA fragments with reference to the position of the nearest $P_I$ peak for the total maternal plasma DNA. The calculation of the $P_I$ for fetally-derived DNA was performed in a similar manner as the calculation of the $P_I$ for the total maternal plasma DNA.

At block 570, a variation of $P_I$ for the fetally-derived DNA fragments was determined in relation to the peaks in $P_I$ for the total maternal plasma DNA. The variation is shown in FIG. 6.

Figure 6:
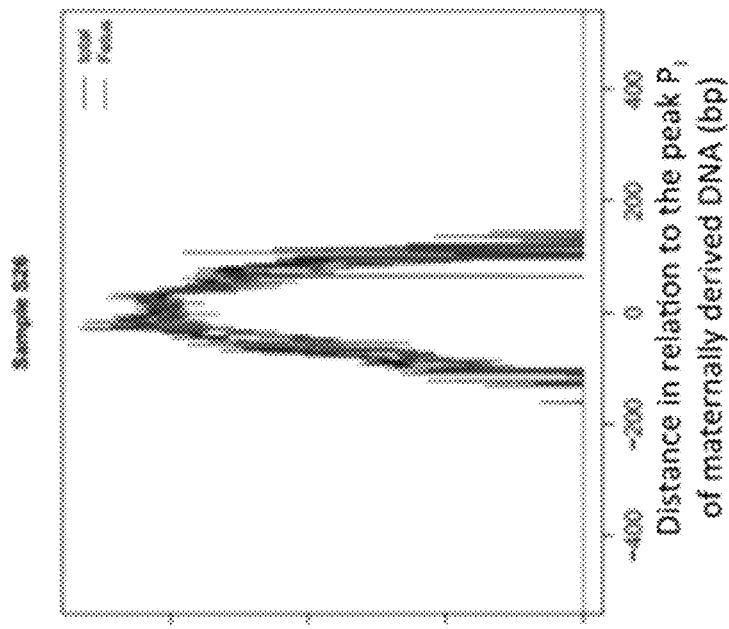
FIG. 6 shows an analysis of two maternal plasma samples (S24 and S26) for the variation of $P_I$ for maternally (red/grey) and fetally (blue/black) derived DNA fragments in maternal plasma.
Figure 6:
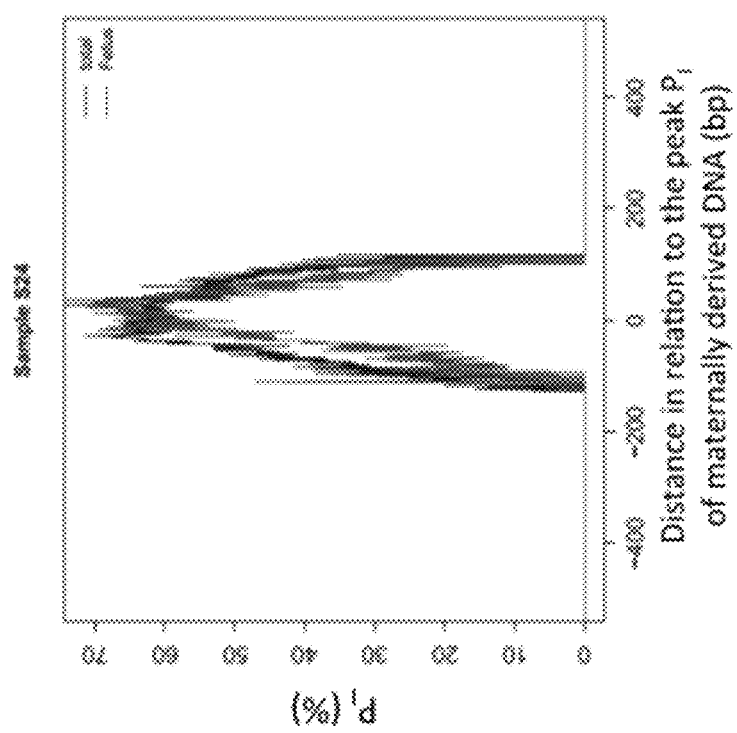

FIG. 6 shows an analysis of two maternal plasma samples (S24 and S26) for the variation of $P_I$ for fetally-derived (red/grey) and total (blue/black) DNA fragments in the maternal plasma samples. The vertical axis shows $P_I$ as a percentage. The horizontal axis shows the distance in base pairs (bp) between the informative SNP and the closest peak in $P_I$.

The total values include contributions from fetal and maternal DNA. The total values are aggregated across all peaks $P_I$. As can be seen, the closer the SNP is to the peak $P_I$ higher the value for $P_I$. In fact, for the fetal-derived DNA fragments, the peak $P_I$ was located at about position 0. Thus, the $P_I$ peaked at about the same position for the maternally and fetally-derived DNA fragments. From these data, we conclude that the variations of $P_I$ for maternally and fetally-derived DNA are synchronous.

Although the fragmentation patterns appear to be synchronous, the description below shows that other properties besides a periodicity can be used to distinguish the fragmentation patterns, thereby allowing a signature for a particular tissue type to be determined. For example, a difference in amplitude of the peaks and troughs for certain genomic regions has been found, thereby allowing certain positions within those regions to be used in determining a tissue-specific fragmentation pattern.

D. Factors Affecting the Variation of the Fragmentation Patterns of Plasma DNA

In previous studies, it was shown that the fragmentation of plasma DNA was not random close to the TSS (Fan et al. PNAS 2008; 105:16266-71). The probability of any plasma DNA ending on a specific nucleotide would vary with the distance to the TSS with a periodicity of approximately the size of nucleosomes. It was generally believed that this fragmentation pattern is a consequence of apoptotic degradation of the DNA. Therefore, the size of plasma DNA generally resembles the size of DNA associated with a histone complex.

In previous studies, it was also shown that the size of plasma DNA generally resembles the size of DNA associated with a nucleosome (Lo et al. Sci Transl Med 2010; 2(61):61ra91). It is believed that plasma DNA is generated through the apoptotic degradation of cellular DNA (nuclear DNA and mitochondrial DNA). This view is further supported by the lack of this nucleosomal pattern in circulating mitochondrial DNA as mitochondrial DNA is not associated with histones in cells. Although it was shown that the nucleotide position that a plasma DNA fragment ends is not random close to transcriptional start sites (Fan et al. PNAS 2008; 105:16266-71), the exact mechanism governing the fragmentation patterns of plasma DNA is still unclear.

Recently, it has further been shown that the size of plasma DNA would be different in regions with different sequence contexts (Chandrananda et al. BMC Med Genomics 2015; 8:29). The latter data also support the previous hypothesis that cell-free DNA fragments are more likely to start and end on nucleosome linker regions, rather than at nucleosomal cores. These findings are consistent with our finding of the nucleotide-to-nucleotide variation in intact probability as discussed in previous sections. Here, we further hypothesize that the amplitude of the variation in the intact probability would vary across different genomic regions. This region-to-region variation in the fragmentation variability has not been adequately explored or quantified in any previous studies. The following figures illustrate the concept of local and regional variation in $P_I$.

Figure 7:
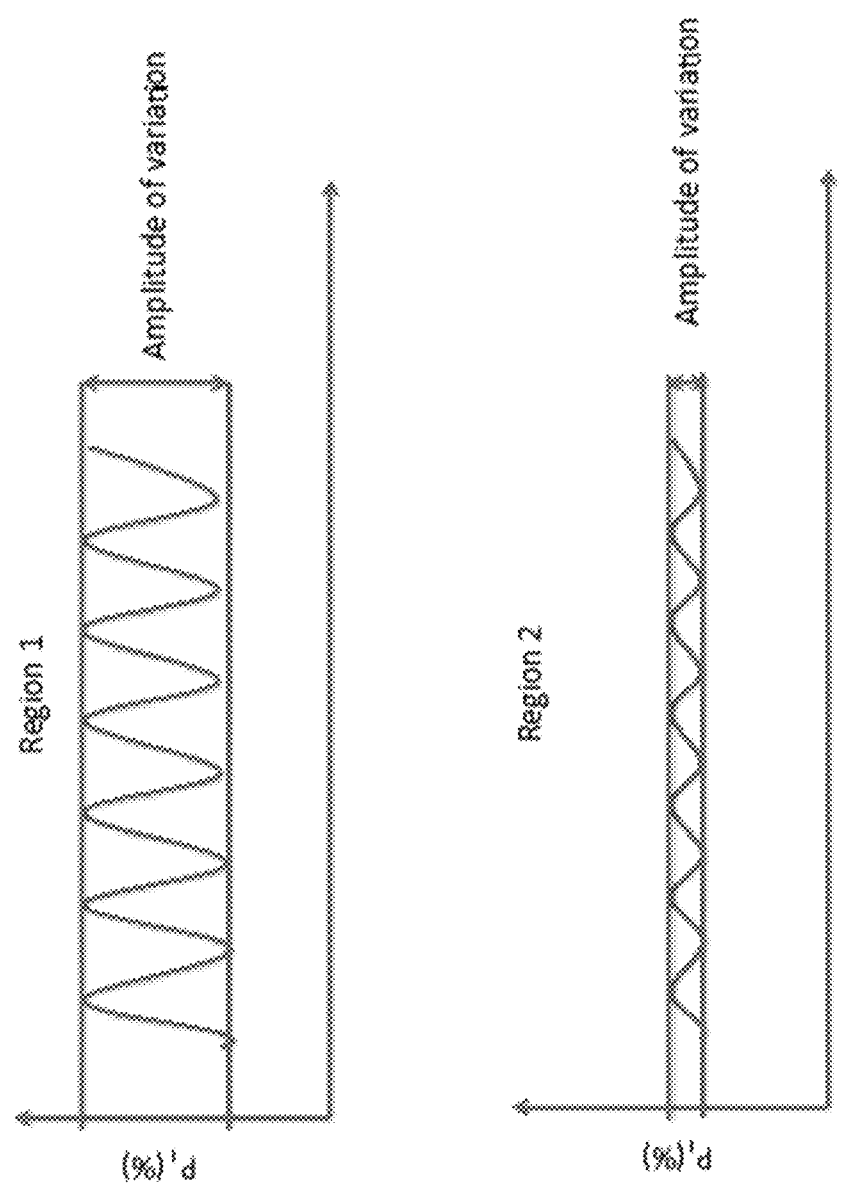
FIG. 7 shows an illustration of the amplitude of variation of $P_I$.

FIG. 7 shows an illustration of the amplitude of variation of $P_I$. In the previous sections, we have demonstrated that there is sinusoidal-like pattern of variation in $P_I$ on a short stretch of DNA. Here we further analyze the amplitude of the variation across larger genomic regions. The amplitude of variation refers to the difference in $P_I$ between the highest peak and trough variation of $P_I$ at a particular region with specified size. In one embodiment, the size of a particular region can be 1000 bp. In other embodiments, other sizes, for example but not limited to 600 bp, 800 bp, 1500 bp, 2000 bp, 3000 bp, 5000 bp and 10000 bp, can be used.

As shown in FIG. 7, the amplitude of region 1 is higher than the amplitude in region 2. This behavior is seen in the data below. If such occurrences of high amplitudes occur at different genomic regions for different tissues, then a measurement of amplitude can be used to determine a proportional contribution of a tissue type when analyzing a region where the amplitude differs between the tissue types. For example, if the amplitude is different for different tissue types, then the proportional contribution would vary proportionally with an increasing amount of DNA from a particular tissue type (e.g., fetal tissue or tumor tissue). Accordingly, a measure of the amplitude would correspond to a particular proportional contribution. Embodiments can use calibration data from samples where the proportional contribution is measured via another technique (e.g., by analysis of alleles, methylation signatures, degree of amplification/deletion) as are described in U.S. Patent Publication Nos. 2009/0087847, 2011/0276277, 2011/0105353, 2013/0237431, and 2014/0100121, which are incorporated by reference in their entirety.

In our sequencing data, we observed that the amplitude of variation in $P_I$ varied across different genomic regions. We hypothesize that the amplitude of variation of $P_I$ is related to the accessibility of the chromatin to degradation during apoptosis. Thus, we investigated the possible relationship between the amplitude of variation and DNase hypersensitivity sites in the genome. In a previous study, it was observed that the fragmentation pattern of plasma DNA is affected by its relative position to the TSS. In our analysis, we investigated the relative importance of TSS and DNase hypersensitivity sites on the effect of the fragmentation patterns of plasma DNA. Other sites where the amplitude corresponds to the tissue being tested can be used. One example of such a type of site is one that is identified using the Assay for Transposase-Accessible Chromatin with high throughput sequencing (ATAC-Seq) (Buenrostro et al. Nat Methods 2013; 10: 1213-1218). Another example of such a type of site is one that is identified using micrococcal nuclease (MNase).

We compared the amplitude of $P_I$ variation in two types of genomic regions:

ii. Regions that are TSS but not DNase hypersensitivity sites; and
iii. Regions that are DNase hypersensitivity sites but not TSS.

The coordinates of the TSS and the DNase hypersensitivity sites were retrieved from the ENCODE database (genome.ucsc.edu/ENCODE/downloads.html).

The $P_I$ patterns around TSS and DNase I sites were profiled using the following approach.
1) The upstream and downstream 2 kb regions around targeted reference sites were retrieved.
2) Then the absolute genomic coordinates were re-scaled according to the distance to a reference site. For example, if a particular window with 60 bp in size is 50 bp from a reference site in an upstream direction, it will be marked as −50. Otherwise if a particular window with 60 bp in size is 50 bp from reference site in a downstream direction, it will be marked as +50.
3) The $P_I$ value in a particular window with the same rescaled new coordinates will be recalculated using the count of intact fragments and all fragments which are overlapped with the said window.

Figure 8B:
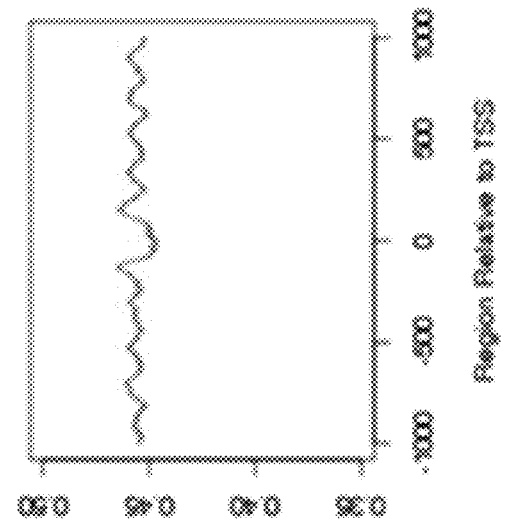
FIG. 8B shows patterns of $P_I$ variation at regions that are TSS but not DNase hypersensitivity sites.
Figure 8A:
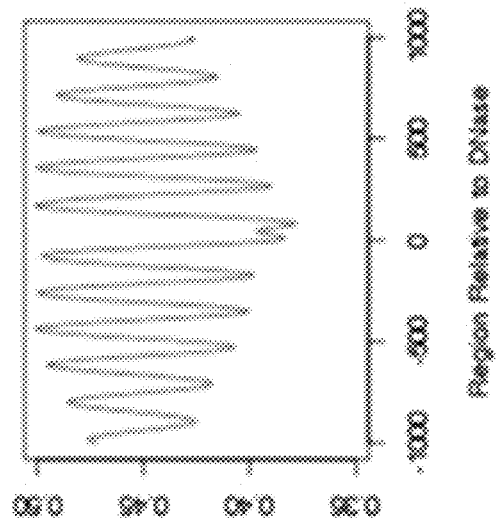
FIG. 8A shows patterns of $P_I$ variation at regions that are DNase hypersensitivity sites but not TSS.

FIG. 8A shows patterns of $P_I$ variation at regions that are DNase hypersensitivity sites but not TSS. FIG. 8B shows patterns of $P_I$ variation at regions that are TSS but not DNase hypersensitivity sites. As shown, the amplitude of variation is much higher in regions that are DNase hypersensitivity sites but not TSS, than those which are TSS but not DNase hypersensitivity sites. These observations suggest that one factor influencing the fragmentation pattern of plasma DNA is the relative position of a region subjected to fragmentation to DNase hypersensitivity sites.

III. Using Peaks and Troughs to Determine Proportion of Tissue

Figure 9:
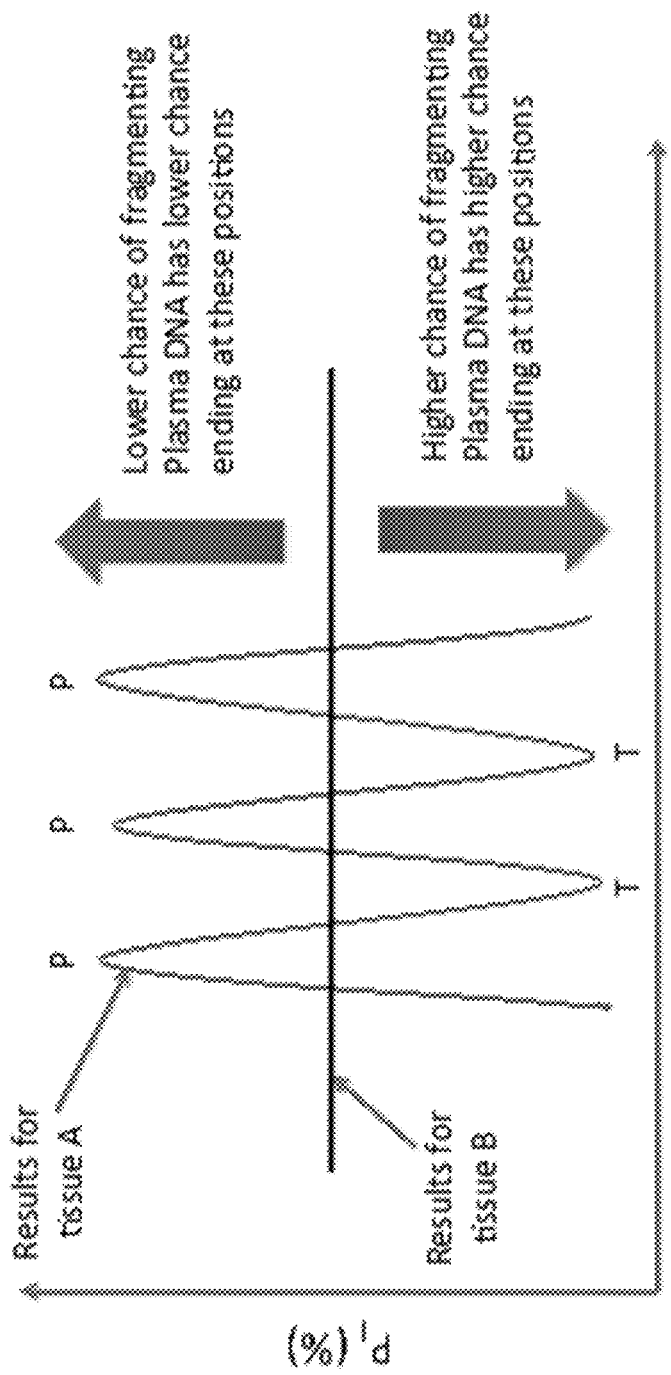
FIG. 9 shows an illustration of the principle for the measurement of the proportion of DNA released from different tissues.

Having demonstrated that the relative position to the DNase hypersensitivity sites is an important factor governing the fragmentation pattern of plasma DNA, we investigated if this observation can be translated into clinical applications. It has been observed that the profiles of DNase hypersensitivity sites are different in different types of tissues. The profiles correspond to genomic locations of the sites; locations of DNase hypersensitivity sites are different for different tissues. Thus, we reason that the plasma DNA released from different types of tissues would exhibit tissue-specific fragmentation patterns. In a similar manner, other regions where the amplitude for a region varies from tissue to tissue can be used. A. Example for DNase hypersensitivity sites FIG. 9 shows an illustration of the principle for the measurement of the proportion of DNA released from different tissues. Plasma DNA derived from tissue A has a lower probability of fragmenting at nucleotide positions with high $P_I$ (peaks, denoted by P). Therefore, the ends of plasma DNA derived from tissue A has a lower probability of being located at these nucleotide positions. In contrast, the ends of plasma DNA derived from tissue A has a higher probability of being located at nucleotide positions with low $P_I$ (troughs, denoted by T). On the other hand, as this site is not a DNase hypersensitivity site for tissue B, the amplitude of $P_I$ variation is low for plasma DNA derived from tissue B. Therefore, the probability of plasma DNA from tissue B ending on the positions P and positions T would be similar, at least relative to the amount of variation seen for tissue A.

We define the fragment end ratio at regions that are DNase hypersensitivity sites of tissue A ($FR_A$) as follows:

$$FR_A = \frac{N_T}{N_P}$$

where $N_T$ is the number of plasma DNA fragments ending on nucleotide positions of the troughs of $P_I$ and $N_P$ is the number of plasma DNA fragments ending on nucleotide positions of the peaks of $P_I$. $FR_A$ is an example of a separation value, and more specifically an example of relative abundance of DNA fragments ending on the trough relative to ending on the peak. In other embodiments, separate ratios of neighboring troughs (local minimum) and peaks (local maximum) can be determined, and an average of the separate ratios can be determined.

For tissue A, $FR_A$ would be larger than 1 because $N_T$ would be larger than $N_P$. For tissue B, $FR_A$ would be approximately 1 because $N_T$ and $N_P$ would be similar. Therefore, in a mixture containing the plasma DNA derived from both tissues A and B, the value of $FR_A$ would have a positive correlation with the proportional contribution of tissue A. In practice, $FR_A$ for tissue B does not need to be 1. As long as $FR_A$ for tissue B is different from the $FR_A$ for tissue A, the proportional contribution of the two types of tissues can be determined from $FR_A$.

In such regions, the high variation in likelihood for DNA fragments to end at the troughs will result in a higher number of DNA fragments ending at such positions than ending at the peaks (Note that for different defined relative abundance values, a higher likelihood may occur for the peaks). When more DNA fragments are from tissue type A, the larger the difference will be in the number of DNA fragments ending at the troughs and the peaks. Thus, as the proportional contribution of tissue A increases, the larger will be the separation between the number of DNA fragments ending on a trough and the number of DNA fragments ending on a peak. This separation value corresponds to the high amplitude in the likelihood function shown in FIG. 9 for tissue A.

B. Relationship Between Relative Abundance and Proportional Contribution

Figure 10:
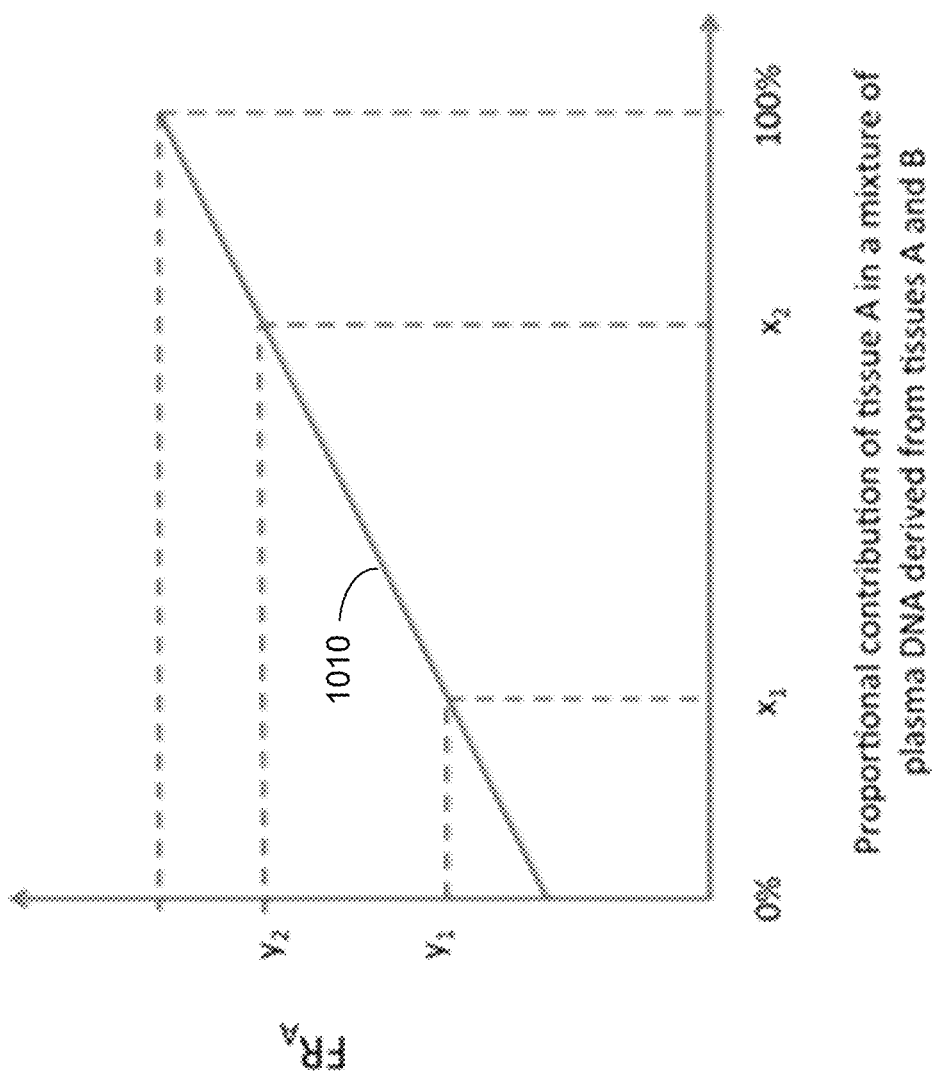
FIG. 10 shows the relationship between $FR_A$ and the proportional contribution of tissue A to DNA in a mixture determined by analysis of two or more calibration samples with known proportional concentrations of DNA from tissue A.

FIG. 10 shows the relationship between $FR_A$ and the proportional contribution of tissue A to DNA in a mixture determined by analysis of two or more calibration samples with known proportional concentrations of DNA from tissue A. In the example shown, two samples with proportional contribution of tissue A of $x_1$ and $x_2$ are analyzed. The $FR_A$ values of the two samples were determined as $y_1$ and $y_2$, respectively. The relationship between $FR_A$ and the proportional contribution of A can be determined based on the values of $x_1$, $x_2$, $y_1$ and $y_2$.

The values y1 and y2 are examples of calibration values. The data points (x1,y1) and (x2,y2) are examples of calibration data points. The calibration data points can be fit to a function to obtain a calibration curve 1010, which may be linear. When a new $FR_A$ (or other relative abundance value) is measured for a new sample, the new $FR_A$ can be compared to at least one of the calibration values to determine a classification of the proportional contribution of the new sample. The comparison to the calibration value can be made in various ways. For example, the calibration curve can be used to find the proportional contribution x corresponding to the new $FR_A$. As another example, the new $FR_A$ can be compared to calibration value y1 of a first calibration data point to determine whether the new sample as a proportional contribution greater or less than x1.

In other embodiments, a mixture containing more than two types of tissues can be analyzed similarly for the proportional contribution of tissues A as long as the $FR_A$ of other tissues is relatively constant. Such methods are practically useful for the analysis of different clinical scenarios, for example but not limited to cancer detection, transplantation monitoring, trauma monitoring, infection and prenatal diagnosis.

In one embodiment, the fractional concentration of the affected tissue in the plasma of a cancer patient can be determined. For example, in a patient with liver cancer, the fractional contribution of the liver DNA can be determined via the analysis of the liver-specific open chromatin regions, e.g., DNase hypersensitivity sites. In one embodiment, this can be done using DNase-Seq (Boyle et al. Cell 2008; 132: 311-322; Madrigal et al. Front Genet 2012; 16: 123-131). In another embodiment, this can be performed by Formaldehyde-Assisted Isolation of Regulatory Elements (FAIRE)-Seq (Giresi et al. Genome Res 2007; 17: 877-885). In yet another embodiment, this can be performed by ATAC-Seq (Buenrostro et al. Nat Methods 2013; 10: 1213-1218). The $FR_{liver}$ can be determined at these sites and compared with normal healthy subjects. At the liver-specific DNase hypersensitivity sites, the variation in $P_I$ between peak and trough regions would be mainly contributed from the liver. Through the comparison with a calibration curve similar to FIG. 10, the contribution of the liver can be determined. The value of $FR_{liver}$ of the tested case can be compared with a range of the contribution of the liver in the healthy subjects. Other regions that have a high variation in amplitude in the likelihood function of DNA fragments ending at a genomic position among various tissues of a mixture can be used. Examples of such other regions are described in more detail in later sections.

Similarly, the contribution of the transplanted organ in a patient who has received organ transplantation can be determined by this method. In previous studies, it was shown that patients with rejection would lead to an increased release of DNA from the transplanted organ resulting in an elevated concentration of the DNA from the transplanted organ in plasma. The analysis of FR of the transplanted organ would be a useful way for the detection and monitoring of organ rejection. The regions used for such analysis can vary depending on which organ is transplanted.

In another embodiment, this method can be used for the determination of fetal DNA concentration in maternal plasma. In maternal plasma, the DNA molecules carrying the fetal genotypes are actually derived from the placenta. Thus, if we focus on the DNase hypersensitivity sites that are specific for the placenta but not present in the blood cells, we would be able to determine the proportional contribution of the placenta to the plasma DNA through the analysis of the $FR_{placenta}$.

Figure 11:
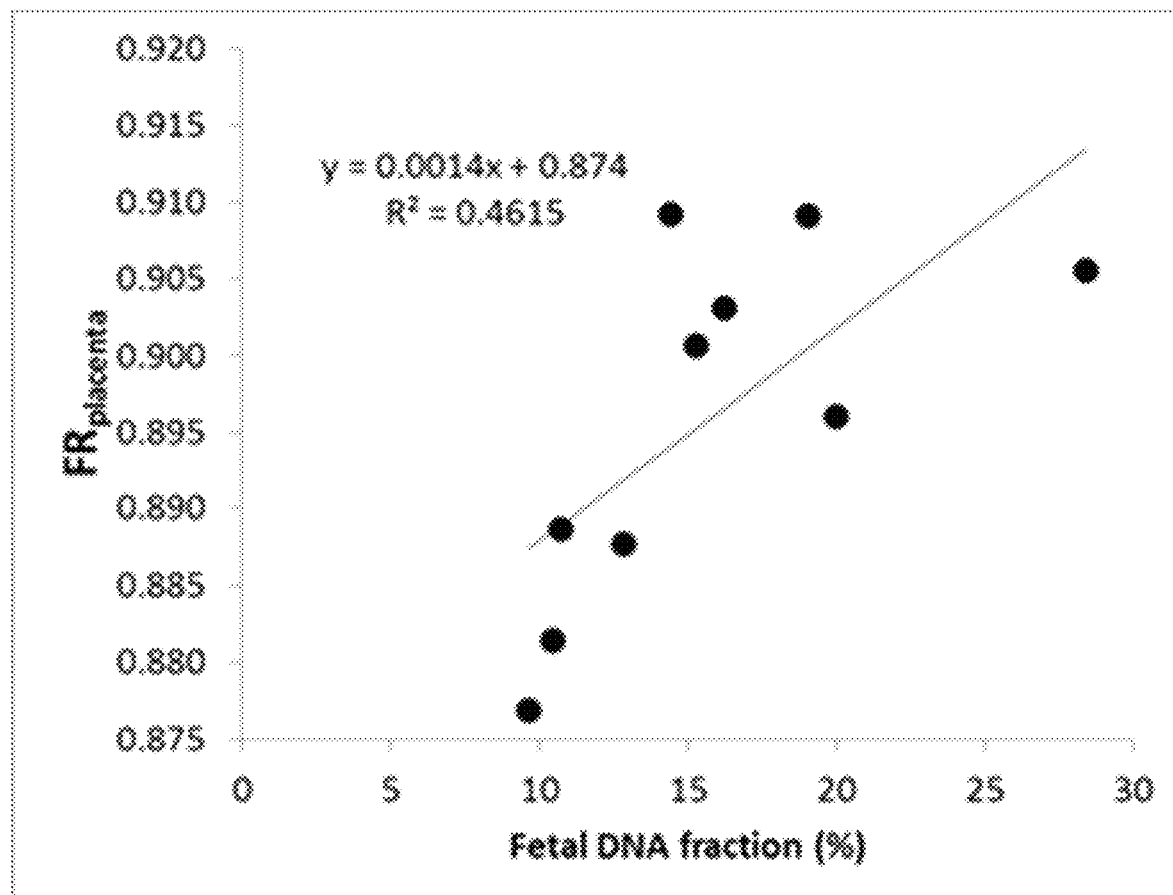
FIG. 11 shows a correlation between $FR_{placenta}$ and fetal DNA percentage in maternal plasma.

FIG. 11 shows a correlation between $FR_{placenta}$ and fetal DNA percentage in maternal plasma according to embodiments of the present invention. The vertical axis corresponds to $FR_{placenta}$ as determined using one or more local maxima and local minima that are located in one or more DNase hypersensitivity sites. The horizontal axis is fetal DNA fraction measured using a separate measurement technique. As can be seen, the value of $FR_{placenta}$ is correlated with fetal DNA fraction. In this example, the fetal DNA fraction was determined based on the proportion of fetal-specific allele at SNPs that the mother was homozygous and the fetus was heterozygous. Thus, the fetal DNA percentage can be estimated using $FR_{placenta}$ based on the sequencing results of maternal plasma DNA.

Alternatively, as the two key components in the maternal plasma are placenta-derived DNA and the DNA derived from blood cells (a different tissue type), we reasoned that $FR_{blood}$ would be negatively correlated with the fractional concentration of fetal DNA in the blood plasma. Thus, DNase hypersensitivity sites specific for blood cells were identified and $FR_{blood}$ was determined.

Figure 12:
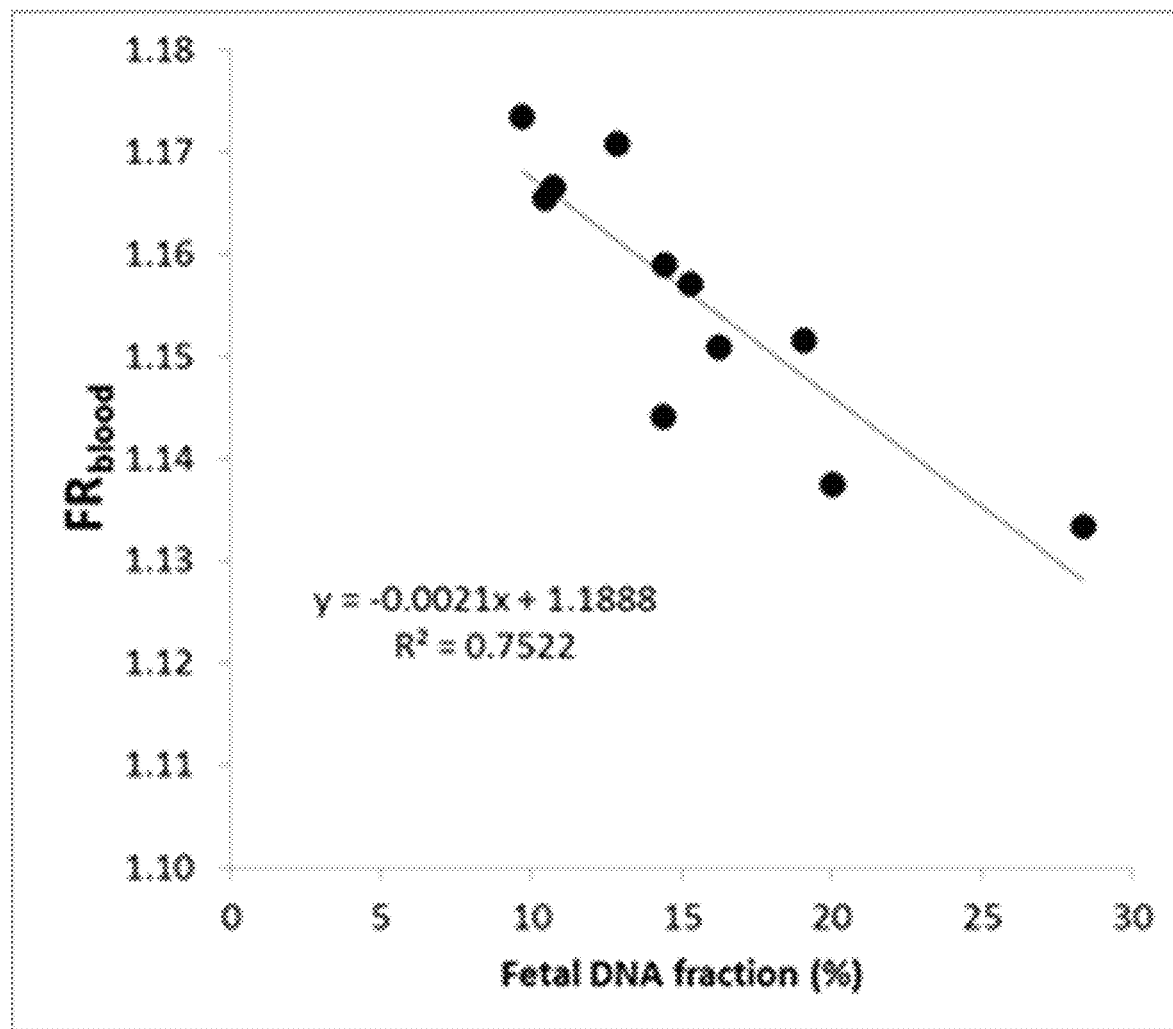
FIG. 12 shows a correlation between $FR_{blood}$ and fetal DNA concentration in maternal plasma.

FIG. 12 shows a correlation between $FR_{blood}$ and fetal DNA concentration in maternal plasma. The vertical axis corresponds to $FR_{blood}$ as determined using one or more local maxima and local minima that are located in one or more DNase hypersensitivity sites. The horizontal axis is fetal DNA fraction measured based on the proportion of fetal-specific alleles in maternal plasma. A negative correlation could be observed between $FR_{blood}$ and fetal DNA percentage. Thus, the fetal DNA percentage can be estimated using $FR_{blood}$ based on the sequencing results of maternal plasma DNA. Accordingly, a genomic region can have a fragmentation pattern specific to multiple tissue types, e.g., positive correlation(s) for some tissue(s) and negative correlation(s) for other tissue(s).

C. Method Using Maxima and Minima

Figure 13:
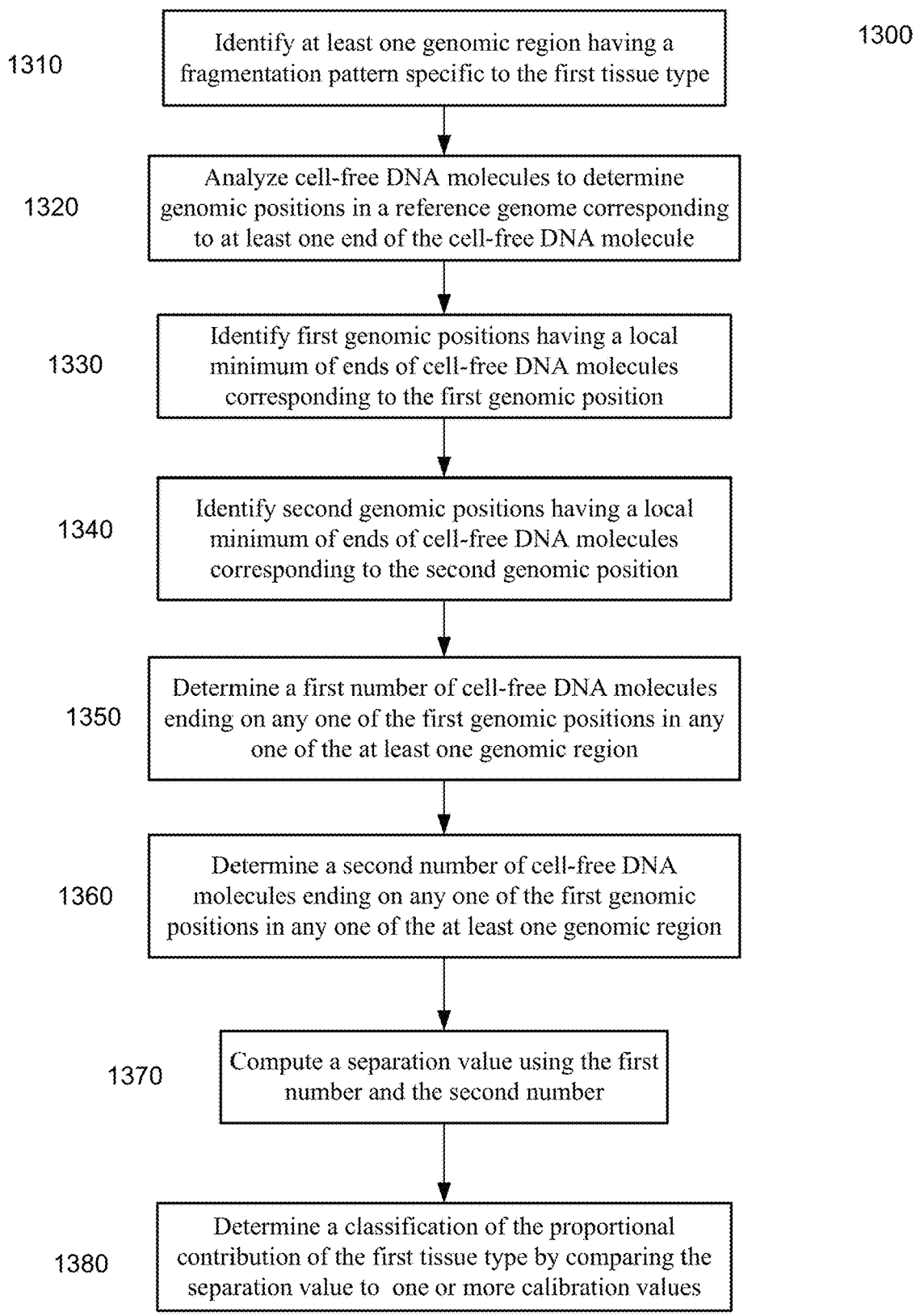
FIG. 13 is a flowchart of a method 1300 of analyzing a biological sample to determine a classification of a proportional contribution of the first tissue type according to embodiments of the present invention.

FIG. 13 is a flowchart of a method 1300 of analyzing a biological sample to determine a classification of a proportional contribution of the first tissue type according to embodiments of the present invention. The biological sample includes a mixture of cell-free DNA molecules from a plurality of tissues types that includes the first tissue type. As with other methods described herein, method 1300 can use a computer system. The first tissue type (e.g., liver tissue or fetal tissue) can be selected based on the specific subject. For example, if the subject previously had liver cancer, then screening can be performed to check whether the liver cancer has returned, which would result in an increase in the proportional contribution from liver tissue. Such a selection criteria applies to other methods described herein.

At block 1310, at least one genomic region having a fragmentation pattern specific to the first tissue type is identified. As an example, the at least one genomic region can include one or more DNase hypersensitivity sites. Each of the at least one genomic region having a fragmentation pattern specific to the first tissue type can include one or more first tissue-specific alleles in at least one additional sample, e.g., as will be described in section VI. As another example, the at least one genomic region can include one or more ATAC-seq or micrococcal nuclease sites. The first tissue type can correspond to a particular organ or even to a particular cancer of the organ.

At block 1320, a plurality of cell-free DNA molecules from the biological sample are analyzed. The analyzing of a cell-free DNA molecule includes determining a genomic position (ending position) in a reference genome corresponding to at least one end of the cell-free DNA molecule. Thus, two ending positions can be determined, or just one ending position of the cell-free DNA molecule.

The ending positions can be determined in various ways, as described herein. For example, the cell-free DNA molecules can be sequenced to obtain sequence reads, and the sequence reads can be mapped (aligned) to the reference genome. If the organism was a human, then the reference genome would be a reference human genome, potentially from a particular subpopulation. As another example, the cell-free DNA molecules can be analyzed with different probes (e.g., following PCR or other amplification), where each probe corresponds to a genomic location, which may cover the at least one genomic region.

A statistically significant number of cell-free DNA molecules can be analyzed so as to provide an accurate determination the proportional contribution from the first tissue type. In some embodiments, at least 1,000 cell-free DNA molecules are analyzed. In other embodiments, at least 10,000 or 50,000 or 100,000 or 500,000 or 1,000,000 or 5,000,000 cell-free DNA molecules, or more, can be analyzed.

At block 1330, a first set of first genomic positions is identified. Each first genomic position has a local minimum of ends of cell-free DNA molecules corresponds to the first genomic position. Multiple neighboring genomic positions can be defined as a local extremum (maximum or minimum), and thus a local maximum is not limited to just one position.

In some embodiments, a ratio can be determined for each of a plurality of genomic positions. A first amount of cell-free DNA molecules that end at the genomic position and extend at least a specified number of nucleotides to both sides of the genomic position can be determined, e.g., as described for FIG. 1. A second amount of cell-free DNA molecules that are located at the genomic position can be used with the first amount to determine the ratio. A plurality of local minima and a plurality of local maxima can be identified in the ratios, e.g., by stepping through the ratio values to identify one or more contiguous genomic positions occurring at each of the extremum (maximum or minimum).

At block 1340, a second set of second genomic positions is identified. Each second genomic position having a local maximum of ends of cell-free DNA molecules corresponds to the second genomic position. The second set can be identified in a similar manner as the first set.

At block 1350, a first number of cell-free DNA molecules ending on any one of the first genomic positions in any one of the at least one genomic region is determined. The first number can be determined in various ways, e.g., as a sum across all first genomic positions. As another example, separate amount can be determined at each genomic position. Thus, determining the first number of cell-free DNA molecules can include determining a first amount of cell-free DNA molecules ending on each first genomic position, thereby determining a plurality of first amounts.

At block 1360, a second number of cell-free DNA molecules ending on any one of the second genomic positions in any one of the at least one genomic region is determined. The second number can be determined in a similar manner as the first number. Thus, determining the second number of cell-free DNA molecules can include determining a second amount of cell-free DNA molecules ending on each second genomic position, thereby determining a plurality of second amounts.

At block 1370, a separation value using the first number and the second number is computed. The separation value can be computed in various ways, e.g., by a ratio of the first number and the second number, as described in section III.A. In another implementation using multiple maxima and minima, an amount at each such genomic position can be determined. Computing the separation value can include determining a plurality of separate ratios, each separate ratio of one of the plurality of first amounts and one of the plurality of second amounts. The separation value can be determined using the plurality of separate ratios, e.g., a mean or median of the separate ratios.

At block 1380, the classification of the proportional contribution of the first tissue type is determined by comparing the separation value to one or more calibration values determined from one or more calibration samples whose proportional contributions of the first tissue type are known.

D. Amplification-Free Analysis

The analysis of the cell-free DNA molecules in block 1310 can be amplification free. When using PCR, the sequencing depth (i.e. the number of sequence reads covering a particular nucleotide or ending on the particular nucleotide in a reference genome) does not directly reflect how many plasma DNA molecules covering that particular nucleotide are analyzed. This is because one plasma DNA molecule can generate multiple replicates during the PCR process, and multiple sequence reads can originate from a single plasma DNA molecule. This duplication problem would become more important with i) a higher number of PCR cycles for amplifying the sequencing library; ii) an increased sequencing depth, and iii) a smaller number of DNA molecules in the original plasma sample (e.g. a smaller volume of plasma).

In addition, the PCR step introduces further errors (Kinde et al. Proc Natl Acad Sci USA 2011; 108: 9530-9535) because the fidelity of a DNA polymerase is not 100%, and occasionally, an erroneous nucleotide would be incorporated into the PCR daughter strand. If this PCR error occurs during the early PCR cycles, clones of daughter molecules showing the same error would be generated. The fractional concentration of the erroneous base may reach such a high proportion among other DNA molecules from the same locus that the error would be misinterpreted, e.g., as a fetal-derived or tumor-derived mutation. Examples of PCR-free protocols include: Berry Genomics (investor.illumina.com/mobile.view?c=121127&v=203&d=1 &id=1949110); Illumina (illumina.com/products/truseq-dna-pcr-free-sample-prep-kits.html), and various single molecule sequencing techniques. Further details of an amplification-free analysis can be found in PCT Application No. PCT/CN2016/073753.

Accordingly, some embodiments can include obtaining template DNA molecules from the biological sample to be analyzed; preparing a sequencing library of analyzable DNA molecules using the template DNA molecules, the preparation of the sequencing library of analyzable DNA molecules not including a step of DNA amplification of the template DNA molecules; sequencing the sequencing library of analyzable DNA molecules to obtain a plurality of sequence reads corresponding to the first plurality of cell-free DNA molecules. Analyzing the first plurality of cell-free DNA molecules can include receiving, at the computer system, the plurality of sequence reads and aligning, by the computer system, the plurality of sequence reads to the reference genome to determine genomic positions for the plurality of sequence reads.

IV. Relative Abundance of Left and Right Nucleotides

Figure 14:
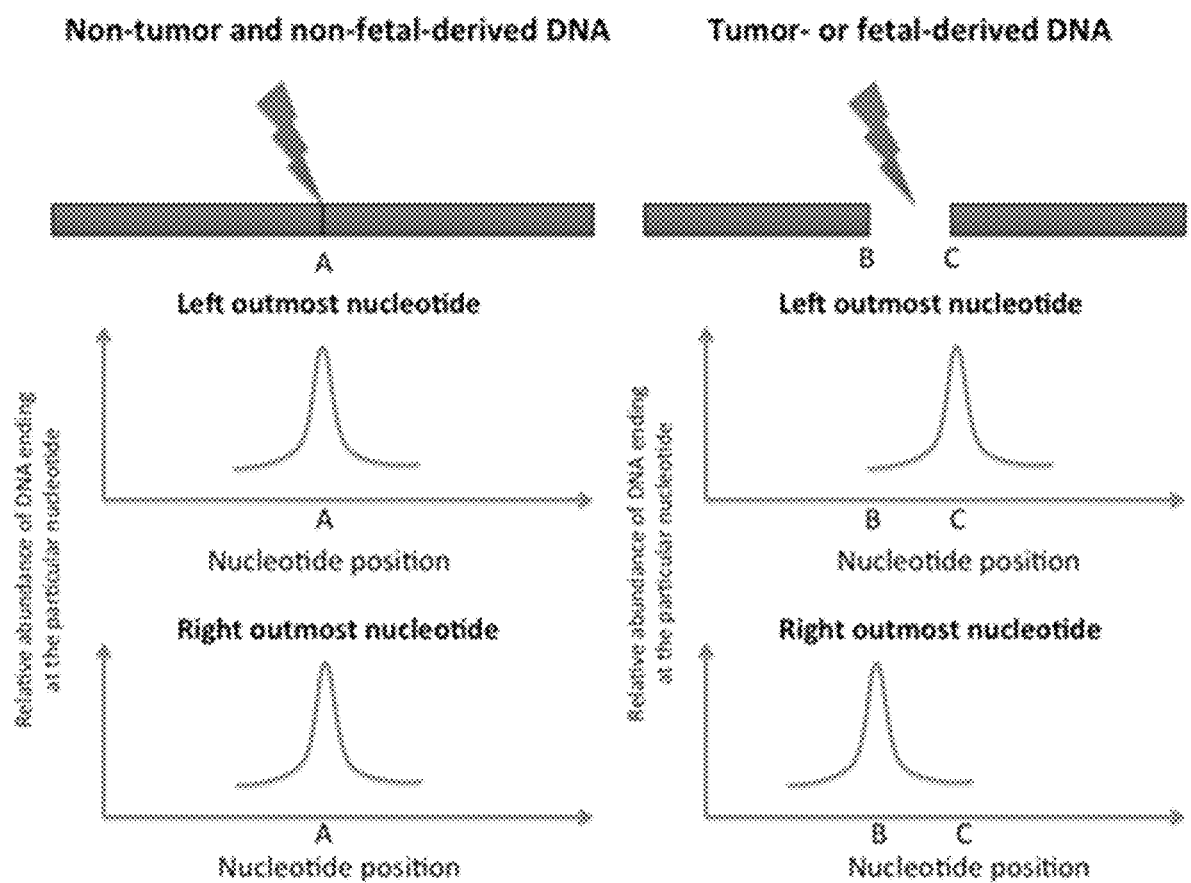
FIG. 14 shows an illustration of the principle of a difference for where circulating DNA fragments for tumor or fetal-derived DNA.

FIG. 14 shows an illustration of the principle of a difference for where circulating DNA fragments for tumor or fetal-derived DNA. In previous studies, it has been shown that the size of the circulating DNA closely resembles the size of nucleosomal DNA. The major peak of 166 bp in the size distribution of plasma DNA represents the DNA associated with the core of the histone complex together with the linker DNA connecting two successive histones complex.

It has also been observed that the size distributions of fetal- and tumor-derived DNA molecules are shorter than those for the non-tumor- and non-fetal-derived DNA in the plasma of cancer patients and pregnant women (Lo et al. Sci Transl Med 2010; 2(61):61ra91 and Jiang et al. Proc Natl Acad Sci USA 2015; 112:E1317-25.). For the size distribution of tumor- and fetal-derived DNA in plasma, the peak of 166 bp is diminished and a peak at 144 bp is more prominent. The 144 bp peak is likely to be due to the degradation of the ~20 bp linker DNA that connects two successive histones complex.

For the illustration of the principle of this method, we use the scenario of a cancer patient as an example. The same principle can then be applied for other scenarios, including the analysis of circulating fetal DNA in maternal plasma in pregnancy, and the analysis of the plasma of patients who have received transplantation. Embodiments can analyze the ends of the plasma DNA molecules, denoted as the left and right ends in the FIG. 14.

When DNA from non-malignant tissues are fragmented and released into the plasma, the connecting ends of the two molecules would both be located at nucleotide position A. In other words, for the molecule on the right side, the left outermost nucleotide is just next to the nucleotide position A. For the molecule on the left side, the right outermost nucleotide is also just next to the nucleotide position A. When the relative abundance of molecules ending at a particular nucleotide is plotted against the nucleotide coordinate, the peaks abundance of the ends would be at position A for the left and right outermost nucleotides mapping to this region. For DNA molecules derived from tumor cells, a 20 bp fragment would be removed from the molecules after the fragmentation process.

As a result, there would be a gap of 20 bp between the left side of the molecule on the right and the right side of the molecule on the left. When the relative abundance of molecules ending at a particular nucleotide is plotted against the nucleotide coordinate, the peaks for the right outermost nucleotide (located at B) and the peak for the left outermost nucleotide (located at C) would be separated by 20 bp. Therefore, the ratio between the abundance of molecules ending on nucleotide positions B and C and the abundance of molecules ending on position A would represent the fractional concentration of tumor-derived DNA in the plasma sample.

The same principle can be applied for the quantification of DNA species that have differential size distribution, for example, but not limited to, the measurement of fetal DNA in the plasma of pregnant women and the measurement of DNA from a transplanted organ.

Figure 15:
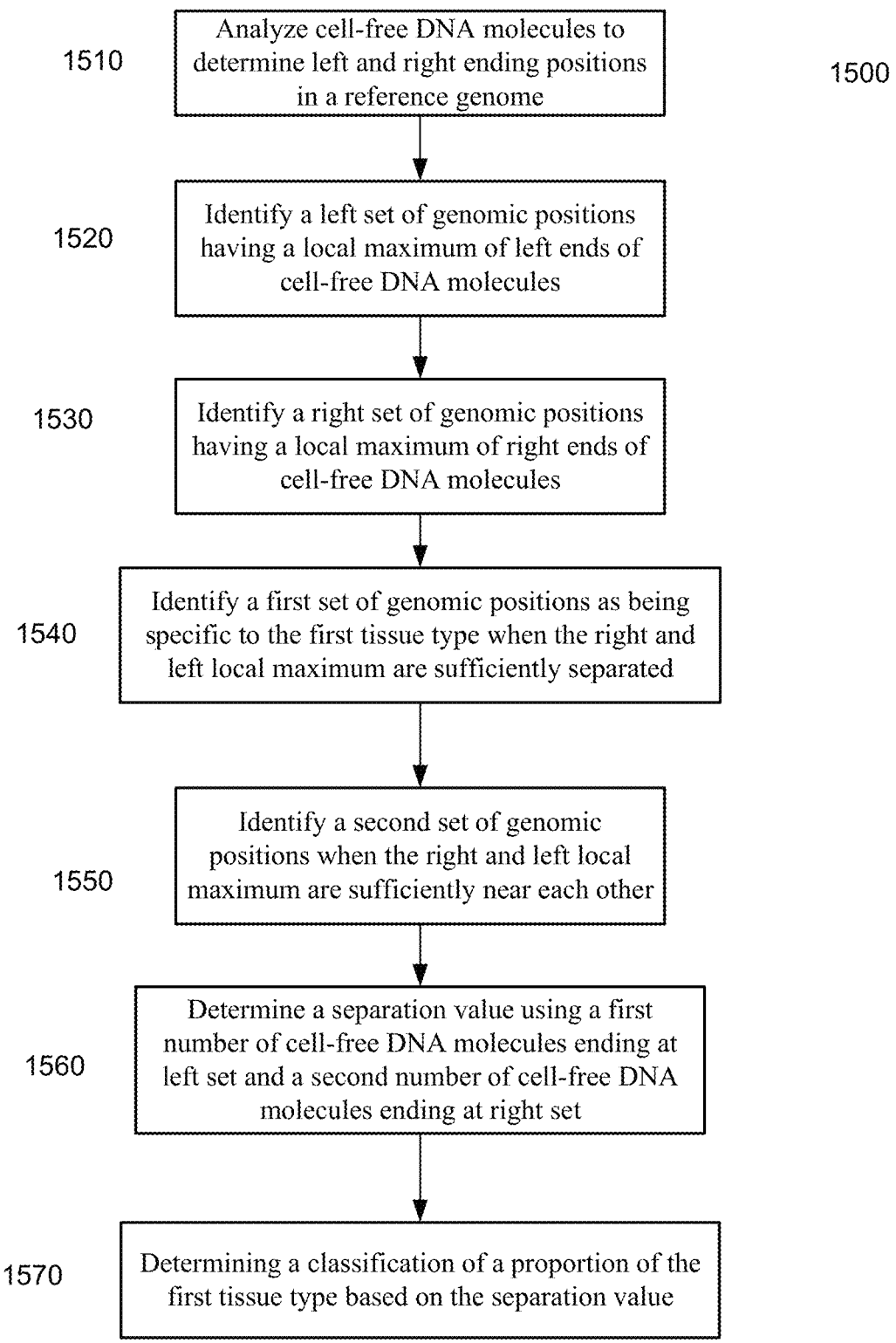
FIG. 15 is a flowchart of a method of analyzing a biological sample including a mixture of cell-free DNA molecules from a plurality of tissues types that includes a first tissue type.

FIG. 15 is a flowchart of a method 1500 of analyzing a biological sample including a mixture of cell-free DNA molecules from a plurality of tissues types that includes a first tissue type. Portions of method 1500 can be used to implement block 1310 and other blocks identifying preferred ending positions.

At block 1510, cell-free DNA molecules are analyzed to determine left and right ending positions in a reference genome. Block 1510 may be performed in a similar manner as block 1320. In block 1510, a first plurality of cell-free DNA molecules from the biological sample of a subject can be analyzed, where each of the first plurality of cell-free DNA molecules has a left end and a right end. A left ending position in the reference genome corresponding to the left end of the cell-free DNA molecule can be determined, e.g., by aligning (mapping) a sequence read of the DNA fragment to the reference genome or via a probe whose position is known in the reference genome. The left end can refer to either end, depending on the coordinate system chosen for defining the reference genome. Similarly, a right ending position in the reference genome corresponding to the right end of the cell-free DNA molecule can be determined. The two ending positions can be determined in two separate alignment steps, e.g., if the two ends have separate sequence reads.

At block 1520, a left set of left genomic positions is identified. Each genomic position of the left set has a local maximum of left ends of the first plurality of cell-free DNA molecules corresponding to one of the left set of genomic positions. The left set can be determined in a similar manner as described for maxima for method 1300.

At block 1530, a right set of right genomic positions is identified. Each genomic position of the right set has a local maximum of right ends of the first plurality of cell-free DNA molecules corresponding to one of the right set of genomic positions. The right set can be determined in a similar manner as described for maxima for method 1300.

At block 1540, a first set of genomic positions is identified as being specific to the first tissue type. All or a portion of the left genomic positions of the left set can be compared to all or a portion of the right genomic positions of the right set to identify the first set of genomic positions where a distance from a left genomic position to a nearest right genomic position is greater than a first threshold distance of genomic positions (e.g., nucleotides) in the reference genome. Examples of the first threshold distance are 5, 6, 7, 8, 9, 10, 15, and 20 nucleotides.

At block 1550, a second set of genomic positions is identified. All or a portion of the left genomic positions of the left set can be compared to all or a portion of the right genomic positions of the right set to identify the second set of genomic positions where a distance from a left genomic position to a nearest right genomic position is less than a second threshold distance of genomic position in the reference genome. Examples of the second threshold distance are 2, 3, 4, and 5 genomic positions (e.g., nucleotides).

At block 1560, a separation value is determined using a first number of the first plurality of cell-free DNA molecules ending at one of the left set of genomic positions and a second number of the first plurality of cell-free DNA molecules ending at one of the right set of genomic positions. A separation value (e.g., a relative abundance value) can be determined between the first number and the second number.

In one embodiment, pairs of the first set of genomic positions and the second set of genomic positions are identified. The pairs can be of positions that are nearest to each other. For each of one or more of the pairs, a first amount of cell-free DNA molecules ending at the first genomic position can be determined, and a second amount of cell-free DNA molecules ending at the first genomic position can be determined. The first amounts of cell-free DNA molecules correspond to the first number of the plurality of cell free DNA molecules and the second amounts of cell-free DNA molecules correspond to the second number of the plurality of cell free DNA molecules. For example, the first amounts can sum to the first number and the second amounts can sum to the second number, and the separation value can be determined directly from the first number and the second number. As another example, the separation value can be determined from a plurality of ratios, each including the first amount and the second amount for one the pairs. In various implementations, an average or median of the ratios can be used as the separation value. The respective first and second amounts of the pairs can be used in other ways to determine individual separation values used to determine the total separation value.

At block 1570, the classification of the proportional contribution of the first tissue type is determined by comparing the separation value to one or more calibration values determined from one or more calibration samples whose proportional contributions of the first tissue type are known.

Block 1570 can be performed in a similar manner as other determination of proportional contributions.

In various embodiments, both the left and right sets can be used as the first set of genomic positions; just the left set can be used; just the right set can be used; or some from the left set and some from the right set can be used. For the whole set of left positions, there is a subset of left positions that has a corresponding right set of positions separated from the subset of left positions by a threshold number of nucleotides. Therefore, it is possible to use the subset of left positions or the corresponding subset of right positions to make the calculation.

V. Use of Tissue-Specific Ending Positions

We hypothesize that the fragmentation patterns of circulating DNA derived from cancer cells, placental cells and cell types would be different. Based on this hypothesis, the coordinate of the terminal nucleotides at one or both ends of a circulating DNA fragment can be used for predicting if the DNA fragment carrying a putative mutation is actually derived from a tumor. Cancer-specific and pregnancy-specific ending positions can be identified in plasma DNA fragments.

A. Cancer Example Using Hepatocellular Carcinoma (HCC)

To illustrate the feasibility of this approach, the sequencing data of the plasma DNA for a patient with hepatocellular carcinoma (HCC) and a pregnant woman were analyzed. For illustration purposes, the analysis was focused on chromosome 8. The same approach can be applied to the whole genome or any other chromosomes.

The coordinates of the terminal nucleotides at both ends of each sequenced plasma DNA fragment was determined. Then, the number of fragments ending on each nucleotide on chromosome 8 was counted. The top 1 million nucleotides that had the highest number of DNA fragments ending on them were determined for the HCC case and the pregnant woman. The top one million can be viewed as being above a threshold.

Figure 16:
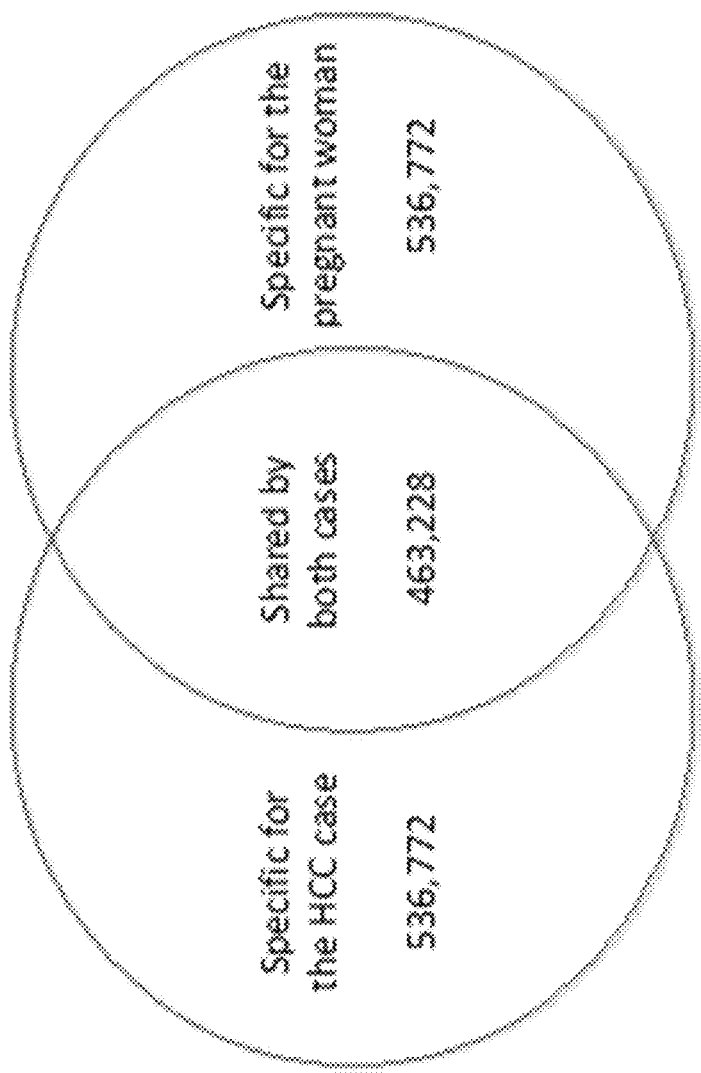
FIG. 16 is a Venn diagram showing the number of frequent endings sites that are specific for the HCC case, specific for the pregnant woman and shared by both cases.

FIG. 16 is a Venn diagram showing the number of frequent endings sites that are specific for the HCC case, specific for the pregnant woman and shared by both cases. The coordinates of the 536,772 nucleotides that were the most frequent ending positions specific for the HCC case is shown in Appendix A of U.S. patent application Ser. No. 15/218,497. The coordinates of the 536,772 nucleotides that were the most frequent ending positions specific for the pregnant woman are listed in Appendix B of U.S. patent application Ser. No. 15/218,497. The coordinates of the 463,228 nucleotides that were the most frequent ending positions shared by the two cases are omitted.

We reason that plasma DNA fragments with terminal nucleotide ending exactly at the 536,772 HCC-specific ending positions would be more likely to be derived from the tumor. Based on this assumption, the number of sequenced plasma DNA fragments that ended on the HCC-specific ending positions can be used to indicate the presence or absence of HCC or other cancers having the same plasma DNA fragmentation pattern. In another embodiment, this parameter can also be used for reflecting the level of cancer, for example but not limited to the size of the tumor, the stage of the cancer, tumor load and the presence of metastasis.

In yet another embodiment, the number of fragments ending on the HCC-specific ending positions can be correlated with the fractional concentration of cancer-derived DNA in the plasma for samples with known tumor DNA fraction in plasma. The tumor DNA fraction in plasma can be determined by, for example but not limited to, quantifying the cancer mutations in plasma or magnitude of the copy number aberrations in plasma DNA (Chan et al. Clin Chem 2013; 59:211-24). This correlation can be used as a calibration curve (FIG. 1). For patients with unknown tumor DNA fraction in plasma, the amount of DNA fragments ending on the HCC-specific ending positions can be determined. Then, the tumor DNA fraction in plasma can be determined based on the calibration curve and the amount of DNA fragments ending on the HCC-specific ending positions. In one implementation, the amount of DNA fragments ending on the HCC specific ending positions can be normalized to the total number of DNA fragments sequenced, the total number of alignable reads or the number of DNA fragments aligned to certain chromosomal regions. Thus, the proportion of sequenced DNA fragments ending on cancer-specific positions can be used as a parameter.

Figure 17:
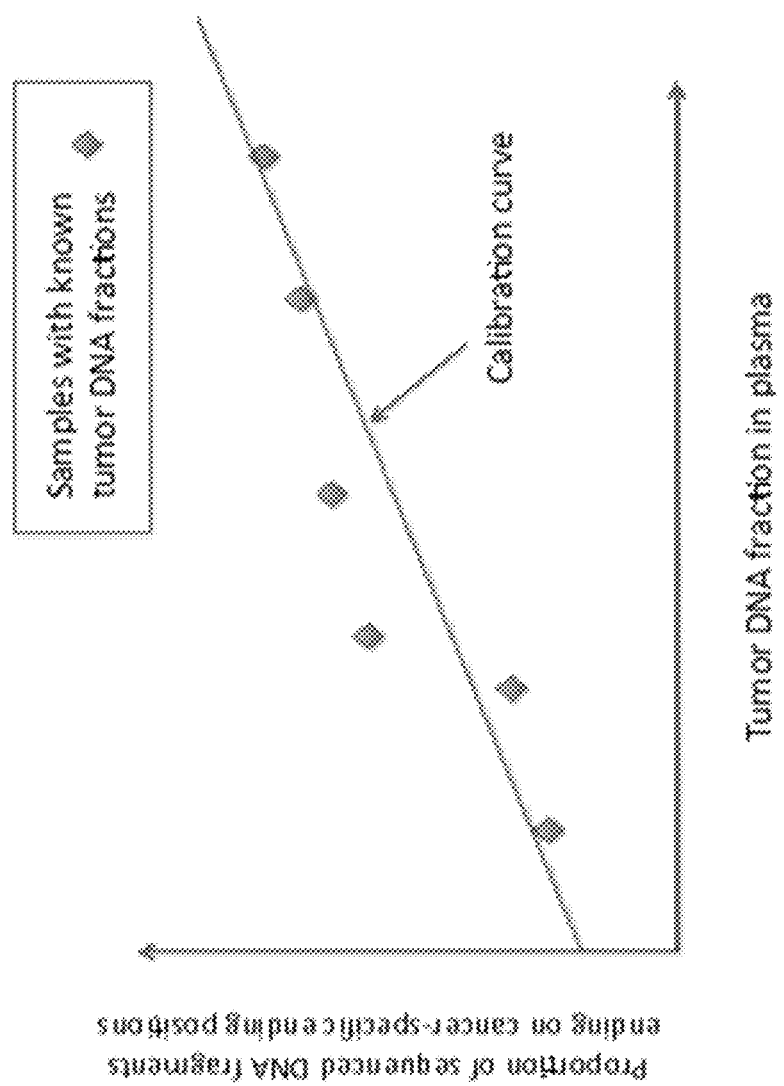
FIG. 17 shows a calibration curve showing the relationship between the proportion of sequenced DNA fragments ending on cancer-specific ending positions and tumor DNA fraction in plasma for cancer patients with known tumor DNA fractions in plasma.

FIG. 17 shows a calibration curve showing the relationship between the proportion of sequenced DNA fragments ending on cancer-specific ending positions and tumor DNA fraction in plasma for cancer patients with known tumor DNA fractions in plasma. This conceptual diagram shows a correlation of the calibration curve between tumor DNA fraction and the proportion of sequence DNA fragments ending on the cancer-specific ending positions. A calibration curve can be determined by fitting the data points determined from calibration samples, whose tumor DNA fraction was determined via other techniques.

In another embodiment of this invention, the plasma DNA fragmentation patterns for patients suffering from different types of cancers can be determined. The overlapping ends of these cancer patients can be considered as cancer-specific ends whereas the ending positions for individual cancer types can be considered as specific for a particular cancer type. For any individual suspected of having a cancer, the sequenced plasma DNA fragments can first be compared with the cancer-specific ending positions to determine the likelihood of the individual having a cancer. If the individual is likely to have a cancer, the sequenced fragments can be analyzed for the cancer type-specific ending positions to determine the most likely cancer an individual is suffering from.

In another embodiment of this invention, the ending positions of DNA derived from different organs can be determined and can be used to determine the relative contributions of DNA from different organs into plasma.

B. Fetal Example

In another embodiment, this approach can be used for determining the fetal DNA fraction in a maternal plasma sample. A calibration curve can be established by correlation the proportion of sequenced plasma DNA fragments ending on the pregnancy-specific ending positions is first determined and the fetal DNA fractions for a number of maternal plasma samples with known fetal DNA fraction. The fetal DNA fractions can be determined by a number of methods, for example but not limited to determining of the fetal specific alleles in the sample, the quantification of targets on chromosome Y for male pregnancies and the analysis of fetal-specific methylation markers. For a pregnant plasma sample with unknown fetal DNA fraction, the proportion of sequenced plasma DNA fragments ending on the pregnancy-specific ending positions can be determined. Using on this information, the fetal DNA fraction in the tested plasma DNA sample can be determined based on the calibration curve.

C. Kit for Use of Preferred Ending Positions

In some embodiments, a kit is provided for analyzing DNA in a biological sample containing a mixture of cell-free DNA molecules of a plurality of tissue types. The kit can comprising one or more oligonucleotides for specifically hybridizing to at least a section of a genomic region listed in Appendices A and B. In one embodiment, the kit includes one or more oligonucleotides for specifically hybridizing to at least a section of a genomic region listed in Appendix A for use in testing a subject for HCC. In another embodiment, the kit includes one or more oligonucleotides for specifically hybridizing to at least a section of a genomic region listed in Appendix B for use in testing a pregnant female, e.g., to determine a fetal DNA fraction in a maternal biological sample from the pregnant female.

VI. Ending Position Analysis Using Polymorphisms

In some embodiments, the regions having a tissue-specific fragmentation pattern can be identified using tissue-specific alleles. For example, a fetal-specific allele can be identified by analyzing a maternal plasma sample and comparing detected alleles to alleles detected in a maternal-only sample, as is described herein. Genomic positions that have a high rate of fetal DNA molecules ending on them relative to the rate for tissue exhibiting a shared allele (i.e., shared with the fetus and the mother) can be identified as having a fetal tissue-specific fragmentation pattern. These fetal preferred ending positions may or may not be DNase hypersensitivity sites, thereby showing that various genomic regions may have tissue-specific amplitudes for the fragmentation patterns, and embodiments are not limited to DNase hypersensitivity sites. A similar analysis can be made for a sample from a subject being screened for a tumor.

A. Fetal Example

Preferred ending positions can be obtained by analyzing a plasma DNA from a pregnant woman. The fetal- and maternal-derived plasma DNA fragments can be differentiated through polymorphism-based methods. Fragments carrying fetal- and maternal-specific alleles can be used for determining the preferred ending positions of the fetal-derived and maternal-derived DNA.

A pregnant woman with a male singleton pregnancy was recruited for this study at 38 weeks of gestation from the Department of Obstetrics and Gynaecology, Prince of Wales Hospital, Hong Kong, with informed consent. Blood samples were centrifuged at 1,600 g for 10 min at 4° C. The plasma portion was harvested and recentrifuged at 16,000 g for 10 min at 4° C. to remove the blood cells. The blood cell portion was recentrifuged at 2,500 g, and any residual plasma was removed. DNA from the blood cells and that from maternal plasma was extracted with the blood and body fluid protocol of the QIAamp DNA Blood Mini Kit and the QIAamp DSP DNA Blood Mini Kit (Qiagen), respectively. DNA from the placenta was extracted with the QIAamp DNA Mini Kit (Qiagen) according to the manufacturer's tissue protocol. The sequencing libraries were sequenced using the Illumina TruSeq PCR-free library preparation protocol. The paired-end sequencing data were analyzed using the Short Oligonucleotide Alignment Program 2 (SOAP2) in the paired-end mode (Li et al. Bioinformatics 2009; 25:1966-1967). The paired-end reads were aligned to the non-repeat-masked reference human genome (Hg19). Up to 2 nucleotide mismatches were allowed for the alignment of each end. The genomic coordinates of these potential alignments for the 2 ends were then analyzed to determine whether any combination would allow the 2 ends to be aligned to the same chromosome with the correct orientation, spanning an insert size ≤600 bp, and mapping to a single location in the reference human genome. The maternal plasma sample was sequenced to a depth of 270× coverage of a haploid human genome. The maternal blood cells, paternal blood cells and umbilical cord blood cells were sequenced to 40×, 45× and 50× haploid human genome coverage, respectively, using the same sequencing protocol.

To this end, recurrent end sequences in maternal plasma DNA were analyzed.

1. Identification of Fetal-Specific Ending Positions

Figure 18:
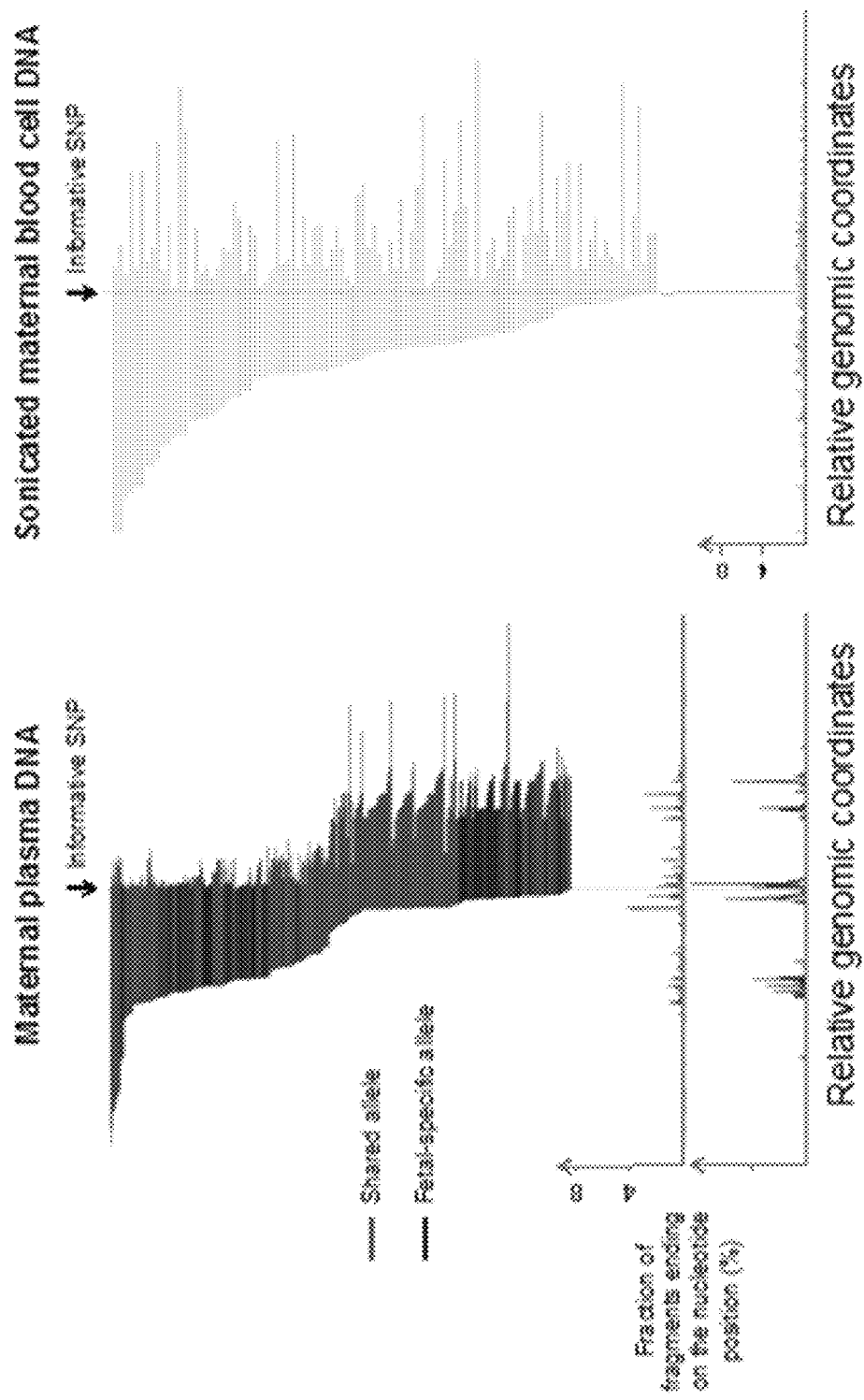
FIG. 18 shows an illustrative example of the non-random fragmentation patterns of plasma DNA carrying a fetal-specific allele and an allele shared by the mother and the fetus.

With the performance of very high sequencing depth of the maternal plasma DNA sample using a non-PCR-amplified library, we investigated if there might be sites in the maternal and fetal genomes that would be preferentially cleaved in the generation of plasma DNA. To demonstrate this effect, informative SNP loci that the mother was homozygous (genotype denoted as AA) and the fetus was heterozygous (genotype denoted as AB) were identified. In this illustrative example, the B allele would be fetal-specific and the A allele would be shared by the mother and the fetus. A representative example is shown in FIG. 18. As a control, the sequencing results of a DNA sample obtained from blood cells and artificially fragmented using sonication are shown.

A non-random fragmentation pattern was observed in the plasma DNA. For the plot of the probability of being an end of DNA fragments, three peaks were observed for each of the two groups of fragments carrying the fetal-specific and the allele shared by the mother. These peaks represent the hotspots for the end positions of fetal- and maternal-derived DNA in maternal plasma, respectively. The positions of the peaks largely overlapped between these two groups. In contrast, the fragmentation pattern for the sonicated DNA appears to be random and the fragment-end probability is similar across the region.

FIG. 18 shows an illustrative example of the non-random fragmentation patterns of plasma DNA carrying a fetal-specific allele and an allele shared by the mother and the fetus. On the upper part of the figure, each horizontal line represents one sequenced DNA fragment. The ends of the DNA fragments represent the ending position of the sequenced read. The fragments are sorted according to the coordinate of the left outermost nucleotide (smallest genomic coordinate). On the lower part of figure, the percentage of fragments ending on a particular position is shown. The X-axis represents the genomic coordinates and the SNP is located at the center indicated by the dotted line.

We further searched for coordinates that had an increased probability of being an ending position for plasma DNA fragments. We focused our search based on fragments covering the informative SNPs so that the fragments carrying fetal-specific alleles and alleles shared by the mother and the fetus could be evaluated separately. We determined if certain locations within the human genome had a significantly increased probability of being an ending position of plasma DNA fragments using a Poisson probability function. For the analysis of SNPs that the mother was homozygous (genotype AA) and the fetus was heterozygous (genotype AB), the A allele would be the "shared allele" and the B allele would be the fetal-specific allele. The number of sequenced reads carrying the shared allele and the fetal-specific allele would be counted. In the size distribution of plasma DNA, a peak would be observed at 166 bp for both the fetal-derived and maternally-derived DNA. If the fragmentation of the plasma DNA is random, the two ends would be evenly distributed across a region 166 bp upstream and 166 downstream of the informative SNP.

Figure 19:
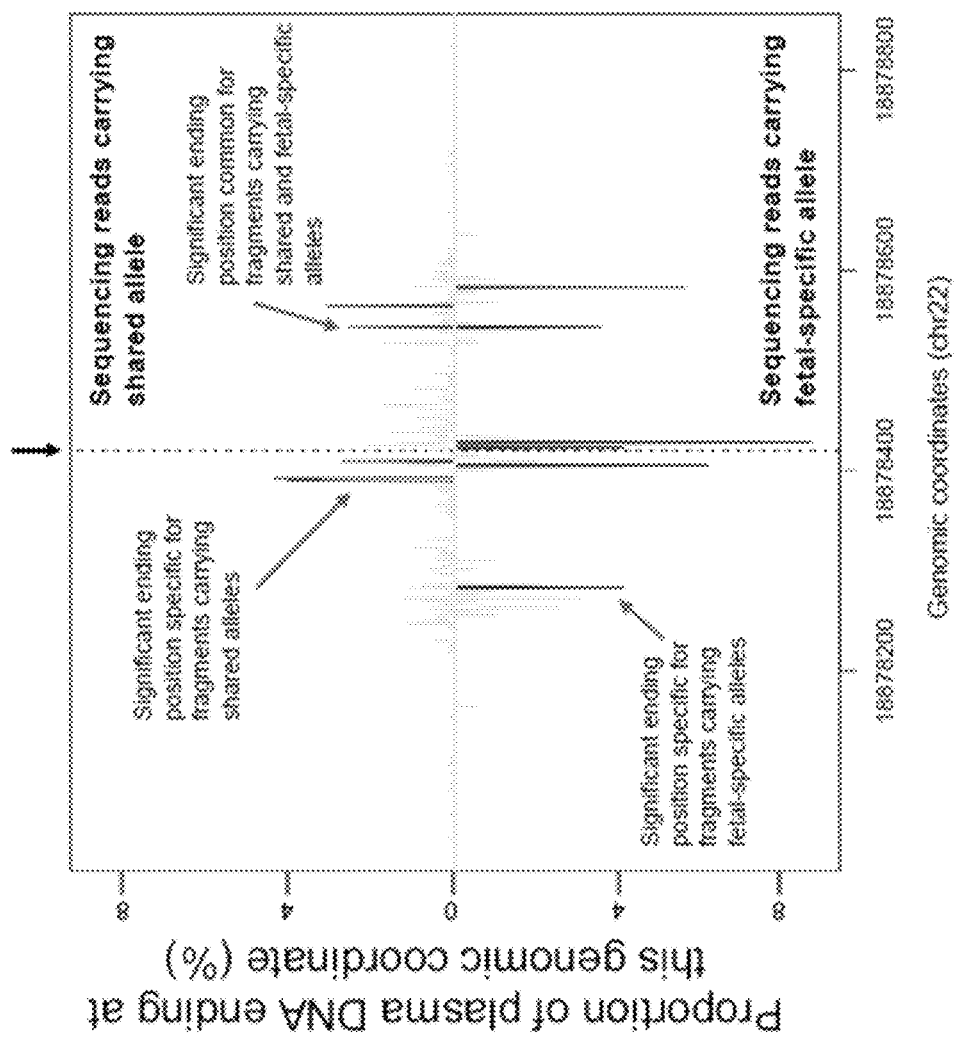
FIG. 19 shows a plot of probability a genomic coordinate being an ending position of maternal plasma DNA fragments across a region with an informative single nucleotide polymorphism (SNP).

A p-value can be calculated to determine if a particular position has significantly increased probability for being an end for the reads carrying the shared allele or the fetal-specific allele based on Poisson probability function.

$$p\text{-value}=\text{Poisson}(N_{actual}, N_{predict})$$

where Poisson( ) is the Poisson probability function; $N_{actual}$ is the actual number of reads ending at the particular nucleotide; and $N_{predict}$ is the total number of reads divided by 166. A p-value of <0.01 was used as a cutoff to define preferred ending positions for the reads carrying the fetal-specific allele or the shared allele. Statistically significant ending positions were determined for DNA fragments carrying the shared allele and the fetal-specific allele independently (FIG. 19). Other probability distributions can be used, e.g., binomial distribution, negative binomial distribution, and normal distribution.

FIG. 19 shows a plot of probability a genomic coordinate being an ending position of maternal plasma DNA fragments across a region with an informative SNP. Results for nucleotide positions with a significantly increased probability of being an end of plasma DNA fragments carrying a shared allele and a fetal-specific allele are shown in red and blue, respectively. The X-axis represents the genomic coordinates and the mutation is located at the center indicated by the dotted line. As shown, there are coordinates that have a high rate of occurrence of ending positions for just the fetal-specific allele, for just the shared allele, and some are common to both.

We identified a total of 4,131 (Set A) and 10,021 (Set B) nucleotide positions with a significantly increased chance of being an end of plasma DNA fragments carrying fetal-specific alleles and shared alleles, respectively. Set C was the overlapping set and contained 4,258 nucleotide positions (FIG. 3). These ending positions were obtained from regions spanning totally 1.42 Mb and covering 4,303 SNPs. Thus, the preferred ending positions for fetal-specific fragments accounted for 0.29% of the analyzed regions. There were 24,500, 22,942 and 31,925 plasma DNA fragments carrying fetal-specific alleles ending on Set A, Set B and Set C positions, respectively. There were 27,295, 158,632 and 87,804 plasma DNA fragments carrying shared alleles ending on Set A, Set B and Set C positions, respectively. The number or prevalence of preferred ending positions are expected to be much higher and occur at other genomic coordinates.

The polymorphism-based approach as described here only identifies preferred ending positions that are associated with an informative SNP for this fetal-maternal pair. Thus, the identified preferred ends would represent a subset of such ends in the genome. We have developed approaches that are not polymorphism-based to identify the preferred ends. Indeed, many more preferred ending approaches were identified using the non-polymorphism based approaches. Please refer to other experiments described below.

Figure 20:
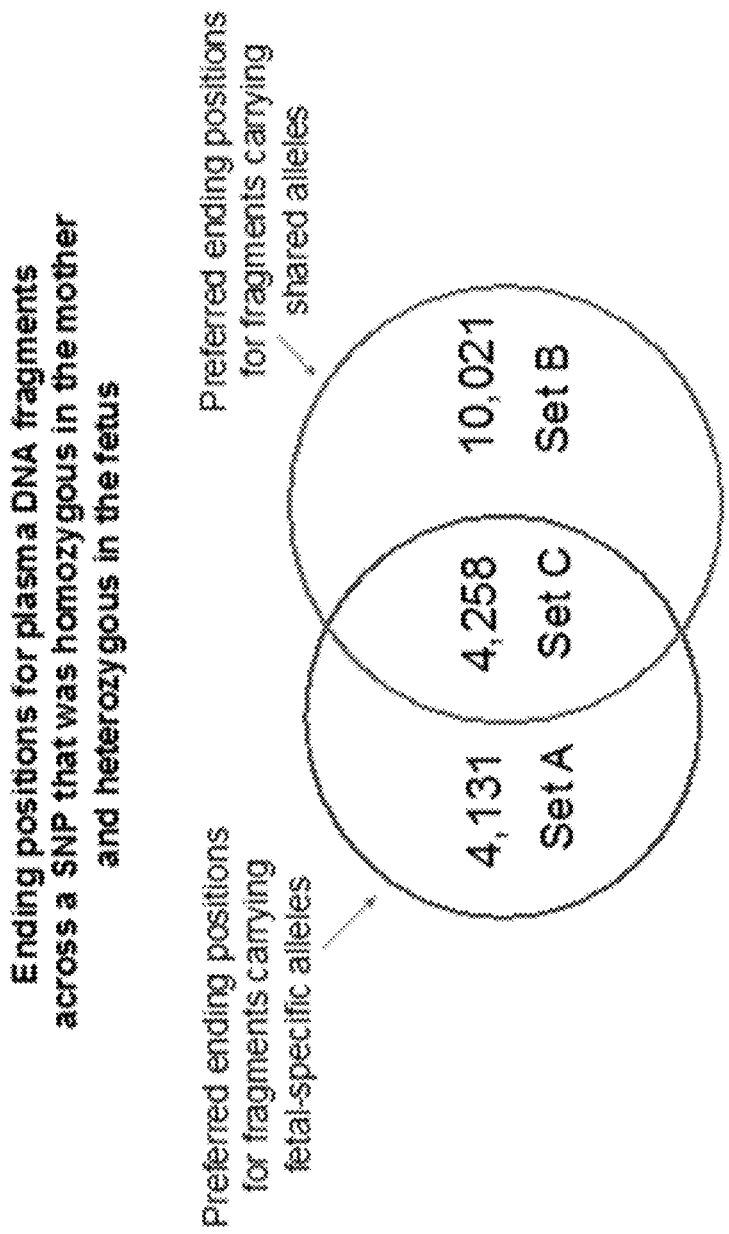
FIG. 20 shows an analysis of ending positions for plasma DNA fragments across SNPs that were homozygous in the mother and heterozygous in the fetus.

FIG. 20 shows an analysis of ending positions for plasma DNA fragments across SNPs that were homozygous in the mother and heterozygous in the fetus. Set A included preferred ending positions for fragments carrying fetal-specific alleles. Set B included preferred ending positions for fragments carrying shared alleles. Set C included preferred ending positions for both types of plasma DNA fragments.

Using the same principle, we further analyzed the ending positions for maternally derived DNA fragments across SNPs that were heterozygous in the mother (genotype AB) and homozygous in the fetus (genotype AA). We identified a total of 7,527 (Set X) and 18,829 (Set Y) nucleotide positions with significantly increased chance of being an ending position for plasma DNA fragments carrying fetal-specific alleles and shared alleles, respectively. Set Z is the overlapping set and contained 10,534 positions (FIG. 4).

These ending positions were obtained from regions spanning totally 3.1 Mb and covering 9,489 SNPs. Thus, the preferred ending positions for maternal-specific fragments accounted for 0.24% of the analyzed regions for this pair of mother and fetus. There were 69,136, 82,413 and 121,607 plasma DNA fragments carrying maternal-specific alleles ending on Set X, Set Y and Set Z positions, respectively. There were 46,554, 245,037 and 181,709 plasma DNA fragments carrying shared alleles ending on Set X, Set Y and Set Z positions, respectively. Again, this analysis focuses on plasma DNA molecules that cover at least on informative SNP, the identified preferred ends only represent a subset of such non-random ends throughout the genome.

Figure 21:
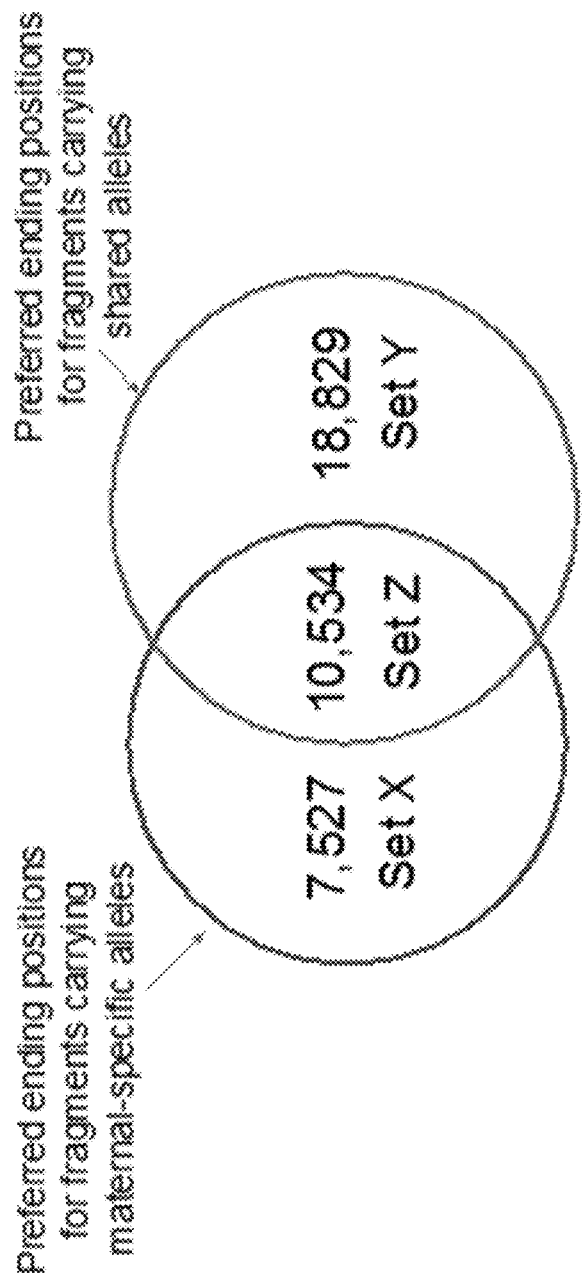
FIG. 21 shows an analysis of ending positions for plasma DNA fragments across SNPs that were homozygous in the fetus and heterozygous in the mother.

FIG. 21 shows an analysis of ending positions for plasma DNA fragments across SNPs that were homozygous in the fetus and heterozygous in the mother. Set X included preferred ending positions for fragments carrying maternal-specific alleles. Set Y included preferred ending positions for fragments carrying shared alleles. Set Z included preferred ending positions for both types of plasma DNA fragments.

2. Using Recurrent Ending Positions to Deduce Fetal DNA Fraction

After the identification of recurrent ending positions for plasma DNA fragments derived from the mother and the fetus, we reasoned that the relative abundance of plasma DNA ending on these sets of nucleotide positions would reflect the fetal DNA fraction. To confirm this, we sequenced the plasma DNA of 26 first trimester pregnant (10-13 weeks) women each carrying a male fetus. The median mapped read count was 16 million (range: 12-22 million). The proportion of sequenced reads aligning to chromosome Y was used for calculating the actual fetal DNA fraction in each plasma sample. A positive correlation could be observed between the relative abundance (denoted as F/M ratio) of plasma DNA with recurrent fetal (Set A) and maternal (Set X) ends and the fetal DNA fraction (R=0.63, P=0.0004, Pearson correlation, FIG. 22). It is interesting that while the preferred ending positions were identified based on informative SNPs for one pair of fetus and mother and only represented a subset of such ends in the genome, the identified ends were also relevant for other pregnancies and the correlation with fetal fraction was achieved even with just this subset of preferred ends.

Figure 22:
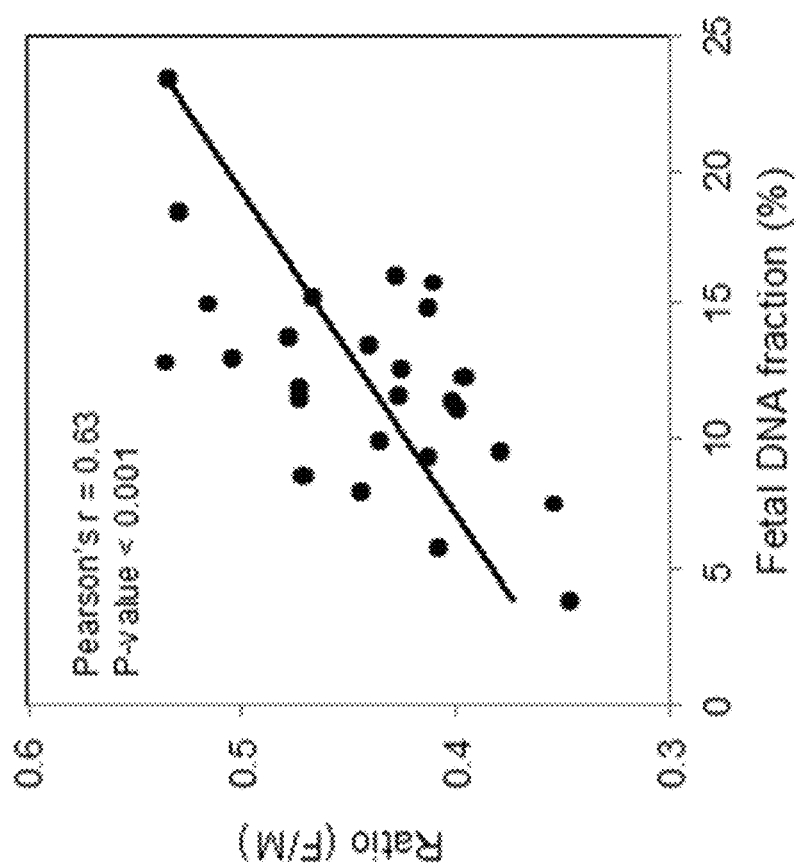
FIG. 22 shows a correlation between the relative abundance (Ratio (F/M)) of plasma DNA molecules with recurrent fetal (Set A) and maternal (Set X) ends and fetal DNA fraction.

FIG. 22 shows a correlation between the relative abundance (Ratio (F/M)) of plasma DNA molecules with recurrent fetal (Set A) and maternal (Set X) ends and fetal DNA fraction. Each of the data points can correspond to a respective calibration sample, and thus be considered calibration data points. The line fitting the calibration data points is an example of a calibration function.

Other sets can be used besides Set A and Set X. For example, a ratio (or other relative abundance or a function of a ratio) can be taken of Set A relative to Set C and Set A relative to Set B. As another example, a ratio can be taken of Set X and Set Z or a ratio between Set X and Set Y, which would provide a maternal DNA fraction, which can be assumed to be an inverse of the fetal DNA fraction. In such an example, the maternal tissue can be a first tissue type whose proportional contribution is determined, even if implicitly.

3. Use of Size

Size distribution of plasma DNA fragments ending on the fetal-specific ending positions provides further evidence that the positions are fetal-specific. To further support Set A and Set X positions were preferred ending sites for fetal-derived and maternal-derived DNA fragments, respectively, we compared the size distributions of plasma DNA ending on these two sets of positions. For the sample that these positions were derived from, the size distribution was shorter for fragments ending on Set A positions was shorter than those ending on Set X positions (FIG. 23A).

Figures 23A, 23B, 23C, 23D, 23E:
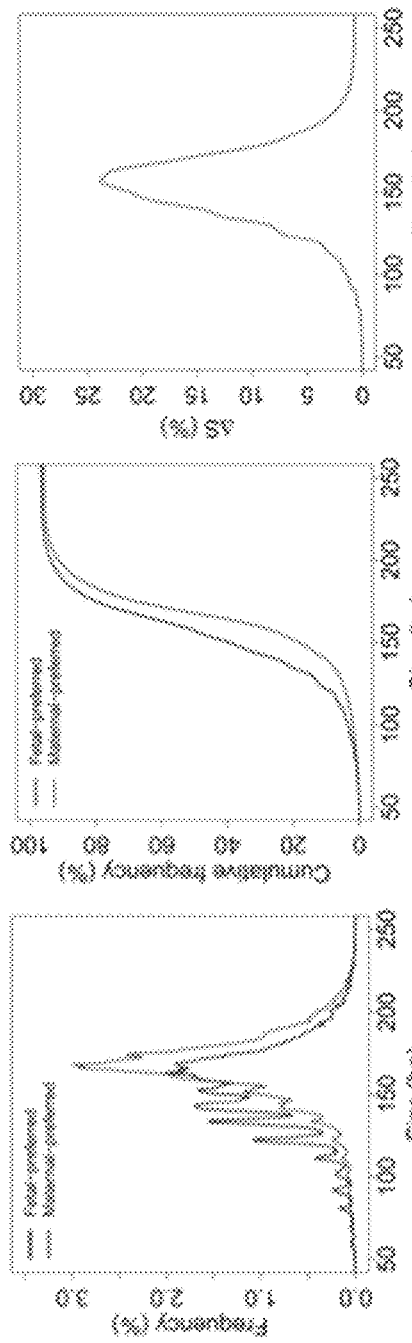
FIGS. 23A-23E show data regarding plasma DNA size distributions for fragments ending on the fetal-preferred ending positions and fragments ending on the maternal-preferred ending positions.

FIG. 23A shows plasma DNA size distributions for fragments ending on the fetal-preferred ending positions (Set A) (in blue) and fragments ending on the maternal-preferred ending positions (Set X) (in red). Shorter size distribution was observed for fragments ending on Set A positions compared with those ending on Set X positions. FIG. 23B shows the cumulative plot for the size distributions for the two sets of fragments. FIG. 23C shows the difference in the cumulative frequencies of the two sets of fragments ($\Delta S$) against fragment size. FIG. 23D shows $\Delta S$ against size with shifting of the Set A and Set X end positions to positions with larger genomic coordinates by zero to 5 bp. FIG. 23E shows $\Delta S$ against size with shifting of the Set A and Set X ending positions by zero to 5 bp in a reverse direction (positions with smaller genomic coordinates).

To further quantify the difference in the size distribution, the cumulative frequencies of the two curves are plotted (FIG. 23B). The difference in the two curves, represented by $\Delta S$, are plotted in FIG. 23C. We observed that the maximum difference was observed at 166 bp. This is consistent with the previous reports that the maximal difference between fetal- and maternal-derived DNA could be observed at 166 bp (Yu et al. Proc Natl Acad Sci USA. 2014; 111:8583-8). The present findings suggested that there was an enrichment of fetal-dervied DNA for fragments ending on the fetal-preferred ending positions (Set A) compared with those ending on maternal-preferred ending positions (Set X).

We further investigated the specificity of these ending positions by shifting the Set A and Set X ending positions by 1 to 5 bp upstream or downstream the genome. The $\Delta S$ values are plotted against size with the shifting of Set A and Set X ending positions in both directions (FIGS. 23D and 23E). Positive numbers of the shift represent the shifting to a position with a larger genomic coordinate (FIG. 23D) and negative numbers of the shift represent the shifting to a position with a smaller genomic coordinate (FIG. 23E). The shifting of the fetal- and maternal-preferred positions even by 1 bp would significantly reduce the size difference between DNA fragments ending on these two sets of positions ($\Delta S$). The shifting of 5 bp almost completely eliminated the size difference. These results suggested that the reads ending at those alternative positions were not as fetal- or maternal-specific than the reads ending at those preferred ending positons identified by our algorithm. These data further support our interpretation that plasma or cell-free DNA molecules fragment or are cleaved very precisely at those preferred end positions. In other words, there the non-random cell-free DNA fragmentation process is precise down to the level of specific nucleotides.

Then, we analyzed the pooled sequenced reads from the 26 first trimester plasma samples used for fetal DNA fraction analysis. Shorter size distribution was observed for fragments ending on Set A positions compared with those ending on Set X positions (FIG. 24A).

FIG. 24A shows plasma DNA size distributions in a pooled plasma DNA sample from 26 first trimester pregnant women for fragments ending on the fetal-preferred ending positions (Set A) (in blue) and fragments ending on the maternal-preferred ending positions (Set X) (in red). Shorter size distribution was observed for fragments ending on Set A positions compared with those ending on Set X positions. FIG. 24B shows the cumulative plot for the size distributions for the two sets of fragments. FIG. 24C shows the difference in the cumulative frequencies of the two sets of fragments (ΔS) against fragment size. FIG. 24D shows ΔS against size with shifting of the Set A and Set X positions by zero to 5 bp (larger genomic coordinates). FIG. 24E shows ΔS against size with shifting of the Set A and Set X positions by zero to 5 bp in a reverse direction (smaller genomic coordinates). The size difference between the plasma DNA fragments ending on the two sets of positions (ΔS) would reduce with the shifting of these positions, indicating that these positions would be precise to a single nucleotide level.

B. Cancer Example

The same strategy can also be applied for the analysis of preferred ending positions for cancer-derived fragments. In this example, we sequenced the plasma (220×coverage), buffy coat (48×) and tumor tissue (45×) of a patient suffering from hepatocellular carcinoma (HCC). The mutational profile of the patient was obtained by comparing the genotypes of the tumor tissue and the buffy coat. To determine the preferred ending positions for cancer-derived plasma DNA fragments, we analyzed the plasma DNA fragments carrying the cancer mutations. As shown in FIGS. 24A-24E, the fragmentation pattern of plasma DNA in the HCC patient is not random. Certain nucleotide positions have increased probability of being an end of a plasma DNA fragments.

1. Identification of Cancer-Specific Ending Positions

Figure 25:
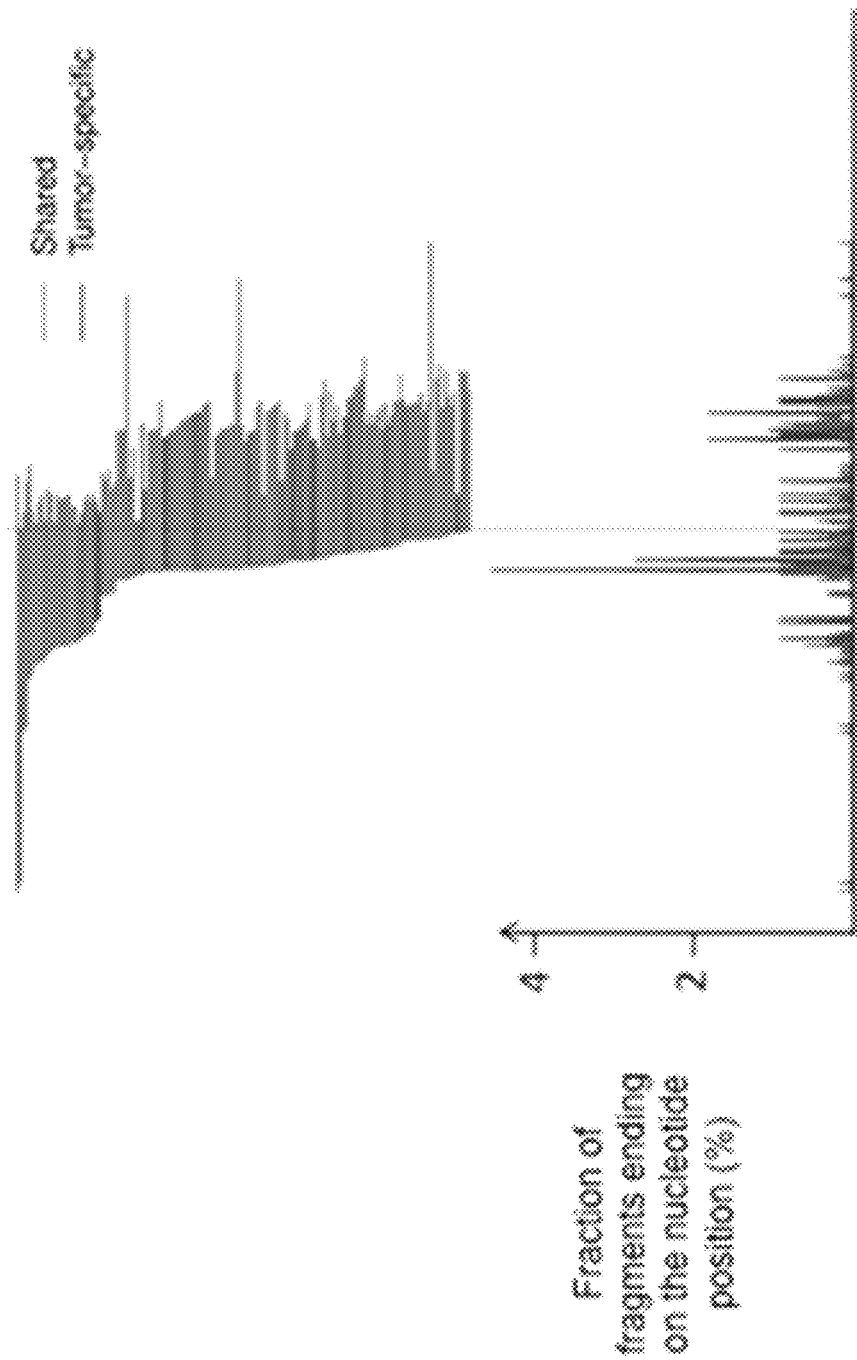
FIG. 25 shows an illustrative example of the non-random fragmentation patterns of plasma DNA of the HCC patient.

FIG. 25 shows an illustrative example of the non-random fragmentation patterns of plasma DNA of the HCC patient. On the upper part of the figure, each horizontal line represents one sequenced DNA fragment. The red and blue lines represent DNA fragments carrying the wildtype and mutant alleles, respectively. The ends of the DNA fragments represent the ending position of the sequenced read. The fragments are sorted according to the coordinate of the left outermost nucleotide (smallest genomic coordinate). On the lower part of figure, the percentage of fragments ending on a particular position is shown. The X-axis represents the genomic coordinates and the mutation is located at the center indicated by the dotted line.

We identified genomic positions that have increased probability of being an end of plasma DNA fragments carrying mutant alleles and wildtype alleles using Poisson probability distribution function as described previously. A p-value of 0.01 was used as the threshold. The reverse is also true, as described in PCT Application No. PCT/CN2016/073753, namely when a plasma DNA molecule with a specific end is identified, the SNP allele or mutation on the molecule is more likely to be cancer-derived, disease-associated or pregnancy-associated, depending which set of ends was used in the plasma DNA data interpretation.

Figure 26:
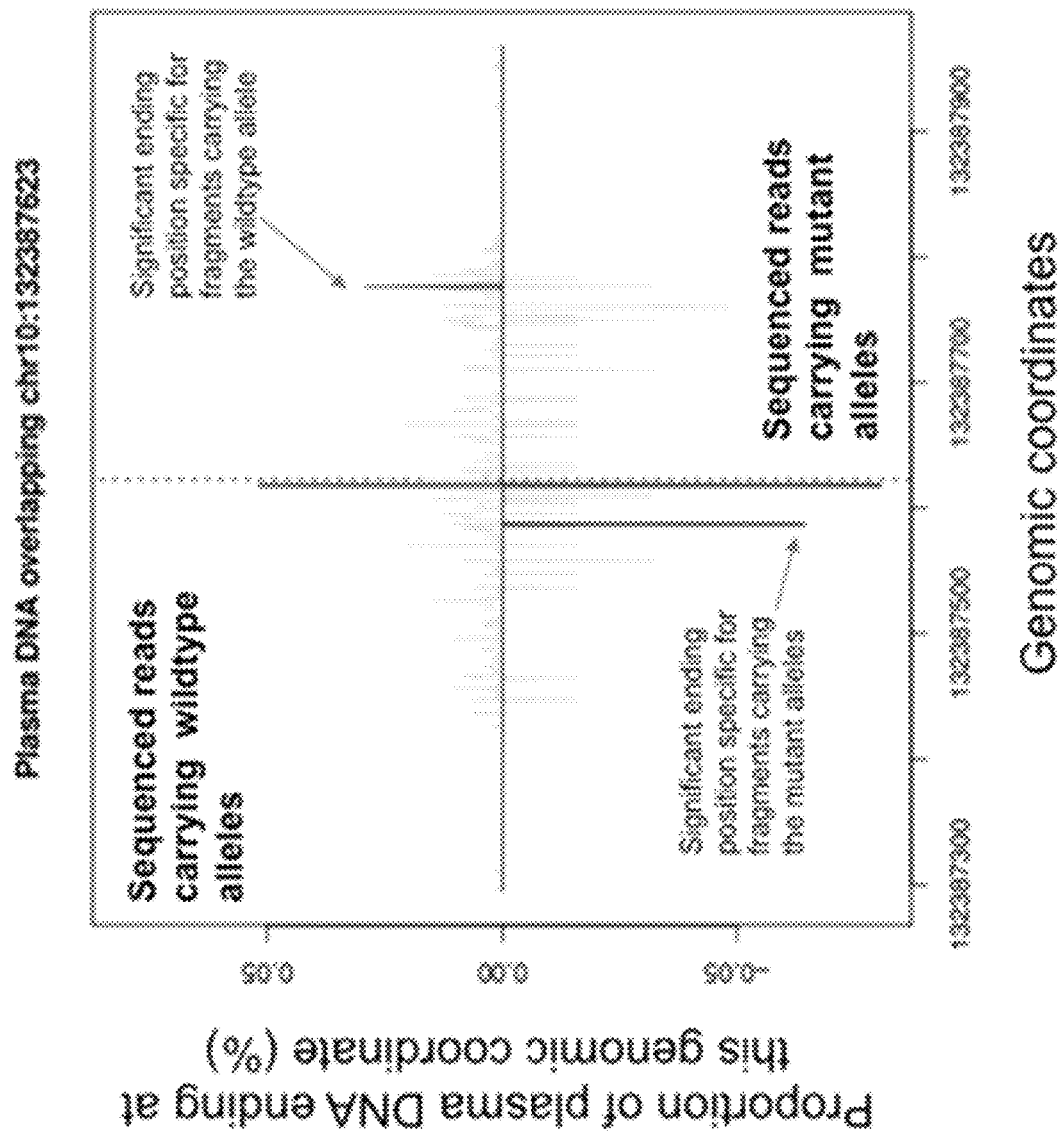
FIG. 26 is a plot of probability a genomic coordinate being an ending position of plasma DNA fragments across a region with a mutation site.

FIG. 26 is a plot of probability a genomic coordinate being an ending position of plasma DNA fragments across a region with a mutation site. Results for nucleotide positions with a significantly increased probability of being an end of plasma DNA fragments carrying a wildtype allele and a mutant allele are shown in red and blue, respectively. The X-axis represents the genomic coordinates and the mutation is located at the center indicated by the dotted line. As shown, there are coordinates that have a high rate of occurrence of ending positions for just the mutant-specific allele, for just the wildtype allele, and some are common to both.

Figure 27A:
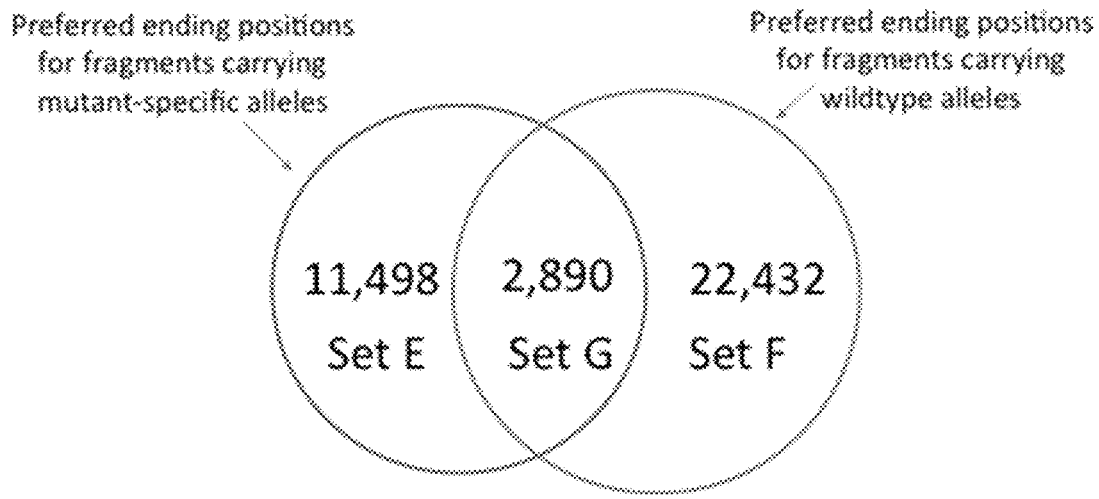
FIG. 27A shows an analysis of ending positions for plasma DNA fragments across genomic positions where mutations were present in the tumor tissue.

FIG. 27A shows an analysis of ending positions for plasma DNA fragments across genomic positions where mutations were present in the tumor tissue. Set E included preferred ending positions for fragments carrying mutant alleles. Set F included preferred ending positions for fragments carrying wildtype alleles. Set G included preferred ending positions for both types of plasma DNA fragments.

2. Using Recurrent Ending Positions to Deduce Tumor DNA Fraction

As Set E positions were preferred ending sites for cancer-derived DNA and Set F positions were preferred ending sites for background DNA predominantly derived from non-tumor tissues, we hypothesize that the ratio between the fragments ending on these two set of positions would correlate with the DNA derived from the tumor. Thus, we analyzed the plasma of 71 HCC patients whose plasma contained at least 1% of tumor-derived DNA. These patients were previously analyzed for copy number aberrations in plasma DNA and the tumor DNA fractions were estimated by the magnitude of the copy number aberrations. (Jiang et al. Proc Natl Acad Sci USA. 2015; 112:E1317-25). The ratio between the fragments ending on these two sets of positions ($Ratio_{M/WT}$) is defined as:

$$Ratio_{M/WT} = \frac{\text{No. of plasma } DNA \text{ fragments ending of Set } E \text{ positions}}{\text{No. of plasma } DNA \text{ fragments ending of Set } F \text{ positions}}$$

Figure 27B:
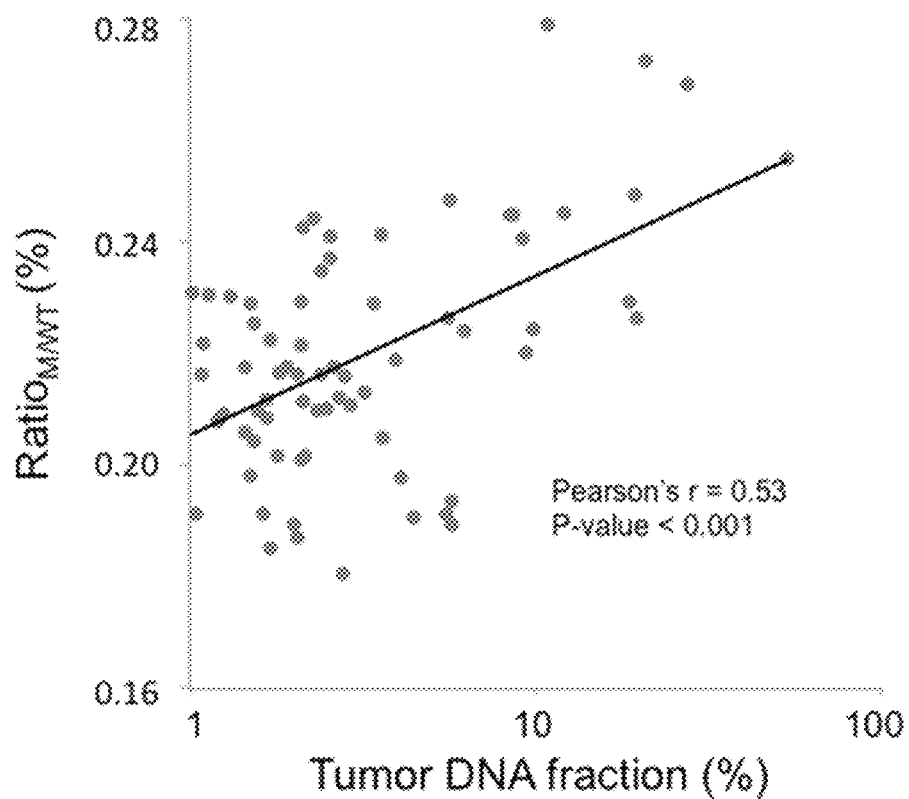
FIG. 27B shows a correlation between Ratio$_{M/WT}$ and tumor DNA fraction in the plasma of 71 HCC patients.

FIG. 27B shows a correlation between $Ratio_{M/WT}$ and tumor DNA fraction in the plasma of 71 HCC patients. A positive correlation between $Ratio_{M/WT}$ and the tumor DNA fraction in plasma was observed (r=0.53, p<0.001, Pearson correlation). These results suggest that the number of fragments ending on these cancer-preferred ending positions would be useful for predicting the amount of tumor-derived DNA in the plasma of cancer patients.

Some embodiments can increase the number of accessible informative cancer DNA fragments by the combined detection of a variety of cancer-specific or cancer-associated changes, for example, single nucleotide mutations, in combination with cancer-specific or cancer-associated DNA methylation signatures (e.g. location of 5-methycytosine and hydroxymethylation), cancer-specific or cancer-associated short plasma DNA molecules, cancer-specific or cancer-associated histone modification marks, and cancer-specific or cancer-associated plasma DNA end locations. Certain cancer-specific or cancer-associated changes may be used as filtering criteria in identifying mutations.

VII. Polymorphism-Independent End Position Analysis

In other embodiments, the preferred ending positions can be obtained by (A) comparing the ending positions of plasma DNA fragments from different individuals or (B) comparing the ending positions of plasma DNA fragments of samples from one individual taken at different time points.

A. Comparison Between the Preferred Ending Positions in Subjects Suffering from Different Pathological and Physiological Conditions 1. Use of Exclusive Sets Above Threshold Based on Poisson distribution probability function, we have identified genomic positions that had increased probability of being ending positions of plasma fragments for the pregnant woman and the HCC patient described in the previous sections. In this analysis, the null hypothesis is that all plasma DNA fragments would be fragmented randomly so that each genomic position would have an equal probability of being the end of plasma DNA fragments. The plasma DNA fragments were assumed to be 166 bp in size on average. The p-value was calculated as $$p\text{-value} = \text{Poisson}(N_{actual}, N_{predict})$$

where Poisson ( ) is the Poisson probability function; $N_{actual}$ is the actual number of reads ending at the particular nucleotide; and $$N_{predict} = \frac{\text{Total number of reads}}{3 \times 10^9 \times 166},$$

the $3 \times 10^9$ in the denominator represents the number of nucleotides in a genome.

The p-value was adjusted using the Benjamini and Hochberg correction (Bejamini et al. Journal of the Royal Statistical Society, 1995; 57:289-300) so as to achieve an expected false-discovery rate (FDR) of <1%.

Figure 28A:
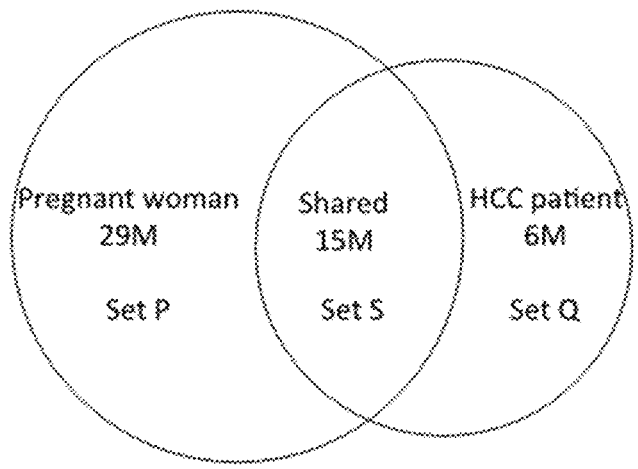
FIG. 28A shows the number of preferred ending positions for the plasma DNA of the pregnant woman and the HCC patient. Set P contained 29 million ending positions which were preferred in the pregnant woman.

FIG. 28A shows the number of preferred ending positions for the plasma DNA of the pregnant woman and the HCC patient. Set P contained 29 million ending positions which were preferred in the pregnant woman. Set Q contained 6 million ending positions which were preferred in the HCC patient. Set S is the overlapping set and contained 15 million ending positions.

We hypothesize that the fragments ending on the HCC preferred ending positions (Set Q) would be enriched for cancer-derived DNA when compared with those fragments ending on the pregnancy preferred ending positions (Set P). Thus, we calculated the $\text{Ratio}_{HCC/Preg}$ as $$\text{Ratio}_{HCC/Preg} = \frac{\text{No. of plasma } DNA \text{ fragments ending of Set } Q \text{ positions}}{\text{No. of plasma } DNA \text{ fragments ending of Set } P \text{ positions}}$$

and correlated this ratio with the tumor DNA fraction in the 71 HCC patients mentioned above.

Figure 28B:
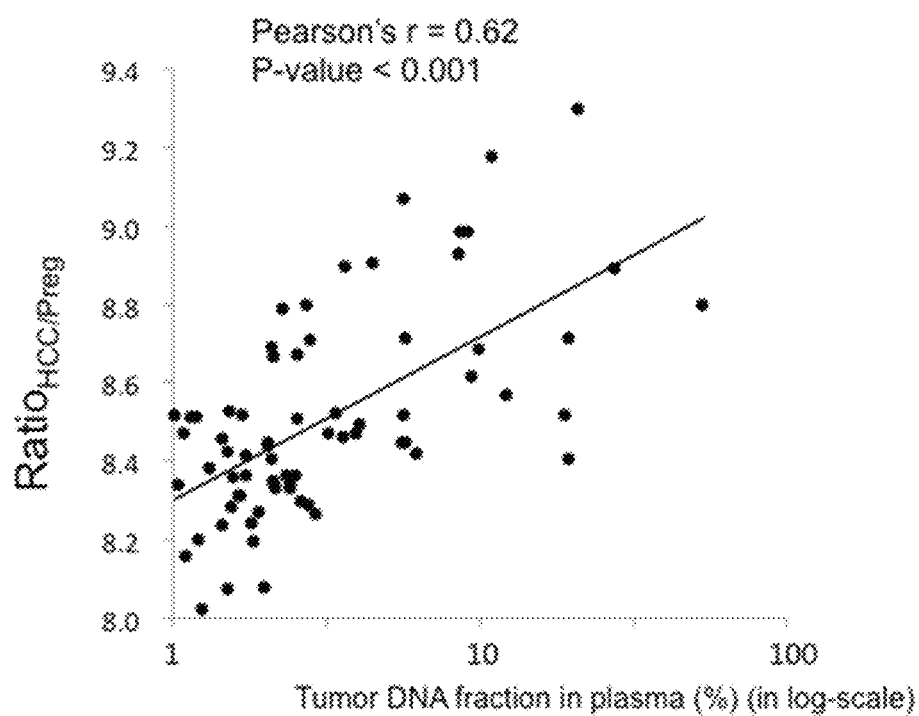
FIG. 28B shows a positive correlation was observed between Ratio$_{HCC/Preg}$ and tumor DNA fraction in plasma for the 71 HCC patients.

FIG. 28B shows a positive correlation was observed between $\text{Ratio}_{HCC/Preg}$ and tumor DNA fraction in plasma for the 71 HCC patients. These results suggest that the number or proportion of fragments ending on the preferred ending sites of a specific condition could be useful for detecting the condition or to quantify the amount of DNA released from the diseased organ.

2. Use of Set of Genomic Positions with Higher Ending Rate

Figure 29A:
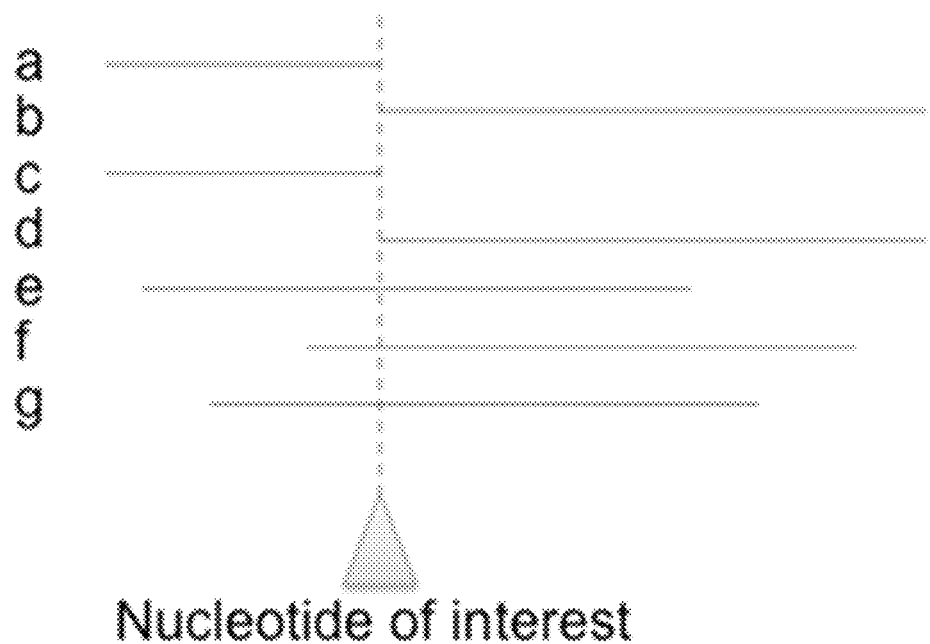
FIG. 29A shows an illustration of the concept of preferred end termination ratio (PETR). Each line represents one plasma DNA fragment.

In another embodiment, the preferred ending sites can be identified by determining the ratio between the number of fragments ending on such a position and the number of fragments covering the position but not ending on it. FIG. 29A illustrates the calculation of preferred end termination ratio (PETR).

$$PETR = \frac{\text{No. of } DNA \text{ fragments end on the nucleotide}}{\text{No. of } DNA \text{ fragments covering the nucleotide but not end on it}}$$

FIG. 29A shows an illustration of the concept of PETR. Each line represents one plasma DNA fragment. These fragments are labeled as a to g. Fragments a, b, c and d terminated on the nucleotide of interest. Fragments e, f and g cover the nucleotide of interest but do not end on such position. In this illustrative example, PETR equals to 4/3, i.e. 1.33. In other embodiments, the denominator can be the number of DNA fragments covering the nucleotide, regardless of whether the DNA fragment ends on the position.

The calculation of PETR can be used to identify nucleotide positions that are preferred ends in individuals suffering from different disease conditions. The following example demonstrates the utility of PETR. The plasma samples of the previously mentioned HCC patient and a subject with chronic hepatitis B virus (HBV) infection but without a cancer (HBV carrier) were compared. The plasma DNA samples of the HBV carrier was sequenced to 215× haploid genome coverage. PETR was calculated for each genomic position for each subject. 7,350,067 genomic positions (Set H) were identified as having PETR at least 4 folds higher in the HCC patient compared with the HBV carrier. These positions had at least 4-fold increased chance of being an end of plasma DNA fragments in the HCC patient compared with the HBV carrier. Other fold differences can be used, e.g., 1.5 fold, 2 fold, and 3 fold.

Plasma samples from 11 independent HCC patients were further sequenced to a much lower sequencing depth. A mean of 28 million sequenced reads were obtained from these 11 plasma samples. The mean PETR at the 7,350,067 Set H positions were calculated for each of these 11 HCC patients and correlated with the tumor DNA fraction in plasma. The tumor DNA fraction in plasma was calculated based on the magnitude of the copy number aberrations in plasma as previously described (Chan et al. Proc Natl Acad Sci USA. 2015; 112:E1317-25).

Figure 29B:
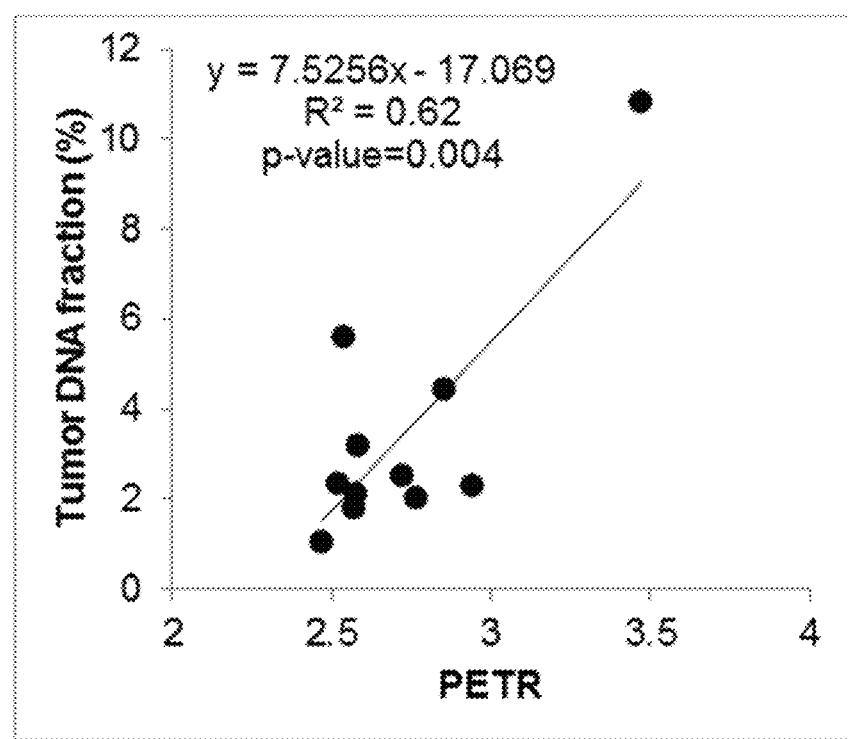
FIG. 29B shows a correlation between tumor DNA fraction in plasma with PETR at the Set H positions in 11 HCC patients.

FIG. 29B shows a correlation between tumor DNA fraction in plasma with PETR at the Set H positions in 11 HCC patients. A positive correlation between the two parameters could be observed suggesting that the average PETR at the HCC-preferred (Set H) positions would be useful to indicate the amount of tumor DNA in the plasma.

3. Confirmation of Ending Position being Liver-Related

To show that the preferred ending positions present in the HCC plasma DNA sample or in the HBV plasma DNA sample were liver-related, we searched for their presence in plasma samples collected from patients before and after surgical removal of HCC. The data are shown in Table 1. The pre- and post-surgical samples were sequenced to 17× and 20× haploid genomic coverages, respectively.

|  | HCC-preferred ending sites | HBV-preferred ending sites |
|---|---|---|
| Pre-surgery preferred ending sites in HCC 1 | 92 | 16 |
| Post-surgery preferred ending sites in HCC 1 | 5 | 4 |

Table 1 shows HCC-preferred ending positions and HBV-preferred ending positions in plasma sample collected before and after surgery to remove the liver tumor in the patient with HCC.

As could be seen in Table 1, there are reductions the number of both HCC- and HBV-preferred ending positions. The HBV data suggest that the majority of the preferred ending positions are liver-derived and their reduction is due to the reduction in the liver cell mass after surgery. There is therefore reduced release of liver-derived cell-free DNA molecules into plasma. It is interesting to note that there are more than 5-fold more HCC-preferred ending positions in the pre-surgical sample that disappeared post-surgically. Some of the preferred ends that showed post-surgical disappearance are liver-derived. Given the observation that many more HCC-preferred ends than the HBV-preferred ends were detected in the same pre-surgical sample suggests that the majority of those ends are HCC-specific and are not just generically liver-associated.

There are a number of applications that could be derived from these data. The data indicate that the detection of cell-free DNA or plasma DNA preferred ends could be used for cancer treatment monitoring. For example, the post-surgical reduction in the preferred ends indicates the success of the surgical removal of the HCC. If the tumor was not removed completely or successfully, the amount or quantity of plasma DNA preferred ends would not show a substantial reduction after the surgery. This is because the remaining tumor or metastatic foci would be a source for continued release of cell-free DNA or plasma DNA with the HCC-preferred ending positions. The data show that treatment monitoring based on the analysis of cell-free DNA preferred ends could be achieved at relatively shallow sequencing depth.

The data also show that tissue-associated or cancer associated plasma DNA preferred ending positions could be used to identify the tissue of pathology, including the tissue that is harboring the cancer. For example, one could use multiple sets of cell-free DNA preferred ends that are derived from different organs. One would then be able to determine the relative amounts of cell-free DNA originating from various tissues. Thus, this could serve as an approach for cell-free DNA tissue deconvolution. The tissue shown by this approach to have the most deviation (significantly increased or significantly reduced) from reference values established from control samples would be the organ or tissue with the pathology (e.g. inflammation or viral infection just like in the chronic hepatitis B virus carrier) or cancer.

Figure 30:
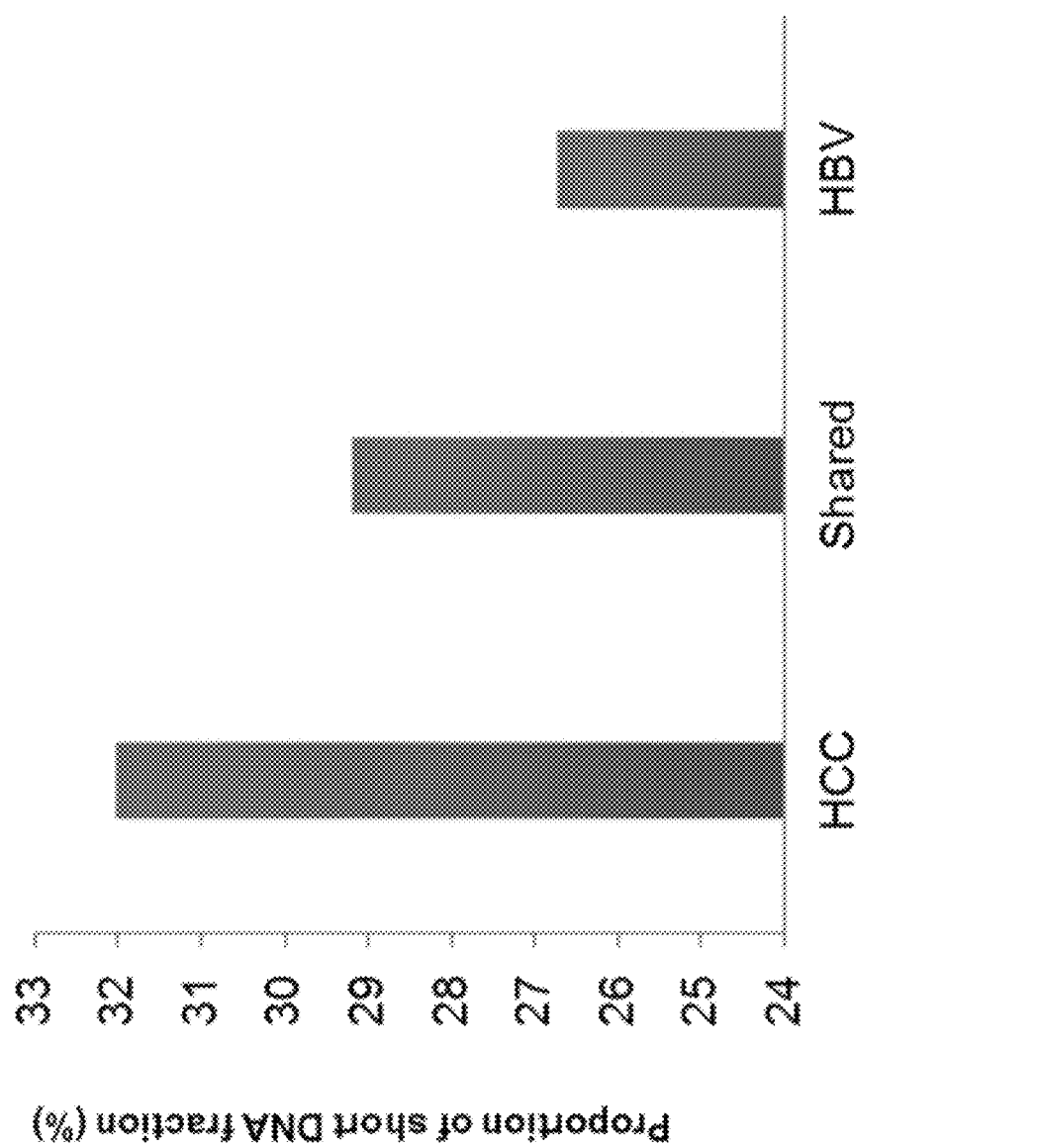
FIG. 30 shows a proportion of short DNA (<150 bp) detected among plasma DNA molecules ending with HCC-preferred ends, HBV-preferred ends or the shared ends.

Another piece of evidence to support that the plasma DNA HCC-preferred ends are cancer- or HCC-specific, we studied the size profile of plasma DNA molecules showing the HCC- or HBV-preferred ends (FIG. 30).

FIG. 30 shows a proportion of short DNA (<150 bp) detected among plasma DNA molecules ending with HCC-preferred ends, HBV-preferred ends or the shared ends. FIG. 30 shows that plasma DNA molecules exhibiting the HCC-preferred ends are generally much shorter (high proportion of short DNA) than those showing HBV-preferred ends. Jiang et al (Jiang et al. Proc Natl Acad Sci USA. 2015; 112:E1317-25) previously used another approach to show that tumor-derived plasma DNA molecules are shorter than the background non-tumor DNA. Because the plasma DNA molecules with the HCC-preferred ends are much shorter, they are highly likely to be tumor-derived. Thus, one might improve the chance of detecting the plasma DNA molecules with the HCC-preferred ends at even lower sequencing depth, one may enrich the sample with short DNA.

4. Window-Based Ending Rate

Figure 31A:
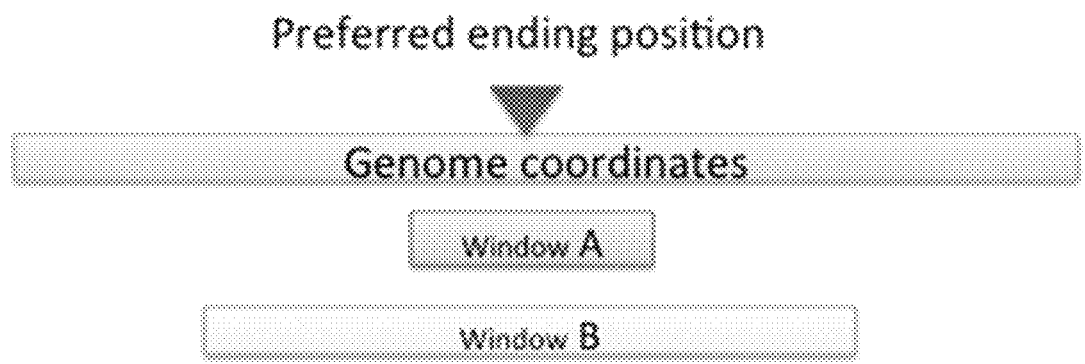
FIG. 31A shows an illustration of the principle of w-PETR. The value of w-PETR is calculated as the ratio between the number of DNA fragments ending within Window A and Window B.

In another embodiment, the HCC-preferred positions can be extended to include the neighboring nucleotides. FIG. 31A illustrates this method. The window-based PETR (w-PETR) ratio between the numbers of fragments ending within Window A and those ending within Window B would be determined. The size of Window A and Window B can be adjusted to achieve the desired performance. The performance of difference window sizes can be obtained experimentally. The size of Window A can be set, for example but not limited to 5 bp, 6 bp, 7 bp, 8 bp, 9 bp, 10 bp, 15 bp, 20 bp, 25 bp and 30 bp. The size of Window B would be larger than that of Window A and can be set, for example but not limited to 20 bp, 25 bp, 30 bp, 40 bp, 50 bp, 60 bp, 70 bp, 80 bp, 100 bp, 120 bp, 140 bp, 160 bp, 180 bp and 200 bp. In the follow illustrative example, the sizes of Window A and Window B were set as 20 bp and 150 bp, respectively.

FIG. 31A shows an illustration of the principle of w-PETR. The value of w-PETR is calculated as the ratio between the number of DNA fragments ending within Window A and Window B. Window A is larger and can be of width one when standard PETR is implemented. Window B is shown to be larger. Both windows are shown as being centered at the preferred ending position, but other positioning of the windows can be used. In some embodiments, window A can correspond to a preferred ending window.

Figure 31B:
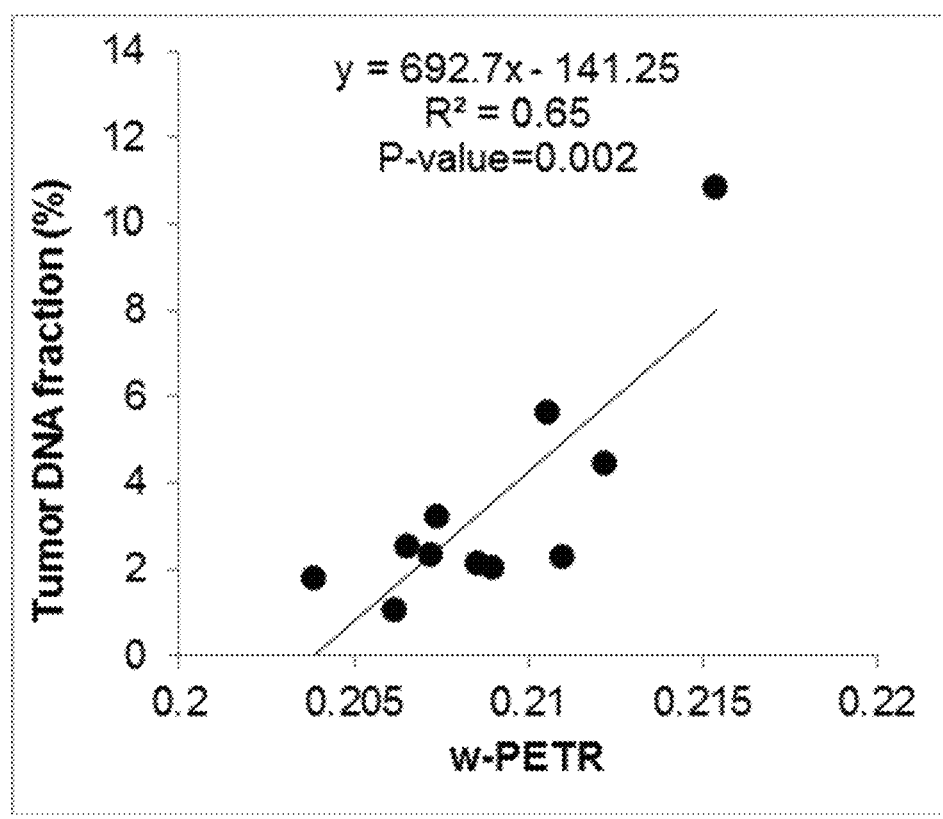
FIG. 31B shows a correlation between tumor DNA fraction and the value of w-PETR in the 11 HCC patients.

FIG. 31B shows a correlation between tumor DNA fraction and the value of w-PETR in the 11 HCC patients. These results suggest that w-PETR would be useful to determine the amount of tumor-derived DNA in the plasma of cancer patients.

5. Use of Highest Ending Positions Per Sample

Figure 32:
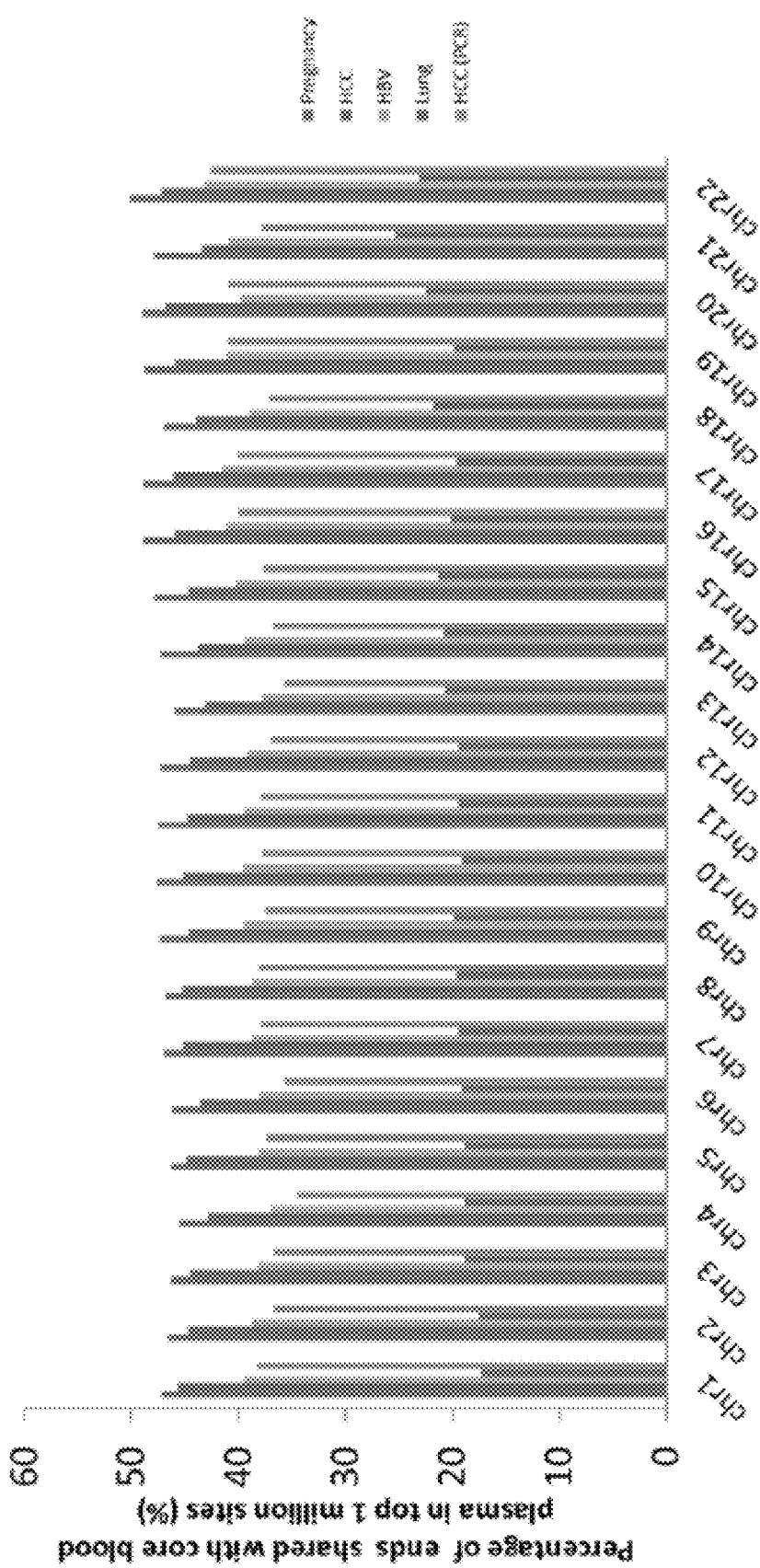
FIG. 32 shows the proportion of commonly shared preferred ending positions detected in plasma samples of each of the studied sample when compared with a cord blood plasma sample (210× haploid genome coverage).

We compared the top 1 million most frequently represented cell-free DNA ending positions between data from a pregnant woman, one chronic hepatitis B virus carrier (HBV), one lung cancer patient and two HCC patients. For the HCC patients, the sequencing library for one case (HCC) was prepared using a PCR-free protocol and the other sample (HCC (PCR) was prepared using a PCR-based protocol. All other samples are prepared using a PCR-free protocol. FIG. 32 shows the proportion of commonly shared preferred ending positions detected in plasma samples of each of the studied sample when compared with a cord blood plasma sample (210× haploid genome coverage).

FIG. 32 shows the proportion of commonly shared preferred ending positions detected in plasma samples of each of the studied sample when compared with a cord blood plasma sample (210× haploid genome coverage). Percentages are shown for the autosomes for each of pregnancy, HCC, HBV, lung cancer, and HCC detected using PCR.

The high level of commonality again supports the concept that plasma DNA fragmentation is not a random process. The HCC and HCC(PCR) data show that preferred ending position analysis could be performed using either library preparation protocols with or without PCR. It is interesting to note that there is still a proportion of plasma DNA molecules not showing common ends. The non-common ends are the preferred ends representative of the physiological state, e.g. pregnancy, the fetus or the placenta for the sample; or disease status, e.g. cancer. A more detailed comparison of the plasma DNA preferred ends is shown in FIG. 33.

Figure 33:
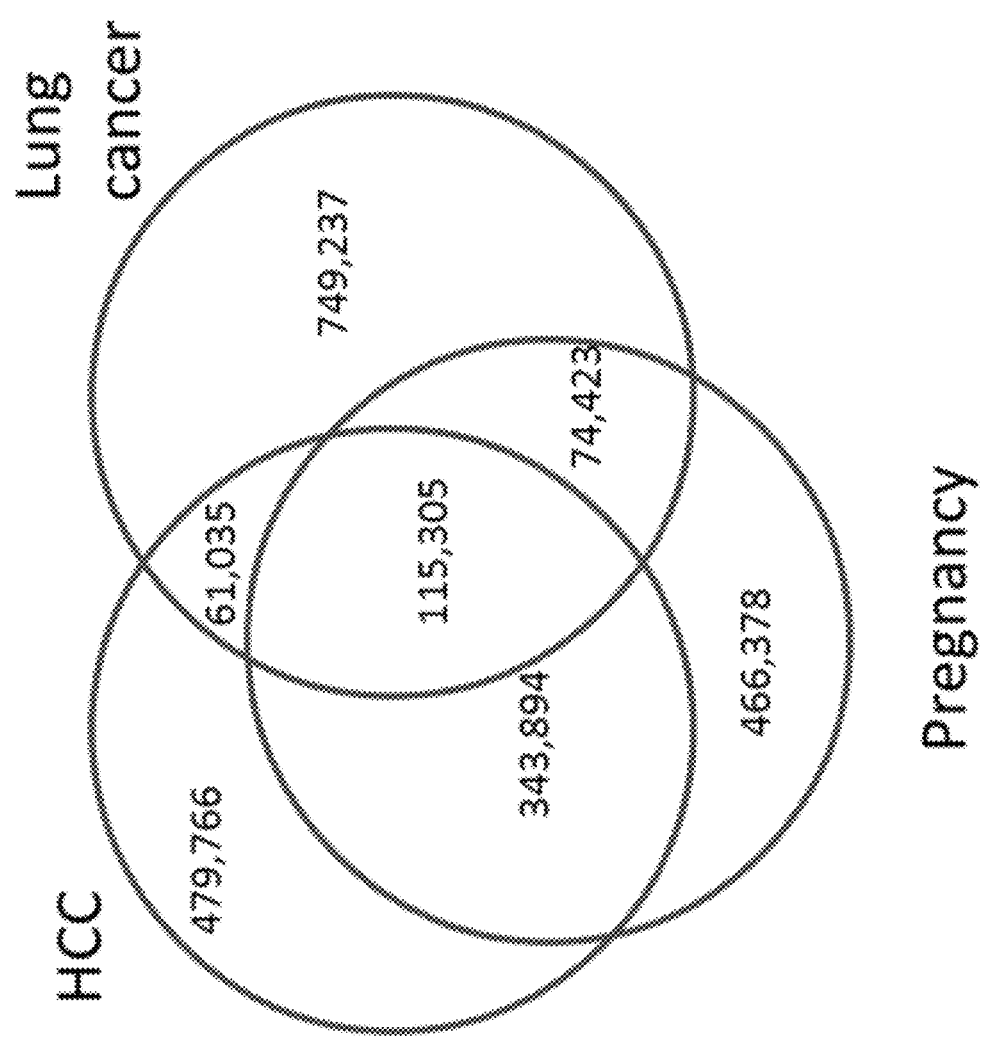
FIG. 33 shows a Venn diagram showing the number of preferred ending positions commonly observed in two or more samples as well as those that were only observed in any one sample.

FIG. 33 shows a Venn diagram showing the number of preferred ending positions commonly observed in two or more samples as well as those that were only observed in any one sample. Plasma DNA of lung cancer patient was sequenced at 175× haploid genome coverage.

It is noteworthy from FIG. 33 that 115,305 preferred ends are common across all three samples. These are likely to be derived from the major source of background plasma DNA, e,g, blood cells. The analysis also show that there were 61,035 preferred ending positions observed in the plasma samples of the HCC patient and the lung cancer patient. These preferred ends may be common to a number of cancers. Thus, they are cancer-derived. Whereas, there are ends that were only detected in the plasma DNA molecules of the HCC patient (479, 766 ends) or the lung cancer patient (749, 237 ends) but not both. These preferred ends therefore show a higher level of specificity. They are specific for a particular cancer tissue type. Based on the same rationale, one may be able to use similar mining strategies to identify ends specific for cancers of a particular organ and of a particular histology type. Plasma DNA molecules exhibiting the different classes of ends could be used for various applications. For example, one may aim to detect the HCC- or lung cancer-specific ends for the direct detection or screening of the specific cancer type. One may use the ends common to the HCC and lung cancer samples to detect or screen for cancer in general. One may use the most generic common ends as a denominator for normalization of the amount of disease-associated preferred ends detected. The generic common ends could also be detected for the purpose of screening for the sign of any disease (such as a general health screen). Positive findings for such a test could serve as an alert to visit a medical practitioner for more detailed investigation.

B. Comparison Between the Preferred Ending Positions Between Samples Collected from the Sample Individual but at Different Time Points The preferred ending positions of a particular condition can also be obtained by comparing the fragment ends of samples collected at different time points. For example, in a cancer patient, one plasma sample can be collected at the time of diagnosis and the other sample can be collected after treatment (e.g. after surgical resection of the tumor). The difference in the ending positions can potentially reflect the absence of the contribution of the cancer-derived DNA in the latter or the bodily response to the cancer. In another example, comparison can be made between the plasma samples collected from a pregnant woman taken before and after delivery of the fetus.

In the following example, the plasma samples collected from 8 pregnant women were analyzed. For each pregnant woman, a plasma samples was collected before delivery. In 6 of the 8 women, an additional plasma sample was collected at the time of delivery. Multiple samples were collected from the eight pregnant women at 6 hours after delivery onwards and a total of 28 post-delivery plasma samples were collected. The plasma DNA samples were sequenced to an average depth of 6.49× haploid genome coverage. The sequenced reads for the samples collected before delivery and at the time of delivery were pooled together for PETR analysis and these reads would be referred as "pre-delivery reads". The sequenced reads for the samples collected at 6 hours after delivery or later were pooled for PETR analysis and these reads would be referred as "post-delivery" reads. To identify the nucleotide positions that were preferred ends for pregnancy, positions with PETR at least 4 folds higher in the "pre-delivery" reads compared with "post-delivery" reads were retrieved. A total of 45,281 sites were identified.

An independent cohort of 8 first trimester pregnant women each carrying a male fetus was recruited and their plasma DNA was sequenced. A median of 20 million sequenced reads were obtained from these plasma DNA samples. The mean PETR values for the 45,281 sites was determined for each of the 8 pregnant women and these values were correlated with the fetal DNA fraction in plasma that was estimated from the proportion of reads aligning to the Y chromosome (Chiu et al. BMJ 2011; 342:c7401).

Figure 34A:
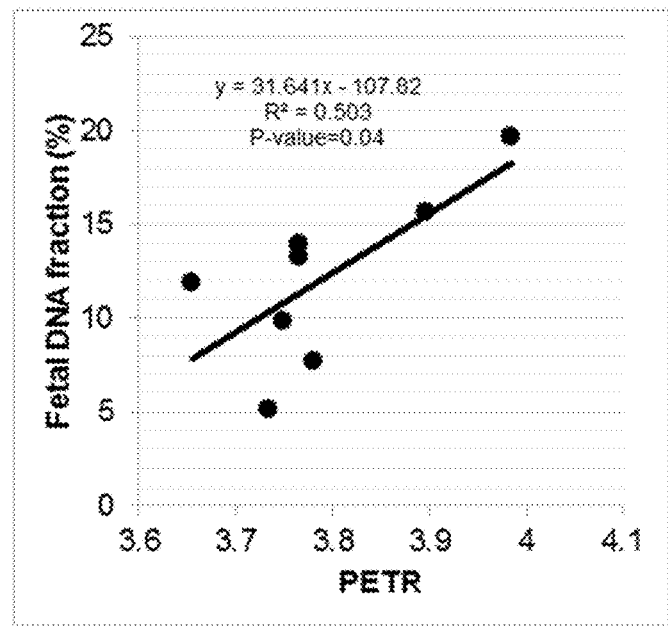
FIG. 34A shows a correlation between fetal DNA fraction in plasma and average PETR on the set of positions identified through the comparison between "pre-delivery" and "post-delivery" plasma DNA samples.

FIG. 34A shows a correlation between fetal DNA fraction in plasma and average PETR on the set of positions identified through the comparison between "pre-delivery" and "post-delivery" plasma DNA samples. These results suggest that the set of positions identified would be preferred for fetal-derived DNA and PETR analysis would be useful for quantifying fetal DNA in maternal plasma.

Similar to the approach described previously, we have applied the w-PETR analysis to this set of pregnancy-preferred positions. The size of Window A and Window B were set as 20 bp and 150 bp, respectively. In other embodiments, other window sizes can be used.

Figure 34B:
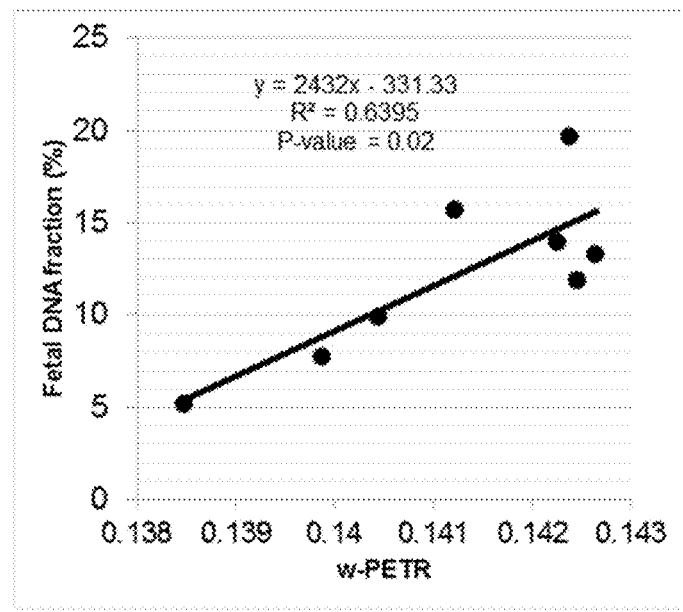
FIG. 34B shows a correlation between fetal DNA fraction in plasma and average w-PETR on the set of positions identified through the comparison between "pre-delivery" and "post-delivery" plasma DNA samples.

FIG. 34B shows a correlation between fetal DNA fraction in plasma and average w-PETR on the set of positions identified through the comparison between "pre-delivery" and "post-delivery" plasma DNA samples. These results suggest w-PETR analysis on these pregnancy-preferred positions would be useful for quantifying fetal DNA in maternal plasma.

C. Common Endpoints Among Same Condition

Figure 35A:
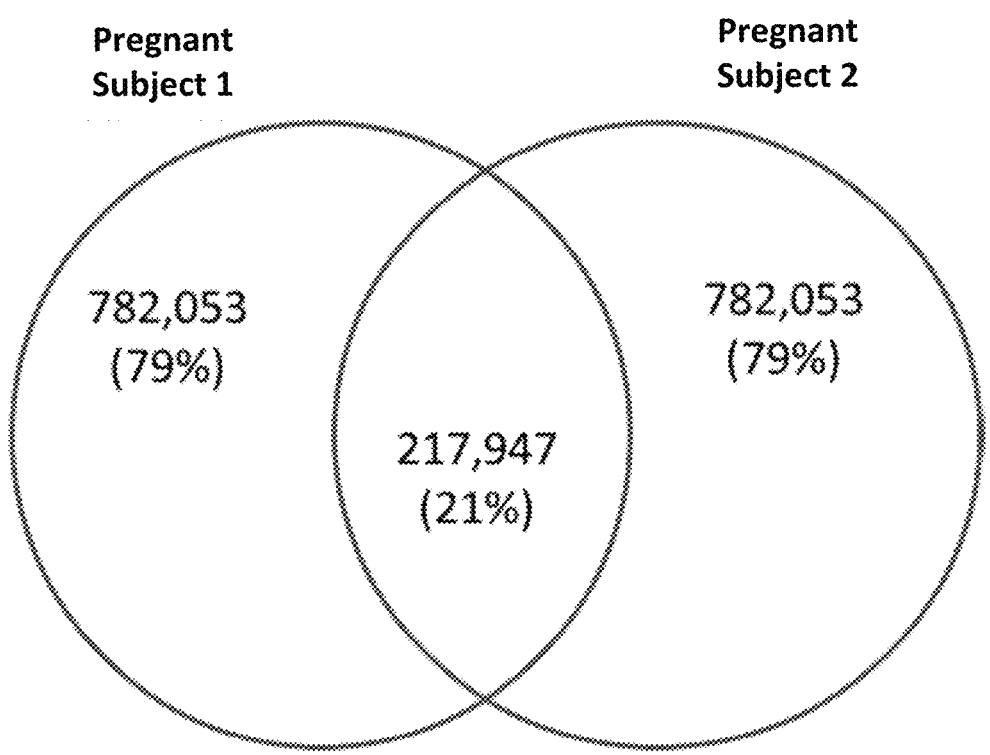
FIG. 35A shows the top 1 million most frequently observed plasma DNA preferred ending positions among two pregnant women at 18 weeks (pregnant subject 1) and 38 weeks of gestation (pregnant subject 2).

We compared the top 1 million most frequently observed preferred ending positions in plasma of two pregnant women (FIG. 35A).

FIG. 35A shows the top 1 million most frequently observed plasma DNA preferred ending positions among two pregnant women at 18 weeks (pregnant subject 1) and 38 weeks of gestation (pregnant subject 2). The data show that these women shared 217,947 preferred ends. Given both women are pregnant, these ends are derived from the fetus, the placenta or organs that have increased cell-death (generation of plasma DNA) during pregnancy. These markers are therefore most useful for the monitoring of the pregnancy or the well-being of the fetus.

We calculated the PETR value for this sample set. Interestingly, a correlation (Pearson'r=0.52, p-value <0.0001) between the PETR values of the plasma DNA molecules in the two maternal plasma samples was observed (FIG. 35B).

Figure 35B:
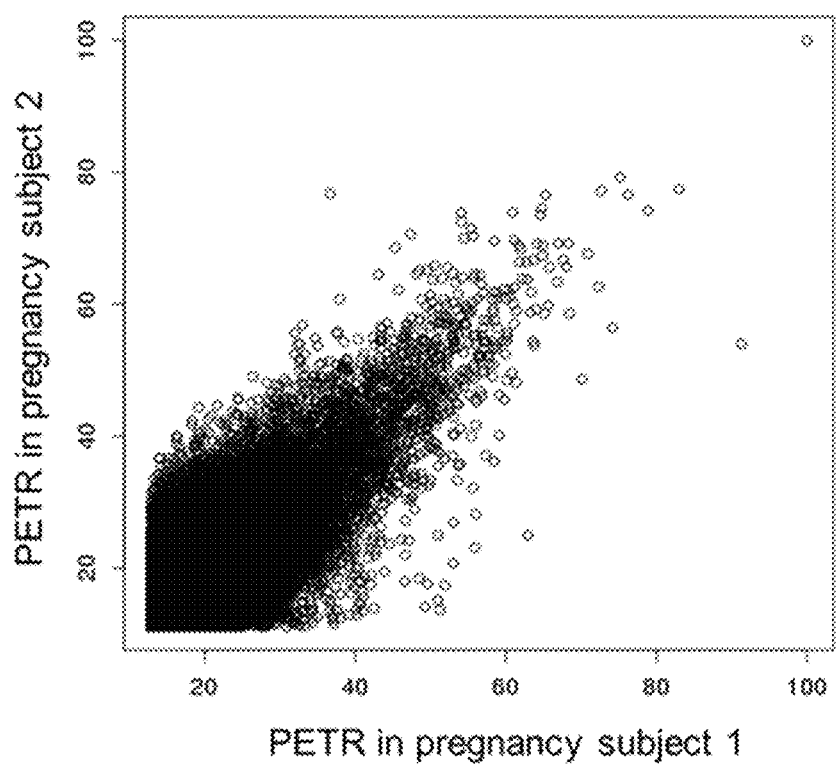
FIG. 35B shows a comparison of the PETR values of the top 1 million most frequently observed preferred ending positions in plasma of two pregnant women.

FIG. 35B shows a comparison of the PETR values of the top 1 million most frequently observed preferred ending positions in plasma of two pregnant women. The high degree of correlation once again indicates that plasma DNA fragmentation is highly orchestrated. Some ending sites are more "preferred" than others. Interestingly, even among the top 1 million "most preferred" sites, there is a relatively wide dynamic range of PETR. If one was to choose several or a subset of preferred ends for targeted detection, e.g. to test for disease, one should choose those commonly shared among the disease group of interest, ideally not observed or are less prevalent in the control group without disease and particularly those ending positions with very high PETR.

VIII. Methods Using Tissue-Specific Ending Positions

Figure 36:
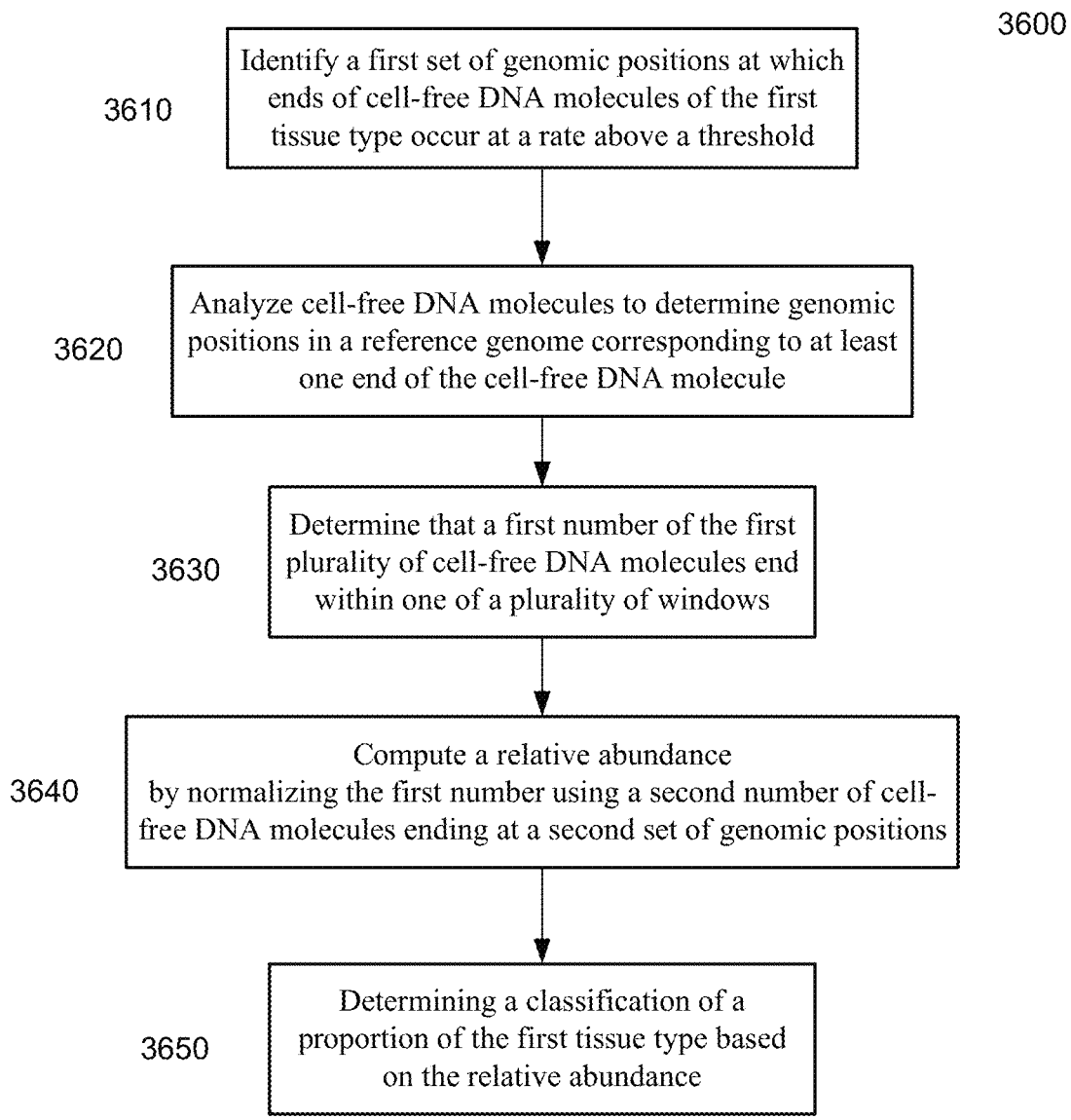
FIG. 36 is a flowchart of a method of analyzing a biological sample to determine a classification of a proportional contribution of the first tissue type in a mixture according to embodiments of the present invention.

FIG. 36 is a flowchart of a method 3600 of analyzing a biological sample to determine a classification of a proportional contribution of the first tissue type in a mixture according to embodiments of the present invention. The biological sample includes a mixture of cell-free DNA molecules from a plurality of tissues types that includes a first tissue type.

At block 3610, a first set of genomic positions at which ends of cell-free DNA molecules of the first tissue type occur at a rate above a threshold is identified. Further details about block 3610 in section X.B, as well as for other blocks performing identification of preferred ending positions. Details of other blocks of other methods can also be found in section X.

At block 3620, a first plurality of cell-free DNA molecules from the biological sample of a subject is analyzed. Analyzing a cell-free DNA molecule includes determining a genomic position in a reference genome corresponding to at least one end of the cell-free DNA molecule. Block 3620 can be performed in a similar manner as other blocks for analyzing cell-free DNA molecules, e.g., block 1320.

At block 3630, it is determined that a first number of the first plurality of cell-free DNA molecules end within one of a plurality of windows. The determination is performed based on the analyzing of the first plurality of cell-free DNA molecules. Each window includes at least one of the first set of genomic positions.

At block 3640, a relative abundance of the first plurality of cell-free DNA molecules ending within one of the plurality of windows is computed. The relative abundance can be determined by normalizing the first number of the first plurality of cell-free DNA molecules using a second number of cell-free DNA molecules. The second number of cell-free DNA molecules includes cell-free DNA molecules ending at a second set of genomic positions outside of the plurality of windows including the first set of genomic positions.

As described for FIG. 27A, the second set of genomic positions can be such that ends of cell-free DNA molecules of a second tissue type occur at a rate above the threshold in the at least one additional sample, where the second tissue type has a plurality of second tissue-specific alleles in the at least one additional sample. The second set of genomic positions can be determined using cell-free DNA molecules of the least one additional sample that include at least one of the plurality of second tissue-specific alleles. As Set G can be excluded from both set used to determine FIG. 27B, genomic positions at which ends of cell-free DNA molecules having a shared allele between the first tissue type and the second tissue type occur at a second rate above the threshold can be excluded from the first set of genomic positions and excluded from the second set of genomic positions.

At block 3650, the classification of the proportional contribution of the first tissue type is determined by comparing the relative abundance to one or more calibration values determined from one or more calibration samples whose proportional contributions of the first tissue type are known.

If the proportional contribution is high, further action can be performed, such as a therapeutic intervention or imaging of the subject (e.g., if the first tissue type corresponds to a tumor). For example, an investigation can use imaging modalities, e.g. computed tomography (CT) scan or magnetic resonance imaging (MRI), of the subject (entire subject or a specific part of the body (e.g. the thorax or abdomen), or specifically of the candidate organ) can be performed to confirm or rule out the presence of a tumor in the subject. If presence of a tumor is confirmed, treatment can be performed, e.g., surgery (by a knife or by radiation) or chemotherapy.

Treatment can be provided according to determined level of cancer, the identified mutations, and/or the tissue of origin. For example, an identified mutation (e.g., for polymorphic implementations) can be targeted with a particular drug or chemotherapy. The tissue of origin can be used to guide a surgery or any other form of treatment. And, the level of cancer can be used to determine how aggressive to be with any type of treatment, which may also be determined based on the level of cancer.

IX. Determining Genotype

Given that preferred ending positions can be determined for a particular tissue type, cell-free DNA molecules ending at such preferred ending positions have high likelihood of being from that tissue. In some situations, a particular tissue type in a cell-free DNA mixture can have a different genotype at a particular genomic position relative to other tissue types. For example, fetal tissue or tumor tissue can have a different genotype. As the cell-free DNA molecules have a high likelihood of being from the tissue type of interest, the cell-free DNA molecule ending at such a position can be analyzed to determine a genotype of the tissue type at that position. In this manner, the preferred ending position can be used as a filter to identify DNA from the tissue type.

A. Fetal Genotype

The information regarding the ending positions of the sequenced plasma DNA fragments can be used for determining which maternal allele has been inherited by the fetus from the pregnant woman. Here, we use a hypothetical example to illustrate the principle of this method. We assume that the genotypes of the mother, the father and the fetus are AT, TT and TT, respectively. To determine the fetal genotype, we need to determine if the fetus has inherited the A or the T allele from the mother. We have previously described a method called relative mutation dosage (RMD) analysis (Lun et al. Proc Natl Acad Sci USA 2008; 105: 19920-5). In this method, the dosage of the two maternal alleles in the maternal plasma would be compared. If the fetus has inherited the maternal T allele, the fetus would be homozygous for the T allele. In this scenario, the T allele would be overrepresented in the maternal plasma compared with the A allele. On the other hand, if the fetus has inherited the A allele from the mother, the genotype of the fetus would be AT. In this scenario, the A and T alleles would be present in approximately the same dosage in the maternal plasma because both the mother and the fetus would be heterozygous for AT. Thus, in RMD analysis, the relative dosage of the two maternal alleles in the maternal plasma would be compared. The ending positions of the sequenced reads can be analyzed for improving the accuracy of the RMD approach.

Figure 37:
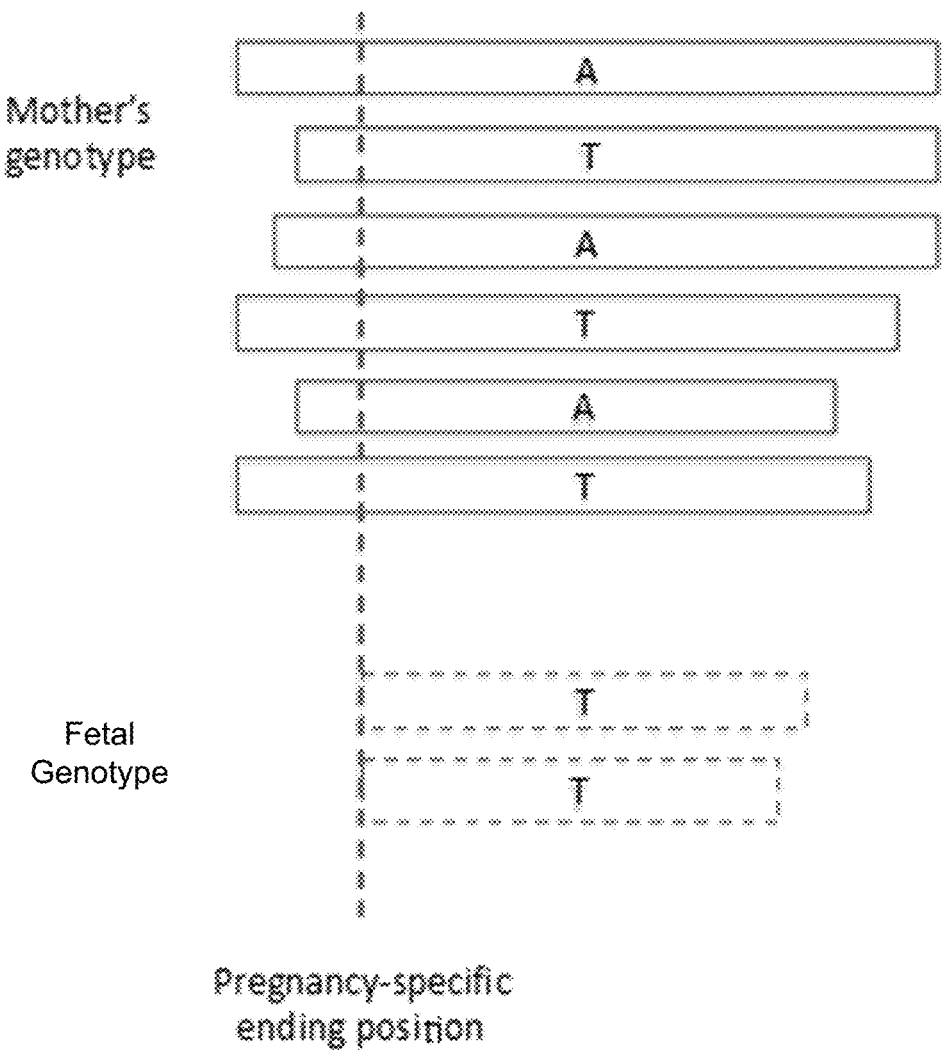
FIG. 37 shows maternal plasma DNA molecules carrying different alleles as they are aligned to a reference genome near a fetal-preferred ending position.

FIG. 37 shows maternal plasma DNA molecules carrying different alleles as they are aligned to a reference genome near a fetal-specific ending position. Molecules in solid lines are derived from the mother and the molecules in dotted lines are derived from the fetus. The fetal DNA molecules are more likely to end on the pregnancy-specific ending positions. In one embodiment, the molecules ending on the pregnancy-specific ending positions can be given more weight in the RMD analysis. In another embodiment, only plasma DNA fragments ending on pregnancy-specific positions are used for downstream analysis. This selection can potentially enrich the fetally derived plasma DNA fragments for downstream analysis.

FIG. 37 shows plasma DNA molecules in a pregnant woman whose genotype is AT. The DNA fragments derived from maternal tissues are in solid line and the DNA fragments derived from the fetus are in dotted line. The fetal DNA molecules are more likely to end on the pregnancy-specific ending position.

In this illustrative example, both of the two molecules ending on the pregnancy-specific ending position carry the T allele. In one embodiment, only the two molecules ending on the pregnancy-specific ending position were used for downstream analysis and the fetal genotype would be deduced as TT. In another embodiment, the two fetally derived molecules carrying the T allele would be given a higher weigh in the RMD analysis because these two molecules ended on a pregnancy-specific ending position. Different weight can be given to the molecules ending on the pregnancy-specific ending positions, for example but not limited to 1.1, 1.2, 1.3, 1.4, 1.5, 2, 2.5, 3 and 3.5.

As an example, the criteria for determining whether a locus is heterozygous can be a threshold of two alleles each appearing in at least a predetermined percentage (e.g., 30% or 40%) of reads aligned to the locus. If one nucleotide appears at a sufficient percentage (e.g., 70% or greater) then the locus can be determined to be homozygous in the CG.

B. Cancer Genotype

A similar technique can be performed for cancer-specific ending positions. For example, a cancer-preferred ending position can be identified as described above. The cell-free DNA molecules ending on the cancer-preferred ending position can be identified and analyzed. The base corresponding (e.g., aligned) to this position can be determined for each cell-free DNA molecule of this set, and the percentages of the total bases can be computed for each base. For example, a percentage of Cs seen on the cell-free DNA molecules ending at the position can be determined. If C is not seen in the healthy tissue of the subject, then C can be identified as a mutation if a sufficient number of Cs are identified, e.g., above a threshold number, which can depend on the measured tumor DNA fraction in the sample.

C. Filtering Techniques

Other criteria besides using an ending position can be used to filter for cell-free DNA molecules that are from the tumor tissue. The other criteria can also be used for the fetal scenario.

The specificity in identifying a cancer genotype (e.g., including a cancer-specific mutation) and any tests using such genotypes (e.g., use of mutational load to determine a level of cancer) can be improved by applying filtering criteria to loci where one or more sequence reads having a mutation have been aligned. As an example for cancer, high specificity can be achieved by scoring a genetic or genomic signature as positive only when there is high confidence that it is cancer associated. This could be achieved by minimizing the number of sequencing and alignment errors that may be misidentified as a mutation, e.g., by comparing to the genomic profile of a group of healthy controls, and/or may be achieved by comparing with the person's own constitutional DNA and/or may be achieved by comparing with the person's genomic profile at an earlier time.

Various criteria can be applied as filtering criteria to assess the likelihood of a cell-free DNA fragment being derived from the tumor and hence qualify to be an informative cancer DNA fragment. Each filtering criterion could be used individually, independently, collectively with equal weighting or different weightings, or serially in a specified order, or conditionally depending on the results of the prior filtering steps. For conditional usage, a Bayesian-based approach can be used, as well as a classification or decision tree based approach. An individual use of a criterion can mean using just one criterion. An independent use may involve more than one filtering criterion, but each filtering criterion does not depend on the application of another filtering criterion (e.g., parallel application can be performed), in contrast to a serial application in specific orders. As an example of collective usage using weightings, machine learning techniques can be used. For example, supervised learning can use measured mutational loads of samples with known classifications to train any models. Sequencing data from a large number of individuals (e.g. hundreds, thousands, or millions) can be used to train the models. In a simpler form, such known samples can be used to determine threshold values for one or more scores determined from the filtering criteria to determine whether a mutation is valid or not.

A DNA fragment could be given a higher weighting of informativeness or cancer-specificity if it shows more than one cancer-specific change. For example, many cancers are globally hypomethylated, especially at the non-promoter regions. Cancer DNA has been shown to be shorter than the non-cancer DNA in plasma. Tumor-derived plasma DNA fragments tend to fragment at some specific locations. Therefore, a plasma DNA fragment that is short in size (for example <150 bp) (Jiang et al. Proc Natl Acad Sci USA 2015; 112: E1317-1325), with one or both ends that fall on cancer-associated end locations, shows a single nucleotide mutation, and localizes to a non-promoter region, and has a hypomethylated CpG site would be deemed as more likely to be cancer-associated. The detection of hypomethylated DNA could be achieved with the use of bisulfite DNA conversion or direct single molecule sequencing that could distinguish methyl-cytosine from non-methyl-cytosine. In this application, we describe processes, protocols and steps to increase the specificity in the identification of informative cancer DNA fragments. For example, one or more filtering criteria can be used to increase the specificity. For example, one or more filtering criteria can be used to increase the specificity, such as to about at least a specificity of 80%, 90%, 95% or 99%.

1. Use of Plasma DNA End Location

As described above, filtering of potential cancer-specific or cancer-associated or fetal mutations based on the coordinate of the terminal nucleotide (ending position) can be performed. As described above, we have identified terminal locations of DNA fragments that are not random and that vary based on a tissue of origin. Thus, the terminal location can be used to determine a likelihood that a sequence read with a putative mutation is actually from fetal tissue or tumor tissue.

Recently, it has been shown that the fragmentation pattern of plasma DNA is non-random (Snyder et al. Cell 2016; 164: 57-68 and PCT WO 2016/015058 A2). The plasma DNA fragmentation pattern is influenced by nucleosomal positioning, transcription factor binding sites, DNase cutting or hypersensitive sites, expression profiles (Snyder et al. Cell 2016; 164: 57-68 and PCT WO 2016/015058; Ivanov et al. BMC Genomics 2015; 16 Suppl 13:S1) and DNA methylation profiles (Lun et al. Clin Chem 2013; 59: 1583-1594) in the genome of the cells that have contributed the plasma DNA molecules. Thus, the fragmentation patterns are different for cells of different tissue origins. While there are genomic regions that show more frequent fragments, the actual plasma DNA cutting sites within the region could still be random.

We hypothesized that different tissues are associated with the release of plasma DNA fragments that have different cutting sites, or end locations. In other words, even the specific cutting sites are non-random. Indeed, we show that a subset of plasma DNA molecules in cancer patients show different end locations than patients without cancer. Some embodiments can use plasma DNA molecules with such cancer-associated end locations as informative cancer DNA fragments, or use such end location information as a filtering criterion, e.g., along with one or more other filtering criteria. Thus, with the identification of such cancer-associated plasma DNA end locations, one could score the plasma DNA fragment as an informative cancer DNA fragment or attribute a differential weighting based on the nature of the end location of such a fragment. Such criteria can be used to assess the likelihood of the fragments originating from cancer, certain organs, or cancer of certain organs. Such weighting can be used to modify the contribution of a particular base of a particular DNA fragment to the total percentage of a particular base seen at the position.

Accordingly, the chance that a plasma DNA fragment is an informative cancer DNA fragment would be much higher if it shows a putative mutation and/or cancer-associated methylation change, as well as end locations that are cancer-associated. Various embodiments can also take into consideration the status of such a fragment and its length, or any combination of such and other parameters. For a plasma DNA fragment having two ends (or potentially up to four ends, as described in a following section), one can further modify the weighting for identifying it as a cancer-derived fragment by considering if one or both of its ends are associated with cancer or from a tissue type associated with cancer. In one embodiment, a similar approach based on end locations can also be used for detection mutations associated with other pathologies or biological processes (e.g. mutations due to the ageing process or mutations due to environmental mutagenic factors).

A similar approach can also be used for identifying de novo mutation of a fetus by sequencing the DNA in the plasma of a pregnant woman carrying the fetus. Hence, following the identification of end locations that are specific or relatively specific for the placenta, one can attribute a higher weighting to a putative fetal de novo mutation being a true one if such a DNA fragment in maternal plasma also carries a placental-specific or placental-enriched end location. As a plasma DNA fragment has two ends, one can further modify the weighting for identifying it as a fetal-derived fragment by considering if one or both of its ends are associated with the placenta.

As shown in FIG. 16, Plasma DNA fragments with terminal nucleotides ending exactly at the 536,772 HCC-specific ending positions would be more likely to be derived from the tumor. In contrast, plasma DNA fragments with terminal nucleotide ending exactly at the pregnancy-specific ending positions or the positions shared by the two cases would be less likely to be derived from the tumor, with pregnancy-specific ending positions potentially being less likely and given a lower weighting in any embodiment using weights.

Therefore, the list of top ending positions that are specific for the HCC case can be used to select the cancer-associated mutations, and the list of top ending positions that are specific for the pregnant case or shared by both cases can be used to filter out false-positive mutations. A similar procedure can be used for identifying fetal mutations and filtering out false-positive mutations for noninvasive prenatal testing.

In general, to identify such biologically-relevant plasma DNA end locations, plasma DNA samples from groups of individuals with different diseases or epidemiological backgrounds or physiological profiles could be compared with samples from another group of individuals without such diseases or backgrounds or profiles. In one embodiment, each of these samples could be sequenced deeply so that the common end positions of plasma DNA fragments could be identified within each sample. In another embodiment, the sequence data from the group of persons with complimentary profile could be pooled together for the identification of common end locations representative of the disease or physiological profile.

Each plasma DNA fragment in a sample could be interrogated individually and a likelihood score be assigned based on the end location. The likelihood score for a certain end location can be dependent on the separation in an amount of sequence reads (e.g., a percentage of sequence reads or other value normalized by sequencing depth across the samples) ending at the end location for the target individuals (e.g., cancer) relative to the amount of sequence reads ending for the control group. A larger separation would lead to a higher specificity, and thus a higher likelihood score can be applied. Therefore, classification of plasma DNA fragments with specific end locations into likely disease-associated or not, fetal or maternal, etc., could be performed.

Alternatively, plasma DNA fragments originating from the same region could be interpreted collectively, namely the rate of ending at a particular nucleotide can be calculated by normalizing to the sequencing depth. In this manner, certain nucleotides can be identified as being common end locations relative to other locations in the genome, e.g., just based on the analysis of one sample of a particular type, although more samples can be used. Therefore, classification of plasma DNA fragments with specific end locations into likely disease-associated or not, fetal, or maternal, etc., could be performed. For positions that show high frequencies of plasma DNA fragments with such biologically-relevant plasma DNA end locations, a determination could be made that such loci are enriched with the biologically-relevant DNA and thus be included as a group of plasma DNA fragments being of high likelihood as cancer-associated or fetus-specific or associated with other diseases or biological processes. The level of likelihood can be based on how high the rate is for a given nucleotide relative to other nucleotides, in a similar manner as comparisons across different groups, as described above.

2. Results

To illustrate the efficacy of this approach, potential cancer-associated mutations were identified directly from the plasma DNA sequencing data of the HCC patient. Single nucleotide changes that were present in the sequence reads of at least two plasma DNA fragments were considered as potential cancer-associated mutations. The tumor tissue was also sequenced and the mutations that were present in the tumor tissue were considered as true cancer-associated mutations.

On chromosome 8, a total of 20,065 potential mutations were identified from the plasma DNA sequencing data of the HCC patient without using the dynamic cutoff analysis. A sequence variant would be regarded as a potential mutation if the sequence variant was present in at least two sequenced DNA fragments. 884 true somatic mutations were identified from the sequencing result of the tumor tissue. The 20,065 putative mutations included 802 (91%) of the 884 real mutations. Thus, only 4% of the putative mutations were true somatic mutations in the tumor tissue giving a PPV of 4%.

To enhance the accuracy of detecting the somatic mutations, thereby leading to a cancer genotype, we used the following filtering algorithms based on the terminal nucleotide positions of the sequence reads carrying the putative mutations. (1). For any putative mutation, if there is at least one sequence read carrying the mutation and ending on HCC-specific ending positions, the mutation would be qualified for downstream mutational analysis. (2). A sequence read that carried a putative mutation but ended on any pregnancy-specific ending positions or the positions shared by both cases would be removed. A mutation would be qualified for downstream mutational analysis only if there were two or more sequence reads showing the same mutation after the removal of the reads based on this algorithm.

Applying both 1 and 2 filtering algorithms stated above, the results in table 2 were obtained. The effects of applying different filtering algorithms based on the position of the terminal nucleotides, or end locations, of the DNA fragments carrying the putative mutations.

TABLE 2

|  | No filter | Inclusion of mutations with HCC-specific ends (filter 1) | Removal of reads with shared or pregnancy-specific ends (filter 2) | Applying both filtering algorithms |
|---|---|---|---|---|
| No. of putative mutations identified | 20,065 | 1,526 | 2,823 | 484 |
| Percentage of true mutations detected | 91% | 29% | 88% | 40% |
| PPV | 4% | 17% | 28% | 71% |

There was a substantial improvement in the PPV by adopting any one of the three algorithms requiring the end locations being HCC-specific or the algorithm filtering out the pregnancy-specific or the shared positions. By applying both algorithms, the PPV increased to 71%.

Other number of HCC- and pregnancy-associated end locations can be identified for each chromosome, or indeed for another genomic region, or indeed for the entire genome, for example, but not limited to, 0.5 million, 2 million, 3 million, 4 million, 5 million, 6 million, 7 million, 8 million, 9 million or 10 million. In various embodiments, the most frequently seen end locations in plasma DNA molecules can be determined in one or more cohorts of cancer patients, each cohort being of one cancer type. In addition, the most frequently end locations in plasma DNA molecules can be determined for subjects without cancer. In one embodiment, such patients with cancer and subjects without cancer can be further subdivided into groups with different clinical parameters, e.g. sex, smoking status, previous health (e.g. hepatitis status, diabetes, weight), etc.

As part of using such filtering criteria, statistical analysis can be used to identify the positions that have higher probability of being terminal nucleotides or end locations for circulating DNA for different physiological and pathological conditions. Examples of the statistical analyses include but not limited to the Student t-test, Chi-square test, and tests based on binomial distribution or Poisson distribution. For these statistical analyses, different p-value cutoffs can be used, for example but not limited to 0.05, 0.01, 0.005, 0.001, and 0.0001. The p-value cutoffs can also be adjusted for multiple comparisons.

D. Method for Determining Genotype

Figure 38:
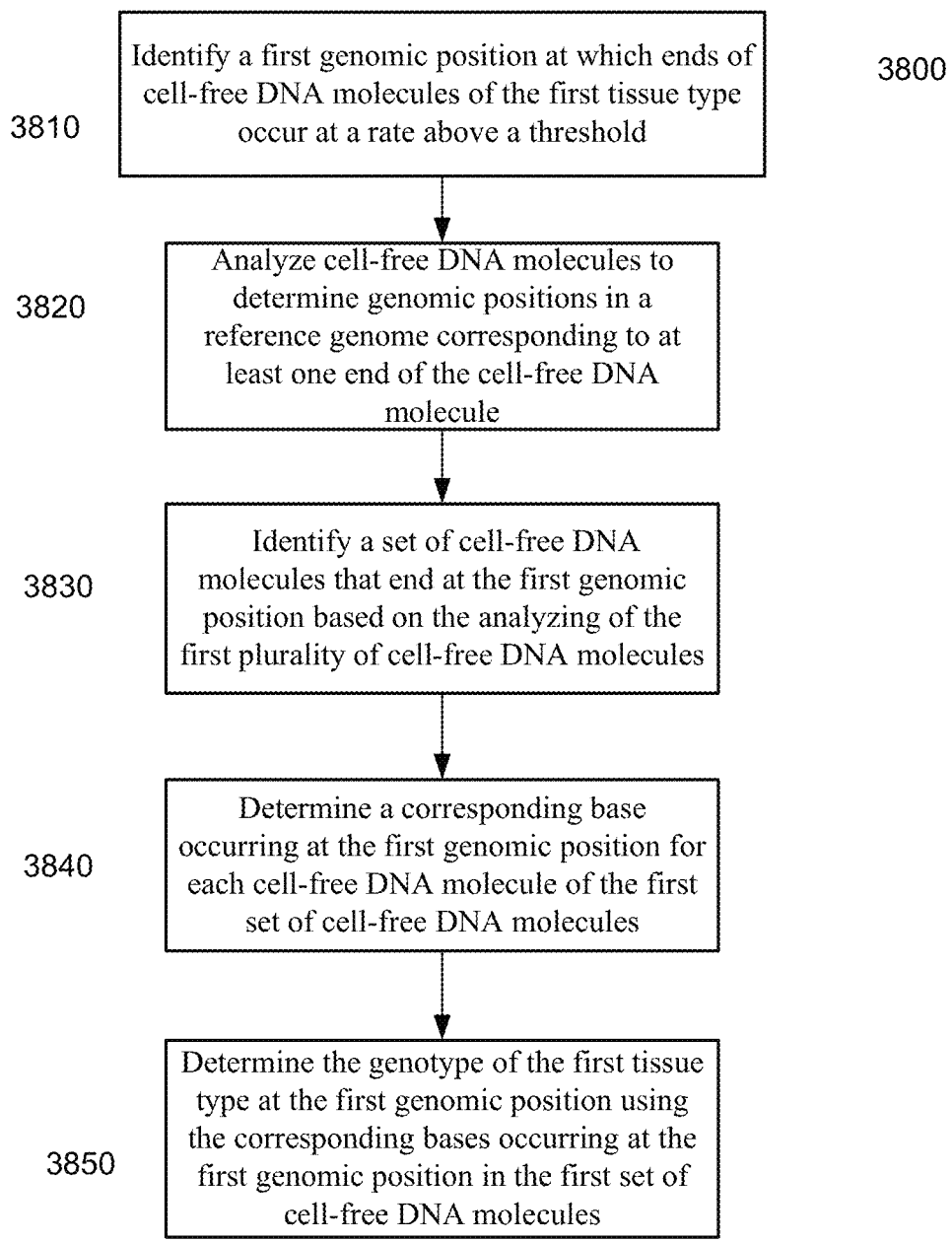
FIG. 38 is a flowchart of a method 3800 of analyzing a biological sample to determine a genotype of the first tissue type according to embodiments of the present invention.

FIG. 38 is a flowchart of a method 3800 of analyzing a biological sample to determine a genotype of the first tissue type according to embodiments of the present invention. The biological sample includes a mixture of cell-free DNA molecules from a plurality of tissues types that includes the first tissue type. The first tissue type potentially has a different genotype than other tissue types of the plurality of tissue types. Genotypes at multiple genomic positions can be determined.

At block 3810, a first genomic position at which ends of cell-free DNA molecules of the first tissue type occur at a rate above a threshold is identified. Block 3810 can be performed in a similar manner as block 3610. Section X.B provides additional examples for performing block 3810.

At block 3820, a first plurality of cell-free DNA molecules from the biological sample of a subject is analyzed. Analyzing a cell-free DNA molecule includes determining a genomic position in a reference genome corresponding to at least one end of the cell-free DNA molecule. Block 3620 can be performed in a similar manner as other blocks for analyzing cell-free DNA molecules.

At block 3830, a set of cell-free DNA molecules that end at the first genomic position is identified based on the analyzing of the first plurality of cell-free DNA molecules. As examples, the set can be identified using alignment of sequence reads of detected probes having known ending positions. Other examples are provided herein.

In some embodiments, further filtering can be performed, e.g., as described above. For example, a size of a cell-free DNA molecule can be required to be less than a specified amount, e.g., as fetal tissue and tumor tissue are generally shorter than DNA fragments from healthy cells. In one implementation, the set of cell-free DNA molecules can be filtered to exclude or modify a weighting of at least one of the cell-free DNA molecules that end at the first genomic position. The genotype can be determined using a filtered set of cell-free DNA molecules.

In various embodiments, the filtering can use at last one of: a size of a cell-free DNA molecule, a methylation status of the cell-free DNA molecule at one or more positions (e.g., whether a CpG site is methylated or not methylated), and whether the cell-free DNA molecule covers one or more other genomic position at which ends of cell-free DNA molecules of the first tissue type occur at a rate above a threshold. The methylation status can provide a signature of the first tissue type, as described above.

At block 3840, for each cell-free DNA molecule of the set of cell-free DNA molecules, a corresponding base (nucleotide) occurring at the first genomic position is determined. The total number of molecules with each base can be determined and a percentage can be calculated for each base.

At block 3850, the genotype of the first tissue type at the first genomic position is determined using the corresponding bases occurring at the first genomic position in the set of cell-free DNA molecules. In various implementations, a high percentage of just one base (e.g., above 80%, 85%, or 90%) can indicate the genotype is homozygous for the base, while two bases having similar percentages (e.g., between 30-70%) can lead to a determination of the genotype being heterozygous. Accordingly, the percentages for each base can be compared to cutoff values to the genotype. In some embodiments, a cutoff value can be determined based on a proportional contribution of the first tissue type to the sample.

Thus, in some embodiments, determining the genotype of the first tissue type at the first genomic position can include determining a percentage contribution for each of a plurality of bases and comparing each of the percentage contributions to one or more cutoff values. In one example, a first cutoff value can correspond to a homozygous genotype of a first base when the percentage contribution of the first base is above the first cutoff value. IN another examples, a first cutoff value and a second cutoff value can correspond to a heterozygous genotype for a first base and a second base when the percentage contributions of the first base and the second base are above the first cutoff value and below the second cutoff value.

In some embodiments, a weighting can be performed for each cell-free DNA molecule in the set identified in block 3830. For example, if a likelihood that the cell-free DNA molecule is from the first tissue type is 80%, then 0.8 can be the weighting. The total contribution of all weightings for a particular base can summed to determine respective amounts for each base. The respective amounts can be used to determine a percentage contribution for each base, where the percentages can be used to determine the genotype.

Accordingly, the filtering can assign a weight to the cell-free DNA molecule corresponding to a likelihood that the cell-free DNA molecule is from the first tissue type. A weighted sum can be determined for each of a plurality of bases (e.g., just those detected, which may be 2, 3, or 4). If only one base is detected, then a homozygous genotype for that one base can be determined. A percentage contribution for each of the plurality of bases can be determined using the weighted sums, where the genotype is determined using the percentage contributions.

X. Further Details

Various embodiments described above identify preferred ending positions for particular tissues, where some of the preferred ending positions can be contiguous, thereby forming a preferred ending window. Different metrics can be used to identify rates of occurrence of cell-free DNA molecules at genomic windows (e.g., a genomic position for the smallest window). Further details about such operations are provided below, as well as details about determining an ending position of a cell-free DNA molecule in a reference genome. Such specific techniques can be used with embodiments described above.

A. Determination of Ending Position

When sequencing cell-free DNA molecules, there are various possibilities of the ending patterns of DNA fragments. There are generally four configurations of ends for plasma DNA: (A) A double stranded DNA molecule with two flushed ends; (B) A double strand DNA molecule with one flushed end, and one non-flushed end (showing each of the two scenarios, as either one of the two strands can protrude out); (C) A double strand DNA molecule with two non-flushed end, with different combinations of protruding ends; and (D) A single stranded DNA molecule.

For the configurations with non-flushed ends, there are different patterns depending on whether the 5' or the 3' end of the DNA molecule is protruded. For (B), the double-stranded DNA molecules has one flushed end and one non-flushed end. In an example B1, the 5' end is protruded and in an example B2, the 3' end is protruded. For (C), there are three possible patterns when both ends are non-flushed. In (C1), 5' end protrudes on both sides. In (C2), 3' end protrudes on both sides. In (C3), 5' end protrudes on one side and 3' end protrudes on the other side.

For sequencing, paired-end sequencing protocols commonly sequence one end of each of the stands. They are therefore considered double-stranded DNA sequencing protocols. When the two ends are not flushed, protocols can either cut nucleotides off or add nucleotides to the end to make them flushed. The Klenow fragment is an enzyme that can carry out such operations. Other protocols in the field use single-stranded DNA sequencing protocols.

Regardless of the specific technique used (including use of probes), as long as the ending positions are repeatable and show correlation, as is shown here, whether a true end of a DNA fragment is obtained in sequencing does not affect the results, as any offset is repeatable, and thus cancel out. Further, certain techniques can be used for identifying an ending position, as is described in the Terms section.

B. Identification of Tissue-Specific Ending Positions

As described above, in a particular tissue type, certain genomic regions have a greater variation for the likelihood that a cell-free DNA molecule will end on a particular position than for other regions. For example, liver tissue can have a region that is a DNase hypersensitivity site, but other tissues do not have that region as a DNase hypersensitivity site. Accordingly, certain positions within such a region will have a high number of cell-free DNA molecules ending on those positions relative to other positions. As examples, such positions can be identified as maximum in a rate of cell-free DNA molecules for a region known to have a high amount of cleavage for a particular tissue (thus, a high amplitude in the likelihood function), e.g., as described in section III. In other examples, the genomic positions can be identified where a left peak and right peak are sufficiently separate, e.g., as described in section IV.

In yet other examples, a difference in sets of high rate ending positions (e.g., rate above a threshold) for samples having and not having a condition (e.g., pregnancy or cancer, possibly of a particular type) can be used to identify preferred ending sites for a particular tissue type associated with the condition, e.g., as described with the use of Venn diagrams in sections V, VI, and VII. As yet other examples, a significantly higher rate in one sample with a condition than with another sample not having the condition can provide preferred ending sites of a particular tissue type. In various embodiments, some or all of such example techniques can be used together. The rate can be measured by any metric of relative abundance.

In some embodiments of above methods, a first set of genomic positions at which ends of cell-free DNA molecules of the first tissue type occur at a rate above a threshold can be identified in the following manner. A calibration sample can be analyzed in a similar manner as the test sample, where the two samples of a same type (e.g., plasma, serum, urine, etc.) and the calibration sample is known to include the first tissue type (e.g., fetal tissue from a sample of a pregnant female or tumor tissue of the liver for an HCC patient). A number of cell-free DNA molecules ending in a genomic window (e.g., of width one or more) can be compared to a reference value to determine whether a rate of ending positions is above a threshold for that position. In some embodiments, if the rate exceeds the reference value, each of the genomic positions within the first genomic window can be identified as having the rate be above the threshold when the corresponding number exceeds the reference value. Such a process can identify preferred ending windows, which include preferred ending positions.

The reference value can be such that only the top N genomic windows have a rate above the threshold. For example, the first set of genomic positions can have the highest N values for the corresponding numbers. As examples, N can be at least 10,000; 50,000; 100,000, 500, 000; 1,000,000; or 5,000,000.

As another example, the reference value can be an expected number of cell-free DNA molecules ending within the genomic window according to a probability distribution and an average length of cell-free DNA molecules in a sample, e.g., as described in section VI.A.1. A p-value can be determined using the corresponding number and the expected number, wherein the threshold corresponds to a cutoff p-value (e.g., 0.01). The p-value being less than the cutoff p-value indicates that the rate is above the threshold. As yet another another example, the reference value can include a measured number of cell-free DNA molecules ending within the genomic window from a sample identified as having a reduced amount of the first tissue type, e.g., as described for FIGS. 29A and 29B.

The genomic positions that satisfy the rate threshold are not necessarily added to the first set of genomic positions. Further filter criteria can be added. Examples of such filtering criteria are specified in section VI.A.3 and IX.C. For a filtering criteria of size, a size (e.g., length or mass) of cell-free DNA molecules can be measured, e.g., as described in U.S. Patent publications 2011/0276277, 2013/0040824, and 2013/0237431, all of which are incorporated by reference in their entirety. A first statistical value can be determined of a size distribution of cell-free DNA molecules ending within a first genomic window (e.g., on a genomic position when the window has a width of one) determined to have the rate above the threshold. The genomic positions of the first genomic window can be excluded from the first set of genomic positions when the first statistical value does not exceed a size threshold, e.g., the average size is not small enough or there are not a sufficient number of small DNA fragments (e.g., below a specified size) compared to all cell-free DNA molecules or those in a larger range.

The first statistical value can be compared to a second statistical value of a size distribution for cell-free DNA molecules determined to not have a rate above the threshold. If the two values are similar (e.g., which would not be expected for fetal or tumor tissue), then the first genomic window can be excluded from a set of preferred ending positions. Comparing the corresponding number to the reference value can include computing a first ratio (e.g., PETR) of the corresponding number and a number of cell-free DNA molecules covering any part of the genomic window for one sample, and optionally not ending in the genomic window, as described in section VII.A.2. The reference value can include a reference ratio of the measured number of reads ending within the genomic window and a number of cell-free DNA molecules covering the genomic window and not ending within the genomic window for the other sample. The first ratio can be required to be greater than a multiplicative factor (e.g., 4) times the reference ratio.

Another filter criteria can be that each genomic position of the first set of genomic positions can be required to have at least a specified number of cell-free DNA molecules ending on the genomic position. Using any of these techniques, the first set of genomic positions may comprise between 600 and 10,000 genomic positions.

In embodiments taking a difference among sets (e.g., use of Venn diagrams), the genomic positions whose rate (e.g., as determined from a genomic window) is above the threshold comprises a first superset, e.g., as shown in FIG. 28A as Set P and Set S. A third plurality of cell-free DNA molecules can be analyzed from at least one second additional sample having a reduced amount of the first tissue type (e.g., less or no fetal tissue or HCC tissue, as depicted in FIG. 28A) to identify a second superset, e.g., Set Q and Set S. The first set of genomic positions can include the genomic positions that are in the first superset and that are not in the second superset, e.g., Set P or Set S, depending on which tissue type is being analyzed.

As described in section VI, the first tissue type can have first tissue-specific alleles. A count can be made of the cell-free DNA molecule ending on the genomic position and including at least one of the plurality of first tissue-specific alleles. This count (number) of cell-free DNA molecules can be compared to the reference value.

C. Relative Abundance

Various examples of relative abundance values are provided herein, e.g., intact probability ($P_I$), p-value described in section VI.A.1, and the PETR value determined using a genomic window or a genomic position when the window is of width one. For PETR for a genomic position (window of width one), a corresponding number of the first plurality of cell-free DNA molecules ending on the genomic position can be computed for each genomic position of the first set of genomic positions. This can be done as part of determining that the first number (e.g., numerator) of the first plurality of cell-free DNA molecules end on any one of the first set of genomic positions. A third number (e.g., denominator) of cell-free DNA molecules covering the genomic position and not ending on the genomic position can be computed as part of determining the second number of cell-free DNA molecules. A first ratio of the corresponding number and the third number can be determined, and a mean of the first ratios used as the relative abundance.

For w-PETR, a corresponding number of cell-free DNA molecules ending within a first window (e.g., window A in FIG. 31A) including the genomic position can be computed for each genomic position of the first set of genomic positions. A third number of cell-free DNA molecules ending within a second window (e.g., of window B in FIG. 31A) including the genomic position can be computed. A means of first ratios of the corresponding numbers and the third numbers can be used as the relative abundance.

Another examples of a relative abundance value is a proportion of cell-free DNA molecules ending on a genomic window, e.g., measured as a proportion of sequenced DNA fragments ending on a preferred ending position. Thus, the second set of genomic positions can include all genomic positions corresponding to an end of at least one of the first plurality of cell-free DNA molecules.

D. Calibration Values

In various embodiments, the calibration value(s) can correspond to the calibration value(s) of the calibration data point(s) determined from the calibration sample(s) or any calibration values determined therefrom, e.g., of a calibration function that approximates the calibration data points. The one or more calibration samples may or may not include any additional sample used to determine the preferred ending sites.

For each of the one or more calibration samples, a corresponding proportional contribution of the first tissue type can be measured, e.g., using a tissue-specific allele. A corresponding relative abundance can be determined using the corresponding numbers of cell-free DNA molecules ending within the plurality of windows corresponding to the first set of genomic positions. The measured proportional contribution and relative abundance can provide a calibration data point. The one or more calibration data points can be a plurality of calibration data points that form a calibration function that approximates the plurality of calibration data points. Further details of use of calibration values can be found in U.S. Patent Publication 2013/0237431.

E. Classification of Proportional Contribution

In some embodiments, the preferred ending positions for a particular tissue can also be used to measure the absolute contribution of a particular tissue type in a sample, e.g. in number of genomes per unit volume (e.g. per milliliter). For example, a concentration of the tissue of interest could be measured in relation to the volume or weight of the cell-free DNA samples. In one implementation, quantitative PCR could be used to measure the number of cell-free DNA molecules ending at one or more preferred ends in a unit volume or unit weight of the extracted cell-free DNA sample. Similar measurements can be made for calibration samples, and thus the proportional contribution can be determined as a proportional contribution, as the contribution is a concentration per unit volume or unit weight.

Figure 39:
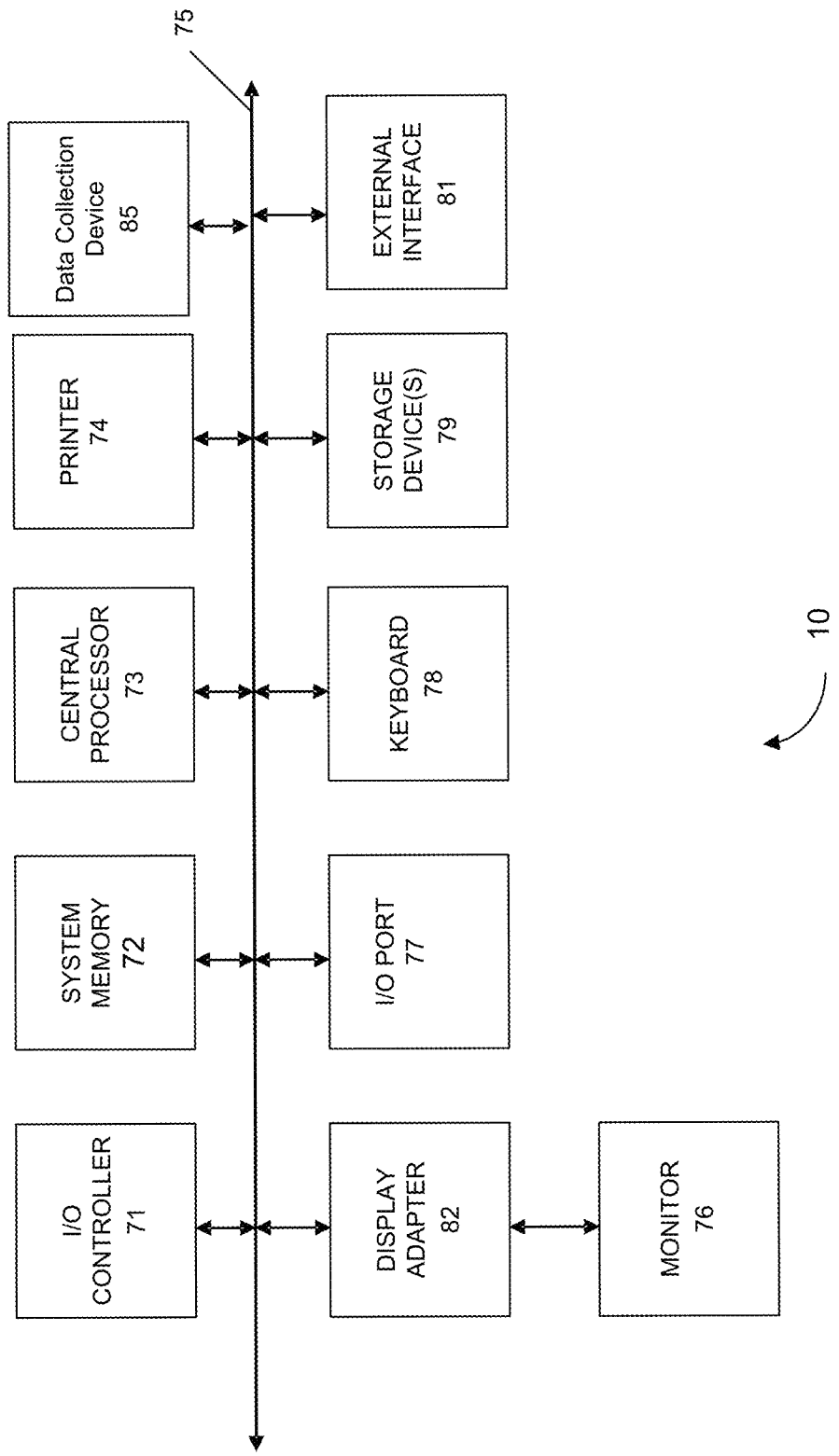
FIG. 39 shows a block diagram of an example computer system 10 usable with system and methods according to embodiments of the present invention.

In various embodiments when the first tissue type corresponds to tumor tissue, the classification can be selected from a group consisting of: an amount of tumor tissue in the subject, a size of the tumor in the subject, a stage of the tumor in the subject, a tumor load in the subject, and presence of tumor metastasis in the subject XI. Computer System Any of the computer systems mentioned herein may utilize any suitable number of subsystems. Examples of such subsystems are shown in FIG. 39 in computer apparatus 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 39 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of connections known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A method of analyzing a biological sample, including a mixture of cell-free DNA molecules from a plurality of tissues types that includes a first tissue type, to determine a classification of a proportional contribution of the first tissue type in the mixture, the method comprising:
  identifying at least one genomic region having a fragmentation pattern specific to the first tissue type;
  analyzing, by a computer system, a plurality of cell-free DNA molecules from the biological sample, wherein analyzing a cell-free DNA molecule includes:

determining a genomic position in a reference genome corresponding to at least one end of the cell-free DNA molecule;

identifying a first set of first genomic positions, each first genomic position having a local minimum of ends of cell-free DNA molecules corresponding to the first genomic position;

identifying a second set of second genomic positions, each second genomic position having a local maximum of ends of cell-free DNA molecules corresponding to the second genomic position;

determining a first number of the plurality of cell-free DNA molecules ending on any one of the first genomic positions in any one of the at least one genomic region;

determining a second number of the plurality of cell-free DNA molecules ending on any one of the second genomic positions in any one of the at least one genomic region;

computing a separation value using the first number and the second number; and determining the classification of the proportional contribution of the first tissue type by comparing the separation value to one or more calibration values determined from one or more calibration samples whose proportional contributions of the first tissue type are known.

2. The method of claim 1, wherein the first set of first genomic positions includes multiple genomic positions, wherein the second set of second genomic positions includes multiple genomic positions, wherein determining the first number of the plurality of cell-free DNA molecules includes determining a first amount of cell-free DNA molecules ending on each first genomic position, thereby determining a plurality of first amounts, wherein determining the second number of the plurality of cell-free DNA molecules includes determining a second amount of cell-free DNA molecules ending on each second genomic position, thereby determining a plurality of second amounts, and wherein computing the separation value includes:
determining a plurality of separate ratios, each separate ratio of one of the plurality of first amounts and one of the plurality of second amounts, and
determining the separation value using the plurality of separate ratios.

3. The method of claim 1, wherein the at least one genomic region includes one or more DNase hypersensitivity sites.

4. The method of claim 1, wherein each of the at least one genomic region having the fragmentation pattern specific to the first tissue type includes one or more first tissue-specific alleles in at least one of the one or more calibration samples.

5. The method of claim 1, wherein the at least one genomic region includes one or more ATAC-seq or micrococcal nuclease sites.

6. The method of claim 1, wherein the cell-free DNA molecules aligned to one genomic position of the first set of first genomic positions extend a specified number of nucleotides to both sides of the one genomic position.

7. The method of claim 6, wherein the specified number is between 10 and 80 nucleotides.

8. The method of claim 1, wherein identifying the first set of first genomic positions includes:
for each of a plurality of genomic positions:
determining a first amount of cell-free DNA molecules that are located at the genomic position and extend a specified number of nucleotides to both sides of the genomic position;
determining a second amount of cell-free DNA molecules that are located at the genomic position; and
determining a ratio of the first amount and the second amount; and
identifying a plurality of local minima and a plurality of local maxima in the ratios.

9. The method of claim 8, wherein, for a given genomic position of the plurality of genomic positions, the second amount corresponds to a total number of the cell-free DNA molecules aligning to the given genomic position.

10. The method of claim 1, wherein the mixture is plasma or serum.

11. The method of claim 1, wherein the plurality of cell-free DNA molecules is at least 1,000 cell-free DNA molecules.

12. The method of claim 11, wherein analyzing the plurality of cell-free DNA molecules from the biological sample includes sequencing the plurality of cell-free DNA molecules to obtain sequence reads, and wherein determining genomic positions of at least one end of the plurality of cell-free DNA molecules includes aligning the sequence reads to the reference genome.

13. A computer product comprising a non-transitory computer readable medium storing a plurality of instructions that when executed control a computer system to perform a method for analyzing a biological sample, including a mixture of cell-free DNA molecules from a plurality of tissues types that includes a first tissue type, to determine a classification of a proportional contribution of the first tissue type in the mixture, the method comprising:

identifying at least one genomic region having a fragmentation pattern specific to the first tissue type;

analyzing a plurality of cell-free DNA molecules from the biological sample, wherein analyzing a cell-free DNA molecule includes:
determining a genomic position in a reference genome corresponding to at least one end of the cell-free DNA molecule;
identifying a first set of first genomic positions, each first genomic position having a local minimum of ends of cell-free DNA molecules corresponding to the first genomic position;
identifying a second set of second genomic positions, each second genomic position having a local maximum of ends of cell-free DNA molecules corresponding to the second genomic position;
determining a first number of the plurality of cell-free DNA molecules ending on any one of the first genomic positions in any one of the at least one genomic region;
determining a second number of the plurality of cell-free DNA molecules ending on any one of the second genomic positions in any one of the at least one genomic region;
computing a separation value using the first number and the second number; and
determining the classification of the proportional contribution of the first tissue type by comparing the separation value to one or more calibration values determined from one or more calibration samples whose proportional contributions of the first tissue type are known.

14. The computer product of claim 13, wherein the first set of first genomic positions includes multiple genomic positions, wherein the second set of second genomic positions includes multiple genomic positions,
   wherein determining the first number of cell-free DNA molecules includes determining a first amount of cell-free DNA molecules ending on each first genomic position, thereby determining a plurality of first amounts,
   wherein determining the second number of cell-free DNA molecules includes determining a second amount of cell-free DNA molecules ending on each second genomic position, thereby determining a plurality of second amounts, and
   wherein computing the separation value includes:
      determining a plurality of separate ratios, each separate ratio of one of the plurality of first amounts and one of the plurality of second amounts, and
      determining the separation value using the plurality of separate ratios.

15. The computer product of claim 13, wherein the at least one genomic region includes one or more DNase hypersensitivity sites.

16. The computer product of claim 13, wherein each of the at least one genomic region having the fragmentation pattern specific to the first tissue type includes one or more first tissue-specific alleles in at least one of the one or more calibration samples.

17. The computer product of claim 13, wherein the at least one genomic region includes one or more ATAC-seq or micrococcal nuclease sites.

18. The computer product of claim 13, wherein the cell-free DNA molecules aligned to one genomic position of the first set of first genomic positions extend a specified number of nucleotides to both sides of the one genomic position.

19. The computer product of claim 18, wherein the specified number is between 10 and 80 nucleotides.

20. The computer product of claim 13, wherein identifying the first set of first genomic positions includes:
   for each of a plurality of genomic positions:
      determining a first amount of cell-free DNA molecules that are located at the genomic position and extend a specified number of nucleotides to both sides of the genomic position;
      determining a second amount of cell-free DNA molecules that are located at the genomic position; and
      determining a ratio of the first amount and the second amount; and
   identifying a plurality of local minima and a plurality of local maxima in the ratios.

21. The computer product of claim 20, wherein, for a given genomic position of the plurality of genomic positions, the second amount corresponds to a total number of the cell-free DNA molecules aligning to the given genomic position.

22. The computer product of claim 13, wherein the mixture is plasma or serum.

23. The computer product of claim 13, wherein the plurality of cell-free DNA molecules is at least 1,000 cell-free DNA molecules.

* * * * *